US008404714B2

(12) United States Patent
Vazquez-Anon et al.

(10) Patent No.: US 8,404,714 B2
(45) Date of Patent: *Mar. 26, 2013

(54) COMBINATIONS TO IMPROVE ANIMAL HEALTH AND PERFORMANCE

(75) Inventors: Mercedes Vazquez-Anon, Chesterfield, MO (US); Gavin Bowman, O'Fallon, MO (US); Steven Andrew Webb, Edwardsville, IL (US); James Richards, Lake Sherwood, MO (US); Robert Harrell, Troy, MO (US); Junmei Zhao, St. Louis, MO (US); Megharaja K. Manangi, O'Fallon, MO (US)

(73) Assignee: Novus International, Inc., St. Charles, MO (US)

( * ) Notice: Subject to any disclaimer, the term of this patent is extended or adjusted under 35 U.S.C. 154(b) by 129 days.

This patent is subject to a terminal disclaimer.

(21) Appl. No.: 12/811,559

(22) PCT Filed: Dec. 30, 2008

(86) PCT No.: PCT/US2008/088568
§ 371 (c)(1),
(2), (4) Date: Oct. 11, 2010

(87) PCT Pub. No.: WO2009/088879
PCT Pub. Date: Jul. 16, 2009

(65) Prior Publication Data
US 2011/0021461 A1    Jan. 27, 2011

Related U.S. Application Data

(60) Provisional application No. 61/019,148, filed on Jan. 4, 2008, provisional application No. 61/023,576, filed on Jan. 25, 2008, provisional application No. 61/080,443, filed on Jul. 14, 2008.

(51) Int. Cl.
A61K 31/47    (2006.01)
A61K 31/045    (2006.01)

(52) U.S. Cl. ........................................ 514/312; 514/728
(58) Field of Classification Search ............... 514/64, 514/312, 557, 728
See application file for complete search history.

(56) References Cited

U.S. PATENT DOCUMENTS

| | | | |
|---|---|---|---|
| 2,707,682 A | 5/1955 | Arkees et al. | |
| 2,938,053 A | 5/1960 | Blake et al. | |
| 3,284,212 A | 11/1966 | Rondenet et al. | |
| 4,027,043 A | 5/1977 | Schroeder et al. | |
| 4,079,153 A | 3/1978 | Coleman | |
| 4,087,561 A | 5/1978 | Bharucha et al. | |
| 4,088,793 A | 5/1978 | Bharucha et al. | |
| 4,207,043 A | 6/1980 | Falkinger | |
| 4,305,932 A | 12/1981 | Menachemoff et al. | |
| 4,460,588 A | 7/1984 | Serban et al. | |
| 4,592,915 A | 6/1986 | Goyett et al. | |
| 4,642,317 A | 2/1987 | Palmquist et al. | |
| 4,762,854 A | 8/1988 | Lloyd et al. | |
| 4,765,854 A | 8/1988 | McKeown | |
| 4,820,527 A | 4/1989 | Christensen et al. | |
| 4,871,551 A | 10/1989 | Spencer | |
| 4,952,590 A | 8/1990 | Magius | |
| 4,986,996 A | 1/1991 | Barlow et al. | |
| 5,000,964 A | 3/1991 | McCauley | |
| 5,066,498 A | 11/1991 | McCauley, III | |
| 5,167,835 A | 12/1992 | Harder | |
| 5,244,681 A | 9/1993 | Vinci et al. | |
| 5,282,379 A | 2/1994 | Harder et al. | |
| 5,348,755 A | 9/1994 | Roy | |
| 5,462,967 A | 10/1995 | Hayashi | |
| 5,591,467 A | 1/1997 | Bland | |
| 5,603,958 A | 2/1997 | Morein | |
| 5,656,319 A | 8/1997 | Barclay | |
| 5,698,244 A | 12/1997 | Barclay | |
| 5,795,602 A | 8/1998 | Craig et al. | |
| 5,891,491 A | 4/1999 | Owens | |
| 5,928,686 A | 7/1999 | Ivey | |
| 5,928,689 A | 7/1999 | Milkowski et al. | |
| 5,945,144 A | 8/1999 | Hahn et al. | |
| 5,985,336 A | 11/1999 | Ivey | |
| 6,008,409 A | 12/1999 | Hasseberg | |
| 6,017,564 A | 1/2000 | Owens et al. | |
| 6,177,108 B1 | 1/2001 | Barclay | |
| 6,299,913 B1 | 10/2001 | Block et al. | |
| 6,355,289 B1 | 3/2002 | Rolow et al. | |
| 6,436,453 B1 | 8/2002 | Lengerich et al. | |
| 6,593,283 B2 | 7/2003 | Hei et al. | |
| 6,846,478 B1 | 1/2005 | Doyle et al. | |
| 6,955,831 B2 | 10/2005 | Higgs et al. | |
| 7,084,175 B2 | 8/2006 | Wilson | |
| 7,258,880 B2 | 8/2007 | Piva | |
| 7,335,669 B2 * | 2/2008 | Selm et al. | 514/312 |

(Continued)

FOREIGN PATENT DOCUMENTS

| CA | 943962 A1 | 3/1974 |
|---|---|---|
| CA | 944135 A1 | 3/1974 |

(Continued)

OTHER PUBLICATIONS

Nocek et al., "The Effect of Trace Mineral Fortification Level and Source on Performance of Dairy Cattle", Journal of Dairy Science, vol. 89, No. 7, pp. 2679-2693 (2006).*
International Search Report and Written Opinion dated Feb. 27, 2009 from related International Application No. PCT/US2008/088568, 7 pgs.
Office Action dated Mar. 19, 2009 for related U.S. Appl. No. 11/676,457, 18 pgs.
Nitsan, The effects of force-feeding on enzymes of the liver, kidney, pancreas and disgestive tract of chicks, The British Journal of Nutrition, Sep. 1974, pp. 241-247, vol. 32, No. 2, Cambridge University Press, England.

(Continued)

Primary Examiner — Kevin E Weddington
(74) Attorney, Agent, or Firm — Polsinelli Shughart PC

(57) ABSTRACT

The present invention provides combinations of dietary supplements and methods of using of these combinations to improve the health and production performance of animals. In particular, the combinations of the invention comprise antioxidants, trace minerals, organic acids, essential amino acids, and mixtures thereof.

20 Claims, 9 Drawing Sheets

U.S. PATENT DOCUMENTS

| | | | |
|---|---|---|---|
| 7,465,471 | B2 | 12/2008 | Giesen et al. |
| 7,910,604 | B2 | 3/2011 | Vazquez-Anon et al. |
| 2002/0172737 | A1 | 11/2002 | Pinski et al. |
| 2003/0077254 | A1 | 4/2003 | Ramaekers |
| 2003/0077257 | A1 | 4/2003 | Britov |
| 2003/0162809 | A1 | 8/2003 | Selm et al. |
| 2004/0009206 | A1 | 1/2004 | Piva et al. |
| 2004/0028732 | A1 | 2/2004 | Von Falkenhausen et al. |
| 2004/0052895 | A1 | 3/2004 | Ivey |
| 2004/0076659 | A1 | 4/2004 | Shelford et al. |
| 2004/0115275 | A1 | 6/2004 | Tsou et al. |
| 2004/0156816 | A1 | 8/2004 | Anderson |
| 2005/0018847 | A1 | 1/2005 | Garay et al. |
| 2005/0019461 | A1 | 1/2005 | Cazemier |
| 2005/0100563 | A1 | 5/2005 | Hexamer |
| 2005/0100799 | A1 | 5/2005 | Hagiwara |
| 2005/0215623 | A1 | 9/2005 | Giesen et al. |
| 2007/0089847 | A1 | 4/2007 | Abou-Nemeh |
| 2007/0286925 | A1 | 12/2007 | Zhang |
| 2008/0014301 | A1 | 1/2008 | Vazquez-Anon et al. |
| 2008/0014323 | A1 | 1/2008 | Vazquez-Anon et al. |
| 2008/0015217 | A1 | 1/2008 | Vazquez-Anon et al. |
| 2008/0015218 | A1 | 1/2008 | Vazquez-Anon et al. |
| 2008/0119552 | A1 | 5/2008 | Navarro |
| 2010/0098802 | A1 | 4/2010 | Navarro |
| 2011/0008388 | A1 | 1/2011 | Navarro et al. |
| 2011/0021461 | A1 | 1/2011 | Vazquez-Anon et al. |
| 2011/0172269 | A1 | 7/2011 | Vazquez-Anon et al. |

FOREIGN PATENT DOCUMENTS

| | | |
|---|---|---|
| CA | 1261855 A1 | 9/1989 |
| CA | 2087792 A1 | 7/1993 |
| EP | 0466674 A1 | 1/1992 |
| EP | 1062879 | 6/1999 |
| EP | 0937706 A1 | 8/1999 |
| EP | 1041443 A2 | 10/2000 |
| EP | 1205115 A2 | 5/2002 |
| EP | 1536284 A1 | 1/2005 |
| FR | 2513491 A1 | 4/1983 |
| FR | 2795919 A1 | 1/2001 |
| GB | 1440183 A1 | 6/1976 |
| GB | 1444024 | 7/1976 |
| GB | 1537334 | 12/1978 |
| GB | 955316 A | 2/1979 |
| GB | 1356002 | 11/2011 |
| HU | 2921 | 11/1977 |
| JP | 58031944 A | 2/1983 |
| JP | 08107757 A | 4/1996 |
| JP | 10327751 A | 12/1998 |
| JP | 03270588 | 4/2002 |
| JP | 03107789 | 8/2012 |
| SU | 631517 A1 | 11/1978 |
| SU | 649396 A1 | 2/1979 |
| SU | 679578 A1 | 8/1979 |
| SU | 705334 A1 | 12/1979 |
| SU | 751381 A1 | 7/1980 |
| WO | 9503712 A1 | 2/1995 |
| WO | 96/35337 A1 | 11/1996 |
| WO | 9635337 A1 | 11/1996 |
| WO | 9733488 | 9/1997 |
| WO | WO 9904647 A1 * | 2/1999 |
| WO | 99/46646 A1 | 9/1999 |
| WO | 00/59877 A1 | 10/2000 |
| WO | 01/97799 A1 | 12/2001 |
| WO | 0197799 | 12/2001 |
| WO | 03/037103 A1 | 5/2003 |
| WO | 03/084346 A1 | 10/2003 |
| WO | 2008008637 A2 | 1/2008 |
| WO | 2008061078 A2 | 5/2008 |
| WO | 2008088568 A1 | 7/2008 |
| WO | 2009006475 A1 | 8/2009 |

OTHER PUBLICATIONS

Osman, Oil Content and Fatty Acid Composition of Some Varieties of Barley and Sorghum Grains, Grasas y Aceites, 2000, vol. 51, pp. 157-162.

Supplemental European Search Report dated Nov. 18, 2009 from related Application No. EP07871446.

Translation of Mexican Office action from related Appln. No. MX/a/2009/000302 on Dec. 12, 2011, 1 pg.

Translation of China Office action from related Appin. No. CN 200780033462.1 on Nov. 5, 2010, 10 pgs.

Office Action dated Nov. 27, 2006 for related U.S. Appl. No. 10/376,520, 5 pgs.

Office action dated Dec. 4, 2009 from related U.S. Appl. No. 11/676,457, 26 pgs.

Office action dated Dec. 9, 2008 from related U.S. Appl. No. 11/939,019, 21 pgs.

Notice of Allowance and Fees Due issued Nov. 16, 2010 for related U.S. Appl. No. 11/676,365, 11 pgs.

Notice of Allowance and Fee(s) Due dated Oct. 9, 2007 related U.S. Appl. No. 10/376,520, 4 pgs.

Office Action dated Mar. 28, 2006 for related U.S. Appl. No. 10/376,520, 6 pgs.

Office Action dated Apr. 18, 2008 for related U.S. Appl. No. 11/078,093, 109 pgs.

Office Action dated Jun. 2, 2010 for related U.S. Appl. No. 11/676,365, 37 pgs.

Office Action dated Jun. 29, 2009 for related U.S. Appl. No. 11/939,019, 21 pgs.

Office Action dated Jun. 9, 2010 for related U.S. Appl. No. 11/674,916, 25 pgs.

Office Action dated Jul. 13, 2007 for related U.S. Appl. No. 10/376,520, 4 pgs.

Notice of Allowance and Fee(s) Due dated Aug. 25, 2008 for related U.S. Appl. No. 11/078,093, 4 pgs.

Examiner Interview Summary dated Aug. 26, 2010 for related U.S. Appl. No. 11/676,365, 17 pgs.

Office Action dated Sep. 11, 2009 for related U.S. Appl. No. 11/674,916, 29 pgs.

Office Action dated Sep. 11, 2009 for related U.S. Appl. No. 11/676,461, 21 pgs.

Office Action dated Sep. 9, 2009 for related U.S. Appl. No. 11/676,365, 21 pgs.

International search report dated Apr. 15, 2004 for PCT/US03/27323, 4 pgs.

English translation from our foreign associate on Mar. 22, 2012 of an Office action issued on Feb. 29, 2012 in the related Chinese application No. 200780033462.1, 10 pages.

English translation from our foreign associate on May 7, 2012 of an Office action issued in the related Mexican application No. MX/a/2009/000302, 3 pages.

Office action dated Jun. 26, 2012 from related U.S. Appl. No. 12/811,559, 13 pages.

Visek, The mode of growth promotion by antibiotics, Journal of Animal Science, Apr. 1978, pp. 1447-1469, vol. 46, No. 5, American Society of Animal Science.

Zamora, Fatty Acid Composition of Some Common Ebible Fats and Oils. www.scientificpsychic.com/fitness/fattyacids.html.

International Search Report from related application No. PCT/US2007/084497 dated Sep. 28, 2008, 4 pages.

Dunkley, Compounds in Milk Accompanying Feeding of Ethoxyquin, J. Dairy Sci., 1968, vol. 51, No. 8, pp. 1215-1218.

Dunkley, Supplementing Rations with Tocopherol and Ethoxyquin to Increase Oxidative Stability, J. Dairy Sci., 1967, vol. 50, No. 4, pp. 492-499.

Han, "Carbohydrate fermentation and nitrogen metabolism of a finishing beef diet by ruminal microbes in continuous cultures as affected by ethoxyquin and(or) supplementation of monensin and tylosin," J. Anim. Sci., 2002, vol. 80, pp. 1117-1123.

International Search Report from related application No. PCT/US2007/072436 dated Dec. 18, 2007, 9 pages.

Linn, "Feed Efficiency of Lactating Dairy Cows," retrieved from web on Jun. 2, 2010, URL.

Van Nevel, "Determination of rumen microbial growth in vitro from P-labeled phosphate incorporation," British Journal of Nutrition, 1977, vol. 38, pp. 101-114.

Gauthier, "Organic Acids and Essential Oils, A realistic Alternative to Antibiotic Growth Promoters in Poultry." Forum Internacional de Avicultura 17 a 18 de Agosto 2005, Foz do Iguacu PR Brasil, pp. 148-157.

Boles et al. "Effects of barley variety fed to steers on carcass characteristics and color of meat" Journal of Animal Science 2004 vol. 82 pp. 2087-2091.
Tacon, The Nutrition and Feeding of Farmed Fish and Shrimp, A Training Manual, 25 pages, www.fao.org/documents, 1987. http://www.fao.org/docrep/field/003/ab467e/AB467E00.htm.
Afzalpurkar, Journal of the American Oil Chemists' Society 1980: 57 105-106.
Baur et al. Journal of the Americal Chemical Society 1945 67: 1899-190.
Fernandez, How does yeast respond to pressure, J. Medical and Biological Research (2005) 38: 1239-1245.
Aravind, Efficacy of Esterified Glucomannan to Counteract Mycotoxicosis in Naturally Contaminated Feed on Performance and Serum Biochemical and Hematological Parameters in Broilers 2003 Poultry Science 82:571-576.
Bailey, Effect of *Salmonella* in Young Chicks on Competitive Exclusion Treatment, 1998 Poultry Science 77:394-399.
Chowdhury, Effects of Feeding Blends of Grains Naturally Contaminated with *Fusarium* Mycotoxins on Performance, Metabolism, Hematology, and Immunocompetence of Ducklings, 2006: Poultry Science 84:1179-1185.
Danicke, Effect of Addition of a Detoxifying Agent to Laying Hen Diets Containing Contaminated or *Fusarium* Toxin-Contaminated Maize of Performance of Hens and Carrover of Zearalenone. 2002 Poultry Science 81:1671-1680.
Diaz, Evaluation of the Efficacy of Four Feed Additives Against the Adverse Effects of T-2 Toxin in Growing Broiler Chickens. 2005 J. Appl. Poultr. Res. 14:226-231.
Dwyer, Effects of Inorganic Adsorbants and Cyclopiazonic Acid in Broiler Chickens, 1997 Poultry Science 76: 1141-1149.
Edrington, Influence of a Superactivated Charcoal on the Toxic Effects of Aflatoxin or T-2 toxin in Growing Broilers, 1997 Poultry Science 76: 1205-1211.
Harvey, Comparison of two hydrated sodium calcium aliminosilicate compounds to experimentally protect growing barrows from Aflatoxicosis. J. Vet. Diagn. Invest 6:88-92 (1994).
Kubena, Effects of a Hydrated Sodium Calcium Aluminosilicate (T-Bind) on Mycotoxicosis in Young Broiler Chickens. 1998 Poultry Science 77: 1502-1509.
Ledoux, Efficacy of Hydrated Sodium Calcium Aluminosilicate to Ameliorate the Toxic Effects of Aflatoxin in Broiler Chicks, 1998 Poultry Science 77:204-210.
Lindemann, Potential Ameliorators of aflotoxicosis in Weaning/Growing Swine. J. Animal Sci. 1993 71:171-178.
Miazzo, Efficacy of Sodium Bentonite as a Detoxifier of Broiler Feed Contaminated with Alatoxin and Fumonisin, 2005 Poultry Science 84:1-8.
Phillips, Dietary Clay in the Chemopreventon of Afloxin-Induced Disease. Toxicological Science 52: (Supp) 118-126, (1999).
Raymond, Effects of Feeding a Blend of Grains Naturally Contaminated with *Fusarium* mycotoxins on feed intake, metabolism, and indices of athletic performance of excercised horses. J. Animal. Science. 2005 83: 1267-1273.
Schell, Effectivness of different types of clay for reducing the detrimental effects of aflatoxin-contaminated diets on performance and serum profiles of weaning pigs. J. Animal Science, 1993: 71:1226-1231.
Smith, Dietary Hydrated socium calcium aliumino silicate reduction of aflatoxin M1 residue in dairy goat milk and effects on milk production and components. J. Animal Sci. 1994, 72:677-682.
Swamy, Effects of Feeding Blends of Grains Naturally Contaminated with *Fusarium* Mycotoxins on Production and Metabolism in Broilers. 2002 Poultry Science 81:966-975.
Karson, Biosynthesis of Yeast Mannan, Properties of a Mannosylphosphate Transferase in *Saccaromyces cerevisia*, Journal of Biological Chemistry, vol. 253, No. 18, 6484-6492, (1978).
Lesage, Cell Wall Assembly in *Saccharomyces cerevisiae* Microbiology and Molecular Biology Reviews, vol. 70. No. 2, 317-343.
Mager, Stress response of Yeast, Biochem J. 290, 1-13 (1993).
Perez, Monitoring Stress-Related Genes during the Process of Biomass Propagation of *Saccharomyces cerevisias* Strains Used for Wine Making, Applied and Environmental Microbiol Nov. 2005 6831-6837.
Levin, Cell Wall Integrity Signaling in *Saccharomyces cerevisiae*, Microbiol and Molecular Biol. Revs. Jun. 2005, 262-291.

Lushchak, Budding yeast *Saccharomyces cerevisiae* as a model to study oxidative modification of proteins in eukaryotes, Acta Biochemica Polinica vol. 53 No Apr. 2006 670-684.
Piper, Weak Acid adaptation: the stress response that convers yeasts with resistance to organic acid food presivetatives. Microbiology (2001) 147, 2653.
Rodriguez,-Pena, The yeast cell wall chip—a tool to analyse the regulation of cell wall biogenesis in *Saccharomyces cerevisiae*, Microbiology (2005) 151-2241-2249.
Schuller, Global Phenotypic Analysis and Transcriptional Profiling Defines the Weak Acid Stess Respons Gegulon in *Saccaromyces cerevisiae*, Molecular Biology of the Cell, vol. 15, 706-720, (2004).
Seymore, Stress Induction of HSP30, the plasma membrane heat shock protein gene of *Saccharomyces cerevisiase* appears not to use known stress-regulated transcription factors, Microbiology (1999) 145, 231-239.
Trott, SYM1 is the Stress IInduced *Saccharomyces cerevisiae* Ortholog of the Mammalian Kidney Disease Gene Mpv17 and Is Required for Ethanol Metabolism and Tolerance during Heat Shock, Eukaryotic cell Jun. 2004 620-631.
Sun, Broiler Performance and Intestinal Alterations When Fed Drug-Free Diets, Masters Thesis, Virginia Polytecnhic, 2004.
Letter from Chinese Associate dated Nov. 8, 2012 with translation of Decision on Rejection issued by the Chinese Patent Office on Oct. 11, 2012 in related application No. CN200780033462.1, 15 pages.
Office action dated Dec. 31, 2012 from related U.S. Appl. No. 13/023,781, 17 pgs.
Anderson, "Gut microbiology and growth-promoting antibiotics in swine, Pig News and Information," 1999, pp. 115N-122N, vol. 20, No. 4, CABI Publishing, Famham Royal.
BASF Fine Chemicals, "Effect of Luprosil(R) NC applications to littler on the health and performance of turkeys," 1990, BASF Technical Bulletin KC 9037.
Bedford, "Removal of antibiotic growth promoters from poultry diets: implications and strategies to minimise subsequent problems," World's Poultry Science Journal, Dec. 2000, pp. 347-365, vol. 56.
Bolduan, "Die wirkung von Propion-und Ameisensaure in der Ferkelaufzucht", J. Anim. Physiol. A. Anim. Nutr., 1988, pp. 72-78, vol. 59.
Bone, "The production of urinary phenols by gut bacteria and their possible role in the causation of large bowel cancer," The American Journal of Climincal Nutrition, Dec. 1976, pp. 1448-1454, vol. 29, No. 12.
Botermans, "The exocrine pancreas in pig growth and performance, Biology of the Pancreas in Growing Animals," 1999, pp. 395-408, Elsevier Science.
Brachet, "Transport of Methionine Hydroxy Analog across the Brush Border Membrane of Rat Jejunum," The Journal of Nutrition, 1987, pp. 1241-1246, vol. 117, Wistar Institute of Anatomy and Biology, Philadelphia.
Burns, Sulfur Amino Acid Requirements of immature Beagle Dogs, Journal of Nutrition, 2981, vol. 111, No. 12, pp. 2117-2124, (1981).
Cha, "Identification of Aroma-Active Compounds in Korean Salt-Fermented Fishes by Aroma Extract Dilution Analysis," Korean Society of Food Science and Nutrition, 1999, vol. 28, No. 2, pp. 312-318.
Chaveerach, "In Vitro Study on the Effect of Organic Acids on *Campylobacter jejuni/coli* Populations in Mixtures of Water and Feed," Poultry Science, May 2002, pp. 621-628, vol. 81, No. 5.
Cherrington, "Organic Acids: Chemistry, Antibacterial Activity and Practical Applications, Advances in Microbial Physiology," 1991, pp. 87-108, vol. 32.
Coates, "The Effect of Antibiotics on the Intestine of the Chick," The British Journal of Nutrition, 1995, pp. 110-119, vol. 9, No. 1, Cambridge University Press, Cambridge.
Cole, "The Effect on Performance and Bacterial Flora of Lactic acid, Propionic acid, Calcium propionate and Calcium acrylate in the Drinking Water of Weaned Pigs," The Veterinary Record, Nov. 2, 1968, pp. 459-464, vol. 83, British Veterinary Association, London.
Corthier, "Interrelationships between Digestive Proteolytic Activities and Production and Quantitation of Toxins in Pseudomembranous Colitis Induced by *Clostridium difficile* in Gnotobiotic Mice, Infection and Innunity," Dec. 1989, pp. 3922-3927, vol. 57, No. 12, American Society for Microbiology, Washington.

Cranwell, Development of the Neonatal Gut and Enzyme Systems, The Neonatal Pig—Development and Survival, 1995, pp. 99-154, M.A. Varley, CAB International, Oxon.

Dierick, "Influence of the gut flora and of some growth promoting feed additives on nitrogen metabolism in pigs. I. Studies in vitro," Livestock Production Science, 1986, pp. 161-176, vol. 14, Elsevier Science Publishers, Amsterdam.

Dierick, "Influence of the gut flora and of some growth promoting feed additives on nitrogen metabolism in pigs. II. Studies in vivo," Livestock Production Science, 1986, pp. 177-193, vol. 14, Elsevier Science Publishers, Amsterdam.

Doerr, "Possible anti-fungal effects of hydroxy-methylthio-butanoic acid (HMB)," Poultry Science, 1995, vol. 74(1), pp. 23.

Dunnington, "Enzyme Activity and Organ Development in Newly Hatched Chicks Selected for High or Low Eight-Week Body Weight," Poultry Science, 1995, pp. 761-770, vol. 74, No. 5.

Eckel, Zum Einflub von Ameisensaure auf die Konzentrationen an Ammoniak und biogenen Aminen im Gastrointestinaltrakt, J. Amin. Physiol. a. Anim. Nutr., 192, pp. 198-205, vol. 67, (1992).

Eidelsburger, Zum Einflub von Fumarsaure, Salzsaure, Natriumformiate, Tylosin und Toyocerin auf tagliche Zunahmen, Futteraufnagme, Futterverwertug und Verdaulichkeit, J. Anim. Physiol. a. Anim. Nutr., 1992, pp. 82-92, vol. 68.

Eidelsburger, Zum Einflub von Ameisenaure, Calciumformiat und Natriumhydrogencarbonat auf pH-Wert, Trockenmassegehalt, Konzentration an Carbonsauren und Ammoniak in verschiedenen Segmenten des Gastrointestinaltraktes, J. Anim. Physiol. A. Anim. Nutri., 1992, pp. 30-32, vol. 68.

Engelhardt, "Absorption of Short-chain Fatty Acids and Their Role in the Hindgut of Monogastric Animals," Animal Feed Science and Technology, 1989, pp. 43-53, vol. 23, Elsevier Science Publishers, Amsterdam.

Enthoven, "Antibacterial properties of 2-hydroxy-4-(methylthio)butyric Acid (HMB, alimet)," Eur. Assoc. Anim. Prod. Proc., 2002, EEAP, Cairo.

Franti, "Antibiotic Growth Promotion: Effects of Zinc Bacitracin and Oxytetracycline on the Digestive, Circulatory, and Excretory Systems of New Hampshire Cockerels," Poultry Science, 1972, pp. 1137-1145, vol. 51, No. 4.

Gabert, "The effect of fumaric acid and sodium fumarate supplementation to diets for weanling pigs on amino acid digestibility and volatile fatty acid concentrations in ileal digesta," Animal Feed Science and Technology, 1995, pp. 243-254, vol. 53, Elsevier Science.

Gedek, Zum Einflub von Fumarsaure, Salzsaure, Natriumformiat, Tylosin und Toyocerin auf die Keimzahlen der Mikroflora und deren Zusammensetzung in verschiedenen Segmenten des Gastrointestinaltraktes, J. Anim. Physiol. a. Anim. Nutr., 1992, pp. 209-217, vol. 58.

Hadron, "Effect of different dosages of an organic-acid mixture in broiler diets," Archiv fuer Gefluegelkunde, 2001, pp. 22-27, vol. 65—Abstract Only.

Harada, "Effect of short-chain fatty acids on the secretory response of the ovine exocrine pancreas," American Journal of Physiology, Mar. 1983, pp. G284-G290, vol. 244, No. 3, The American Physiological Society.

Harada, "Postnatal development of biliary and pancreatic exocrine secretion in piglets," Comparative Biochemistry and Physiology, 1988, pp. 43-51, vol. 91A, No. 1, Pergamon Press, London.

Harada, "Comparison of Pancreatic Exocrine Secretion via Endogenous Secretin by Intestinal Infusion of Hydrochloric Acid and Monocarboxylic Acid in Anesthetized Piglets," Japanese Journal of Physiology, 1986, pp. 843-856, vol. 36, No. 5.

Huyghebaert, "The influence of the addition of 'organic acid'-preparations on the zootechnical performances of broiler chickens", Report: CLO-DVV, 1999.

Kato, "Effect of Short-Chain Fatty Acids on Pancreatic Exocrine Secretion in Calves Aged 2 Weeks and 13 Weeks," Japanese Veterinary Science, Dec. 1989, pp. 1123-1127, vol. 51, No. 6, Japanese Society of Veterinary Science.

Knight, "Comparative Absorption of 2-Hydroxy-4 (Methylthio) butanoic Acid and L-Methionine in the Broiler Chick, Journal of Nutrition," Nov. 1984, pp. 2179-2186, vol. 114, No. 11, Wistar Institute of Anatomy and Biology, Philadelphia.

Lamikanra, "Biochemical and Microbial Changes during the Storage of Minimally Processed Cantaloupe," Journal of Agricultural and Food Chemistry, 2000, vol. 48(12), Abstract, American Chemical Society.

Makkink, "Acid binding capacity in feedstuffs, Feed International," Oct. 2001, pp. 24-27.

Martin, The Effect of Tuber Composition on Potato Crisp Flavour, Department of Food Science & Technology, University of Reading, proceedings of the Weuman Flavour Research Symposium, Germany, Jun. 22-25, 1999, Chemical Abstracts, Database No. 136:69008.

Mroz, "Supplementary organic acids and their interactive effects with microbial phytase in diets for pigs and poultry", Proceedings, Annual Conference on Phytase in Animal Nutrition, 2000, pp. 1-25, Lublin, Poland.

Nitsan, "Growth and development of the digestive organs and some enzymes in broiler chicks after hatching," British Poultry Science, Jul. 1991, pp. 515-523, vol. 32, No. 3.

Ozer, Effect of addition of amino acids, treatment with beta-galactosidase and use of heat-shocked cultures on the acetaldehyde level in yoghurt, International Journal of Dairy Technology, 2002, vol. 55(4), Abstract, Blackwell Science Ltd.

Partanen, "Organic acids—their efficacy and modes of action in pigs, Gut Environment of Pigs," 2001, pp. 201, Nottingham University Press, Nottingham, UK.

Partanen, "Organic acids for performance enhancement in pig diets", Nutr. Res. Rev., 1999, pp. 117-145, vol. 12.

Robinson, "Influence of Abomasal Infusion of High Levels of Lysine or Methionine, or Both, on Ruminal Fermentation, Eating Behaviour and Performance of Lactating Dairy Cows", Journal of Animal Science, 2000, vol. 78, No. 4, pp. 1067-1077.

Roura, "Prevention of Immunologic Stress Contributes to the Growth-Permitting Ability of Dietary Antibiotics in Chicks", The Journal of Nutrition, 1992, pp. 2383-2390, vol. 122, Wistar Institute of Anatomy and Biology, Philadelphia.

Scipioni, Ricerche sull'impiego di diete acidificante nello svezzamento precoce dei suinetti, Zool. Nutr. Anim., 1978, pp. 201-218, vol. 4.

Smit, "Flavour Formation by Enzymatic Conversion of Amino Acids, Proceedings of the Weurman Flavour Research Symposium," Germany, Jun. 22-25, 1999, Chemical Abstracts, Database No. 136:84940.

Smulders, "Effect of antimicrobial growth promoter in feeds with different levels of undigestible protein on broiler performance," Proceedings, World's Poultry Sci. Meeting, Aug. 1999, pp. 177-179, Veldhoven, Netherlands.

Thaela, "Effect of lactic acid supplementation in pigs after weaning," Journal of Animal and Feed Science, 1998, pp. 181, vol. 7.

Thomlinson, "Dietary manipulation of gastric pH in the prophylaxis of enteric disease in weaned pigs: Some field observations," The Veterinary Record, Aug. 1981, pp. 120-122, vol. 109, British Veterinary Associate, London.

* cited by examiner

COMBINATIONS TO IMPROVE ANIMAL HEALTH AND PERFORMANCE

FIELD OF THE INVENTION

The present invention generally relates to combinations of dietary supplements that improve the general health and performance of animals.

BACKGROUND OF THE INVENTION

There is a natural balance between the formation of free radicals during normal cellular metabolism and the endogenous antioxidant capacity of vertebrate cells that prevents the accumulation of free radicals. In situations where the levels of free radicals exceed the antioxidant capacity of the cell, however, oxidative stress may occur. Oxidative stress is essentially the toxic accumulation of high levels of free radicals, whereby the free radicals may damage the cells by oxidizing fatty acids of the cell membranes or interacting with DNA or proteins. High producing reproductive and growing animals are particularly prone to oxidative stress, and the situation appears to be exacerbated under certain environmental, physiological, and dietary conditions. Consequently, oxidative stress may compromise the health status and impair the production performance of such animals.

Dietary lipids such as supplemental fats, oil seeds, and distillers grains, if not stabilized, not only may contribute significantly to the load of free radicals in the animal, but also may negatively affect the growth of beneficial intestinal microflora. Thus, dietary antioxidants are useful for preventing the oxidation of dietary lipids in the final feed and for reducing free radical damage to the intestinal microorganisms and the animal. The endogenous antioxidant defense mechanism of the animal also depends upon other dietary nutrients, such as trace minerals and vitamins. Feeding adequate levels of trace minerals has been shown to benefit the health status of cattle by improving the immune response and antioxidant status, thereby leading to better animal performance. However, not all sources of trace mineral are equally available. Because of dietary antagonisms, organic trace minerals have been shown to have higher bioavailability than the inorganic forms. Furthermore, dietary organic acids have been shown to improve the microflora in the digestive tract, which may benefit feed and nutrient intake. Thus, there is a need for combinations of antioxidants, trace minerals, essential amino acids, and/or organic acids that can be readily mixed with animal feed rations for the improved health and antioxidant status of the animal, as well as increased production performance of the animal.

SUMMARY OF THE INVENTION

Among the various aspects of the invention, therefore, is the provision of combinations that improve the health and performance of animals. One aspect of the invention encompasses a combination comprising at least one antioxidant selected from the group consisting of 6-ethoxy-1,2-dihydro-2,2,4-trimethylquinoline, tertiary butyl hydroquinone, butylated hydroxyanisole, and butylated hydroxytoluene; a hydroxy analog of methionine; and at least one organic trace mineral. The organic trace mineral comprises a metal chelate or a metal salt comprising at least one metal ion and at least one ligand, wherein the ligand comprises a compound comprising Formula (III):

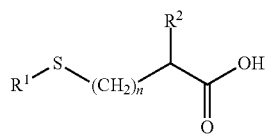

wherein:
$R^1$ is selected from the group consisting of methyl and ethyl;
$R^2$ is selected from the group consisting of hydroxy and amino; and
n is an integer from 0 to 2.

Another aspect of the invention provides a combination comprising at least one antioxidant selected from the group consisting of 6-ethoxy-1,2-dihydro-2,2,4-trimethylquinoline, tertiary butyl hydroquinone, butylated hydroxyanisole, and butylated hydroxytoluene; at least one organic acid; and at least one organic trace mineral. The organic trace mineral comprises a metal chelate or a metal salt comprising at least one metal ion and at least one ligand, wherein the ligand comprises a compound comprising Formula (III):

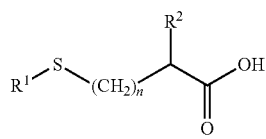

wherein:
$R^1$ is selected from the group consisting of methyl and ethyl;
$R^2$ is selected from the group consisting of hydroxy and amino; and
n is an integer from 0 to 2.

A further aspect of the invention encompasses a method for reducing oxidative stress in an animal. The method comprises feeding the animal a combination comprising at least one antioxidant selected from the group consisting of 6-ethoxy-1,2-dihydro-2,2,4-trimethylquinoline, tertiary butyl hydroquinone, butylated hydroxyanisole, and butylated hydroxytoluene; a hydroxy analog of methionine; and at least one organic trace mineral. The organic trace mineral comprises a metal chelate or a metal salt, the metal chelate or metal salt comprising at least one metal ion and at least one ligand, wherein the ligand comprises a compound comprising Formula (III):

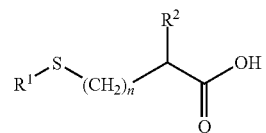

wherein:
$R^1$ is selected from the group consisting of methyl and ethyl;
$R^2$ is selected from the group consisting of hydroxy and amino; and
n is an integer from 0 to 2.

Still another aspect of the present invention provides a method for reducing oxidative stress in an animal. The method comprises feeding the animal a combination comprising at least one antioxidant selected from the group consisting of 6-ethoxy-1,2-dihydro-2,2,4-trimethylquinoline, tertiary butyl hydroquinone, butylated hydroxyanisole, and butylated hydroxytoluene; at least one organic acid; and at least one organic trace mineral. The organic trace mineral comprises a metal chelate or a metal salt comprising at least one metal ion and at least one ligand, wherein the ligand comprises a compound comprising Formula (III):

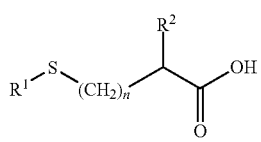

(III)

wherein:
$R^1$ is selected from the group consisting of methyl and ethyl;
$R^2$ is selected from the group consisting of hydroxy and amino; and
n is an integer from 0 to 2.

Other aspects and features of the invention are detailed below.

DETAILED DESCRIPTION OF THE INVENTION

Figure 1:
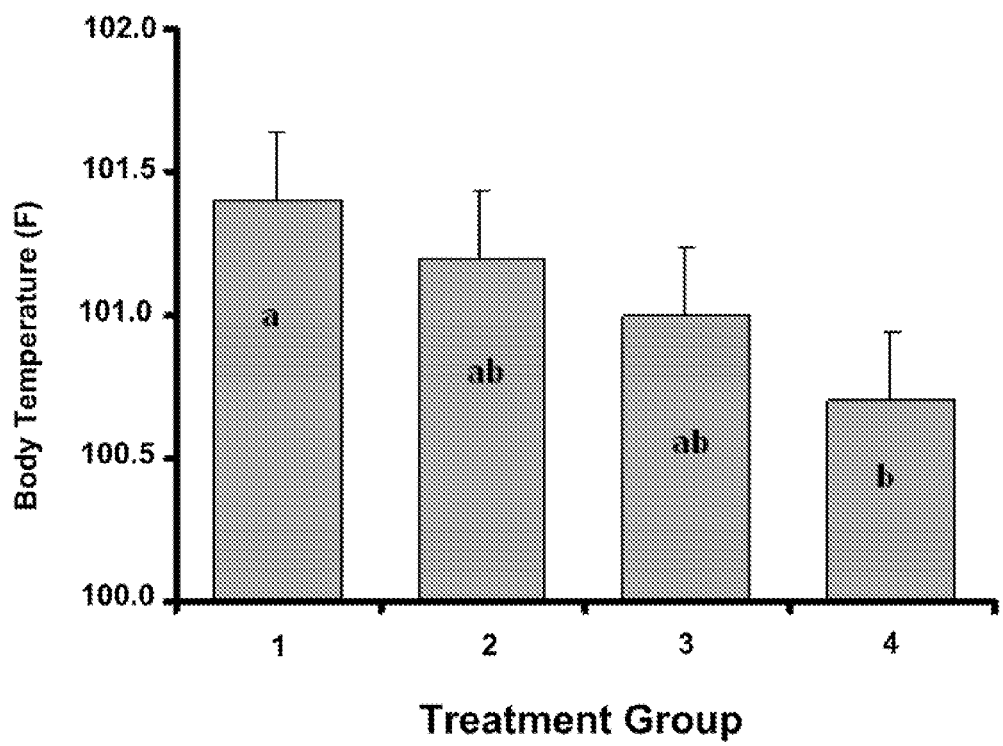
FIG. 1 illustrates the effects of dietary organic acids and/or antioxidants on sow body temperature at five days post-farrowing. Plotted is the body temperature in ° F. as a function of treatment group (n=28). Treatment 1 is the control group; Treatment 2 received organic acids (i.e., a blend of organic acids and 2-hydroxy-4(methylthio)butanoic acid); Treatment 3 received antioxidants (i.e., a blend of 6-ethoxy-1,2-dihydro-2,2,4-trimethylquinoline (ethoxyquin) and tertiary butyl hydroquinone); and Treatment 4 received a combination of organic acids and antioxidants. Treatments with the same superscripts (letters) are not significantly different.

The present invention provides several combinations and methods of using the combinations to improve animal health and performance. The combination of ingredients provides more beneficial effects that each of the ingredients individually. Without being bound by any particular theory, it is believed that the combinations improve the animal's antioxidant status and general health, which subsequently impact the animal's production performance. The combinations may be beneficially provided to a variety of animals such as poultry, swine, and ruminants.

(I) Combinations

One aspect of the invention encompasses combinations that improve animal health and performance. Non-limiting examples of combinations of the invention include: (1) at least one antioxidant, a hydroxy analog of methionine, and at least one organic trace mineral; (2) at least one antioxidant, and at least one organic acid, and at least one organic trace mineral; (3) at least one antioxidant and at least one organic acid; (4) at least one antioxidant and at least one organic trace mineral; (5) at least one antioxidant, at least one organic acid, and a hydroxy analog of methionine; (6) at least one antioxidant and at least one mycotoxin binder; and (7) at least one antioxidant, at least one mycotoxin binder, and at least one organic trace mineral; (8) at least one organic trace mineral and at least one organic acid; and (9) at least one antioxidant, at least one organic trace mineral; at least one organic acid, at least one immune stimulating agent, and at least one tissue regeneration agent. Suitable ingredients for each combination are described below.

(a) Antioxidants

The combinations of the invention typically include at least one antioxidant. A variety of antioxidants or combination of antioxidants are suitable for use in the combinations. The antioxidant may comprise a quinoline compound. Typically, the quinoline compound will be a substituted 1,2-dihydroquinoline. Substituted 1,2-dihydroquinoline compounds suitable for use in the invention generally comprise Formula (I):

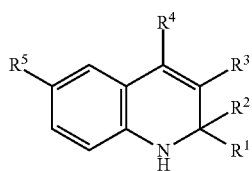

(I)

wherein:

$R^1$, $R^2$, $R^3$ and $R^4$ are independently selected from the group consisting of hydrogen and an alkyl group having from 1 to about 6 carbons; and $R^5$ is an alkoxy group having from 1 to about 12 carbons.

In an iteration, the substituted 1,2-dihydroquinoline comprises Formula (I), wherein:

$R^1$, $R^2$, $R^3$ and $R^4$ are independently selected from the group consisting of hydrogen and an alkyl group having from 1 to about 4 carbons;

and $R^5$ is an alkoxy group having from 1 to about 4 carbons.

In one preferred embodiment, the substituted 1,2-dihydroquinoline will be 6-ethoxy-1,2-dihydro-2,2,4-trimethylquinoline comprising Formula (II):

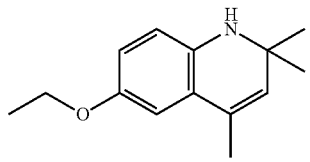

(II)

The compound, 6-ethoxy-1,2-dihydro-2,2,4-trimethylquinoline, commonly known as ethoxyquin, is sold under the trademark AGRADO®. The present invention also encompasses salts of ethoxyquin and other compounds comprising Formula (I). Ethoxyquin and other compounds having Formula (I) may be purchased commercially from Novus International, Inc. (St. Louis, Mo.) or made in accordance with methods generally known in the art, for example, as detailed in U.S. Pat. No. 4,772,710, which is hereby incorporated by reference in its entirety.

A variety of other antioxidants are suitable for use in the combinations of the present invention. In some embodiments, the antioxidant may be a compound that interrupts the free-radical chain of oxidative reactions by protonating free radicals, thereby inactivating them. Alternatively, the antioxidant may be a compound that scavenges the reactive oxygen species. In still other embodiments, the antioxidant may be a synthetic compound, a semi-synthetic compound, or a natural (or naturally-derived) compound.

Suitable antioxidants include, but are not limited to, ascorbic acid and its salts, ascorbyl palmitate, ascorbyl stearate, anoxomer, n-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline (ethoxyquin), ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate, flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, n-hydroxysuccinic acid, hydroxytryrosol, hydroxyurea, rice bran extract, lactic acid and its salts, lecithin, lecithin citrate; r-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and deltatocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, wheat germ oil, zeaxanthin, or combinations thereof.

Exemplary antioxidants include synthetic substituted phenolic compounds, such as tertiary butyl hydroquinone (TBHQ), butylated hydroxyanisole (BHA), or butylated hydroxytoluene (BHT); 6-ethoxy-1,2-dihydro-2,2,4-trimethylquinoline (ethoxyquin); gallic acid derivatives, such as n-propyl gallate; vitamin C derivatives, such as ascorbyl palmitate; lecithin; and vitamin E compounds, such as, alpha-tocopherol.

The combinations of the invention may comprise at least one antioxidant. In some embodiments, the combinations of the invention may comprise more than one of antioxidant. Combinations of antioxidants generally are formulated so that one antioxidant is more effective at reducing the oxidation of animal fat or fish fat compared to the second antioxidant, and the second antioxidant is more effective at reducing the oxidation of plant fat, such as vegetable oils, compared to the first antioxidant. By formulating the combination of antioxidants in this manner, a broad spectrum of fat sources, including fat sources relatively high in unsaturated fatty acids, may be utilized in the animal feed ration or water source.

In some embodiments, a combination of the invention may comprise two antioxidants. Non-limiting examples of suitable combinations of two antioxidant are set forth in Table A (i.e., the first antioxidant in column one is combined with the second antioxidant in column two).

TABLE A

| First Antioxidant | Second Antioxidant |
|---|---|
| 6-ethoxy-1,2-dihydro-2,2,4-trimethylquinoline | tert butyl hydroquinone (TBHQ) |
| 6-ethoxy-1,2-dihydro-2,2,4-trimethylquinoline | butylated hydroxyanisole (BHA) |
| 6-ethoxy-1,2-dihydro-2,2,4-trimethylquinoline | butylated hydroxytoluene (BHT) |
| 6-ethoxy-1,2-dihydro-2,2,4-trimethylquinoline | propyl gallate |
| 6-ethoxy-1,2-dihydro-2,2,4-trimethylquinoline | ethyl gallate |
| 6-ethoxy-1,2-dihydro-2,2,4-trimethylquinoline | ascorbic acid |
| 6-ethoxy-1,2-dihydro-2,2,4-trimethylquinoline | ascorbyl palmitate |
| 6-ethoxy-1,2-dihydro-2,2,4-trimethylquinoline | ascorbyl stearate |
| 6-ethoxy-1,2-dihydro-2,2,4-trimethylquinoline | lecithin |
| 6-ethoxy-1,2-dihydro-2,2,4-trimethylquinoline | alpha-tocopherol |
| 6-ethoxy-1,2-dihydro-2,2,4-trimethylquinoline | an ascorbate |
| 6-ethoxy-1,2-dihydro-2,2,4-trimethylquinoline | anoxomer |
| 6-ethoxy-1,2-dihydro-2,2,4-trimethylquinoline | N-acetylcysteine |
| 6-ethoxy-1,2-dihydro-2,2,4-trimethylquinoline | benzyl isothiocyanate |
| 6-ethoxy-1,2-dihydro-2,2,4-trimethylquinoline | m-aminobenzoic acid |
| 6-ethoxy-1,2-dihydro-2,2,4-trimethylquinoline | o-aminobenzoic acid |
| 6-ethoxy-1,2-dihydro-2,2,4-trimethylquinoline | p-aminobenzoic acid (PABA) |
| 6-ethoxy-1,2-dihydro-2,2,4-trimethylquinoline | caffeic acid |
| 6-ethoxy-1,2-dihydro-2,2,4-trimethylquinoline | canthaxantin |
| 6-ethoxy-1,2-dihydro-2,2,4-trimethylquinoline | alpha-carotene |
| 6-ethoxy-1,2-dihydro-2,2,4-trimethylquinoline | beta-carotene |
| 6-ethoxy-1,2-dihydro-2,2,4-trimethylquinoline | beta-caraotene |
| 6-ethoxy-1,2-dihydro-2,2,4-trimethylquinoline | beta-apo-carotenoic acid |
| 6-ethoxy-1,2-dihydro-2,2,4-trimethylquinoline | carnosol |
| 6-ethoxy-1,2-dihydro-2,2,4-trimethylquinoline | carvacrol |
| 6-ethoxy-1,2-dihydro-2,2,4-trimethylquinoline | a catechin |
| 6-ethoxy-1,2-dihydro-2,2,4-trimethylquinoline | cetyl gallate |
| 6-ethoxy-1,2-dihydro-2,2,4-trimethylquinoline | chlorogenic acid |
| 6-ethoxy-1,2-dihydro-2,2,4-trimethylquinoline | citric acid |
| 6-ethoxy-1,2-dihydro-2,2,4-trimethylquinoline | a citrate |
| 6-ethoxy-1,2-dihydro-2,2,4-trimethylquinoline | clove extract |
| 6-ethoxy-1,2-dihydro-2,2,4-trimethylquinoline | coffee bean extract |
| 6-ethoxy-1,2-dihydro-2,2,4-trimethylquinoline | p-coumaric acid |
| 6-ethoxy-1,2-dihydro-2,2,4-trimethylquinoline | 3,4-dihydroxybenzoic acid |
| 6-ethoxy-1,2-dihydro-2,2,4-trimethylquinoline | N,N'-diphenyl-p-phenylenediamine (DPPD) |
| 6-ethoxy-1,2-dihydro-2,2,4-trimethylquinoline | dilauryl thiodipropionate |
| 6-ethoxy-1,2-dihydro-2,2,4-trimethylquinoline | distearyl thiodipropionate |
| 6-ethoxy-1,2-dihydro-2,2,4-trimethylquinoline | 2,6-di-tert-butylphenol |
| 6-ethoxy-1,2-dihydro-2,2,4-trimethylquinoline | dodecyl gallate |
| 6-ethoxy-1,2-dihydro-2,2,4-trimethylquinoline | edetic acid |
| 6-ethoxy-1,2-dihydro-2,2,4-trimethylquinoline | ellagic acid |
| 6-ethoxy-1,2-dihydro-2,2,4-trimethylquinoline | erythorbic acid |
| 6-ethoxy-1,2-dihydro-2,2,4-trimethylquinoline | sodium erythorbate |
| 6-ethoxy-1,2-dihydro-2,2,4-trimethylquinoline | esculetin |
| 6-ethoxy-1,2-dihydro-2,2,4-trimethylquinoline | esculin |
| 6-ethoxy-1,2-dihydro-2,2,4-trimethylquinoline | 6-ethoxy-1,2-dihydro-2,2,4-trimethylquinoline |
| 6-ethoxy-1,2-dihydro-2,2,4-trimethylquinoline | ethyl maltol |
| 6-ethoxy-1,2-dihydro-2,2,4-trimethylquinoline | ethylenediaminetetraacetic acid (EDTA) |
| 6-ethoxy-1,2-dihydro-2,2,4-trimethylquinoline | *eucalyptus* extract |
| 6-ethoxy-1,2-dihydro-2,2,4-trimethylquinoline | eugenol |
| 6-ethoxy-1,2-dihydro-2,2,4-trimethylquinoline | ferulic acid |
| 6-ethoxy-1,2-dihydro-2,2,4-trimethylquinoline | a flavonoid |
| 6-ethoxy-1,2-dihydro-2,2,4-trimethylquinoline | epigallocatechin (EGC) |
| 6-ethoxy-1,2-dihydro-2,2,4-trimethylquinoline | epigallocatechin gallate (EGCG) |
| 6-ethoxy-1,2-dihydro-2,2,4-trimethylquinoline | a flavone |
| 6-ethoxy-1,2-dihydro-2,2,4-trimethylquinoline | a flavonol |
| 6-ethoxy-1,2-dihydro-2,2,4-trimethylquinoline | a flavanone |
| 6-ethoxy-1,2-dihydro-2,2,4-trimethylquinoline | fraxetin |
| 6-ethoxy-1,2-dihydro-2,2,4-trimethylquinoline | fumaric acid |
| 6-ethoxy-1,2-dihydro-2,2,4-trimethylquinoline | gallic acid |
| 6-ethoxy-1,2-dihydro-2,2,4-trimethylquinoline | gentian extract |
| 6-ethoxy-1,2-dihydro-2,2,4-trimethylquinoline | gluconic acid |
| 6-ethoxy-1,2-dihydro-2,2,4-trimethylquinoline | glycine |
| 6-ethoxy-1,2-dihydro-2,2,4-trimethylquinoline | gum guaiacum |
| 6-ethoxy-1,2-dihydro-2,2,4-trimethylquinoline | hesperetin |
| 6-ethoxy-1,2-dihydro-2,2,4-trimethylquinoline | alpha-hydroxybenzyl phosphinic acid |
| 6-ethoxy-1,2-dihydro-2,2,4-trimethylquinoline | hydroxycinammic acid |
| 6-ethoxy-1,2-dihydro-2,2,4-trimethylquinoline | hydroxyglutaric acid |
| 6-ethoxy-1,2-dihydro-2,2,4-trimethylquinoline | hydroquinone |
| 6-ethoxy-1,2-dihydro-2,2,4-trimethylquinoline | N-hydroxysuccinic acid |
| 6-ethoxy-1,2-dihydro-2,2,4-trimethylquinoline | hydroxytryrosol |
| 6-ethoxy-1,2-dihydro-2,2,4-trimethylquinoline | hydroxyurea |
| 6-ethoxy-1,2-dihydro-2,2,4-trimethylquinoline | lactic acid |
| 6-ethoxy-1,2-dihydro-2,2,4-trimethylquinoline | lactates |
| 6-ethoxy-1,2-dihydro-2,2,4-trimethylquinoline | lecithin citrate |
| 6-ethoxy-1,2-dihydro-2,2,4-trimethylquinoline | R-alpha-lipoic acid |
| 6-ethoxy-1,2-dihydro-2,2,4-trimethylquinoline | lutein |
| 6-ethoxy-1,2-dihydro-2,2,4-trimethylquinoline | lycopene |
| 6-ethoxy-1,2-dihydro-2,2,4-trimethylquinoline | malic acid |
| 6-ethoxy-1,2-dihydro-2,2,4-trimethylquinoline | malates |
| 6-ethoxy-1,2-dihydro-2,2,4-trimethylquinoline | maltol |
| 6-ethoxy-1,2-dihydro-2,2,4-trimethylquinoline | 5-methoxy tryptamine |
| 6-ethoxy-1,2-dihydro-2,2,4-trimethylquinoline | methyl gallate |
| 6-ethoxy-1,2-dihydro-2,2,4-trimethylquinoline | monoglyceride citrate |
| 6-ethoxy-1,2-dihydro-2,2,4-trimethylquinoline | monoglyceride citrate |
| 6-ethoxy-1,2-dihydro-2,2,4-trimethylquinoline | morin |
| 6-ethoxy-1,2-dihydro-2,2,4-trimethylquinoline | beta-naphthoflavone |
| 6-ethoxy-1,2-dihydro-2,2,4-trimethylquinoline | nordihydroguaiaretic acid (NDGA) |
| 6-ethoxy-1,2-dihydro-2,2,4-trimethylquinoline | octyl gallate |
| 6-ethoxy-1,2-dihydro-2,2,4-trimethylquinoline | oxalic acid |
| 6-ethoxy-1,2-dihydro-2,2,4-trimethylquinoline | an oxalate |
| 6-ethoxy-1,2-dihydro-2,2,4-trimethylquinoline | palmityl citrate |
| 6-ethoxy-1,2-dihydro-2,2,4-trimethylquinoline | phenothiazine |
| 6-ethoxy-1,2-dihydro-2,2,4-trimethylquinoline | phosphatidylcholine |
| 6-ethoxy-1,2-dihydro-2,2,4-trimethylquinoline | phosphoric acid |
| 6-ethoxy-1,2-dihydro-2,2,4-trimethylquinoline | a phosphate |
| 6-ethoxy-1,2-dihydro-2,2,4-trimethylquinoline | phytic acid |
| 6-ethoxy-1,2-dihydro-2,2,4-trimethylquinoline | phytylubichromel |
| 6-ethoxy-1,2-dihydro-2,2,4-trimethylquinoline | pimento extract |
| 6-ethoxy-1,2-dihydro-2,2,4-trimethylquinoline | a polyphosphate |
| 6-ethoxy-1,2-dihydro-2,2,4-trimethylquinoline | quercetin |
| 6-ethoxy-1,2-dihydro-2,2,4-trimethylquinoline | trans-resveratrol |

TABLE A-continued

| First Antioxidant | Second Antioxidant |
| --- | --- |
| 6-ethoxy-1,2-dihydro-2,2,4-trimethylquinoline | rice bran extract |
| 6-ethoxy-1,2-dihydro-2,2,4-trimethylquinoline | rosemary extract |
| 6-ethoxy-1,2-dihydro-2,2,4-trimethylquinoline | rosmarinic acid |
| 6-ethoxy-1,2-dihydro-2,2,4-trimethylquinoline | sage extract |
| 6-ethoxy-1,2-dihydro-2,2,4-trimethylquinoline | sesamol |
| 6-ethoxy-1,2-dihydro-2,2,4-trimethylquinoline | silymarin |
| 6-ethoxy-1,2-dihydro-2,2,4-trimethylquinoline | sinapic acid |
| 6-ethoxy-1,2-dihydro-2,2,4-trimethylquinoline | stearyl citrate |
| 6-ethoxy-1,2-dihydro-2,2,4-trimethylquinoline | succinic acid |
| 6-ethoxy-1,2-dihydro-2,2,4-trimethylquinoline | syringic acid |
| 6-ethoxy-1,2-dihydro-2,2,4-trimethylquinoline | tartaric acid |
| 6-ethoxy-1,2-dihydro-2,2,4-trimethylquinoline | tartrates |
| 6-ethoxy-1,2-dihydro-2,2,4-trimethylquinoline | thymol |
| 6-ethoxy-1,2-dihydro-2,2,4-trimethylquinoline | a tocopherol |
| 6-ethoxy-1,2-dihydro-2,2,4-trimethylquinoline | a tocotrienol |
| 6-ethoxy-1,2-dihydro-2,2,4-trimethylquinoline | tyrosol |
| 6-ethoxy-1,2-dihydro-2,2,4-trimethylquinoline | vanilic acid |
| 6-ethoxy-1,2-dihydro-2,2,4-trimethylquinoline | 2,6-di-tert-butyl-4-hydroxymethyl phenol (i.e., Ionox 100) |
| 6-ethoxy-1,2-dihydro-2,2,4-trimethylquinoline | 2,4-(tris-3',5'-bi-tert-butyl-4'-hydroxy benzyl)-mesitylene (i.e., Ionox 330) |
| 6-ethoxy-1,2-dihydro-2,2,4-trimethylquinoline | 2,4,5-trihydroxybutyrophenone |
| 6-ethoxy-1,2-dihydro-2,2,4-trimethylquinoline | ubiquinone |
| 6-ethoxy-1,2-dihydro-2,2,4-trimethylquinoline | thiodipropionic acid |
| 6-ethoxy-1,2-dihydro-2,2,4-trimethylquinoline | trihydroxy butyrophenone |
| 6-ethoxy-1,2-dihydro-2,2,4-trimethylquinoline | tryptamine |
| 6-ethoxy-1,2-dihydro-2,2,4-trimethylquinoline | tyramine |
| 6-ethoxy-1,2-dihydro-2,2,4-trimethylquinoline | uric acid |
| 6-ethoxy-1,2-dihydro-2,2,4-trimethylquinoline | vitamin K |
| 6-ethoxy-1,2-dihydro-2,2,4-trimethylquinoline | vitamin Q10 |
| 6-ethoxy-1,2-dihydro-2,2,4-trimethylquinoline | wheat germ oil |
| 6-ethoxy-1,2-dihydro-2,2,4-trimethylquinoline | zeaxanthin |
| 6-ethoxy-1,2-dihydro-2,2,4-trimethylquinoline | derivates of any of the foregoing |

In other embodiments, a combination of the invention may comprise three antioxidants. In another embodiments, a combination of the invention may comprise four antioxidants. In still further embodiments, a combination of the invention may comprise more than four antioxidants.

In one preferred embodiment, the antioxidant may be 6-ethoxy-1,2-dihydro-2,2,4-trimethylquinoline. In another preferred embodiment, the antioxidant may be 6-ethoxy-1,2-dihydro-2,2,4-trimethylquinoline in combination with any of the natural antioxidants detailed herein. In a further preferred embodiment, the antioxidant may be 6-ethoxy-1,2-dihydro-2,2,4-trimethylquinoline in combination with BHA. In still another preferred embodiment, the antioxidant may be 6-ethoxy-1,2-dihydro-2,2,4-trimethylquinoline in combination with BHT. In an exemplary embodiment, the antioxidant may be 6-ethoxy-1,2-dihydro-2,2,4-trimethylquinoline in combination with TBHQ. The combination of 6-ethoxy-1,2-dihydro-2,2,4-trimethylquinoline and TBHQ is sold under the trademark AGRADO® Plus (Novus International Inc.).

(i) Amount of Antioxidant

As will be appreciated by a skilled artisan, the concentration of the antioxidant or combination of antioxidants comprising the combination of the invention can and will vary depending upon the particular antioxidant(s), the amount and type of fat source in the feed ration, and the species and age of the animal that will be fed the combination. By way of non-limiting example, when the animal is a beef cow, the amount of active ingredient in the antioxidant or combination of antioxidants fed to the beef cow may range from about 50 to about 300 ppm, or from about 140 to about 160 ppm in its feed ration. In an exemplary embodiment, the amount of active ingredient fed to the beef cow may be about 150 ppm. By way of further example, when the animal is a dairy cow, the amount of active ingredient in the antioxidant or combination of antioxidants fed to the dairy cow may range from about 20 to about 300 ppm, or from about 55 to about 75 ppm in its feed ration. Alternatively, in an exemplary embodiment, the amount of active ingredient fed to the dairy cow may be about 65 ppm. In another embodiment, when the animal is a chicken, the amount of active ingredient in the antioxidant or combination of antioxidants fed to the chicken may range from about 25 to about 300 ppm. In yet another embodiment, when the animal is a pig, the amount of active ingredient in the antioxidant or combination of antioxidants fed to the pig may range from about 25 to about 300 ppm.

(ii) Liquid Antioxidant Compositions

The antioxidant or antioxidants of a combination of the invention, when formulated as a composition, may be a liquid composition or a dry composition. For embodiments where the combination comprises a liquid composition, the composition will typically include a solvent carrier selected from a polar solvent, a non-polar solvent, or combinations of both.

Generally speaking, a polar solvent may be used when an antioxidant in the combination is a water-soluble antioxidant. Suitable examples of polar solvents include, but are not limited to, glycerol, isopropyl alcohol, ethyl alcohol, propylene glycol, erythritol, xylitol, sorbitol, maltitol, mannitol, water, or mixtures thereof. In one embodiment the polar solvent may be glycerol. The concentration of the polar solvent will vary depending upon the antioxidant(s) in the composition. In general, the percent by volume of the polar solvent may range from about 5% to about 50%. The percent by volume of polar solvent may be about 5%, 10%, 15%, 20%, or 25%.

The liquid composition may also include a nonpolar solvent. In general, a nonpolar solvent may be used when an antioxidant in the combination is lipid-soluble. Suitable examples of nonpolar solvents include, but are not limited to, monoglycerides, diglycerides, vegetable oil, or combinations thereof. The monoglycerides and diglycerides may be distilled from vegetable oils or they may be synthesized via an esterification reaction. The vegetable oil may be corn oil, soybean oil, canola oil, cottonseed oil, palm oil, peanut oil, safflower oil, and sunflower oil. In one embodiment, the nonpolar solvent may be corn oil. In another embodiment, the nonpolar solvent may comprise monoglycerides and corn oil. The concentration of the nonpolar solvent will vary depending upon the antioxidant(s) in the composition. In general, the percent by volume of the nonpolar solvent may range from about 5% to about 50%. The percent by volume of the nonpolar solvent may be 10%, 15%, 20%, or 25%.

By way of non-limiting example, a liquid antioxidant composition may comprise from about 40% to about 75% by weight of 6-ethoxy-1,2-dihydro-2,2,4-trimethylquinoline, from about 1% to about 20% by weight of tertiary butyl hydroquinone, and from about 10% to about 30% by weight of at least one solvent carrier. In another embodiment, the liquid composition may comprise from about 60% to about 70% by weight of 6-ethoxy-1,2-dihydro-2,2,4-trimethylquinoline, from about 1% to about 10% by weight of tertiary butyl hydroquinone, and from about 10% to about 30% by weight of at least one solvent carrier. In an exemplary embodiment, the liquid composition consists of about 65% by weight 6-ethoxy-1,2-dihydro-2,2,4-trimethylquinoline, about 7% by weight tertiary butyl hydroquinone, about 7% by weight citric acid, about 19% by weight propylene glycol, and about 2% by weight corn oil.

(iii) Dry Antioxidant Compositions

Alternatively, the antioxidant or antioxidants may be formulated as a dry composition. Typically, when formulated as a dry composition, one or more carriers may be utilized. In an exemplary embodiment, the dry composition will be flowable. In this context, "flowable" means that the dry composition is substantially free flowing and substantially resistant to clumping.

Several inorganic carriers are suitable for formulating a dry composition of the antioxidant or antioxidants. The inorganic carrier will typically be granular, it may be porous, and is generally biologically inert. In this context, an inorganic carrier is biologically inert if it is nontoxic and does not generate an appreciable immune reaction when administered to an animal. Non-limiting examples of suitable inorganic carriers include natural or regenerated mineral substrates. One preferred class of mineral carriers is the silicate class. The silicate may be selected from a silicate subclass selected from the group consisting of nesosilicate, sorosilicate, inosilicate, cyclosilicate, phyllosilicate and tectosilicate. Examples of suitable nesosilicates include aluminum silicate, iron magnesium manganese aluminum silicate hydroxide, calcium borosilicate hydroxide, beryllium aluminum silicate hydroxide, iron silicate, magnesium silicate, yttrium iron beryllium silicate, iron aluminum silicate, calcium iron silicate, calcium aluminum silicate, magnesium aluminum silicate, calcium chromium silicate, calcium boro-silicate hydroxide, aluminum silicate, magnesium iron silicate, berylium silicate, calcium titanium silicate, zinc silicate and zirconium silicate. Suitable examples of sorosilicates include beryllium silicate hydroxide, calcium boro-silicate, yttrium cerium calcium aluminum iron silicate hydroxide, calcium aluminum silicate hydroxide, calcium iron aluminum silicate hydroxide, calcium aluminum silicate hydroxide, and calcium iron silicate hydroxide. Non-limiting examples of suitable inosilicates include sodium titanium silicate, calcium silicate, sodium iron silicate, calcium sodium magnesium aluminum iron titanium silicate, calcium magnesium silicate, magnesium silicate, calcium iron silicate, magnesium iron silicate, sodium aluminum iron silicate, lithium aluminum silicate, manganese iron magnesium calcium silicate, sodium manganese calcium silicate hydroxide, copper silicate hydroxide, calcium silicate, calcium magnesium iron silicate hydroxide, magnesium iron silicate hydroxide, iron magnesium silicate hydroxide, potassium iron titanium silicate hydroxide, and calcium iron manganese silicate hydroxide. Suitable examples of cyclosilicates include calcium magnesium iron manganese aluminum borosilicate, potassium lithium calcium titanium zirconium silicate, barium titanium silicate, beryllium aluminum silicate, magnesium aluminum silicate, potassium sodium iron magnesium aluminum silicate, sodium magnesium aluminum boro-silicate hydroxide, and potassium sodium lithium iron manganese aluminum silicate. Examples of suitable phyllosilicates include hydrated potassium sodium calcium silicate, hydrated calcium vanadium silicate, hydrated copper aluminum hydrogen silicate hydroxide, iron magnesium aluminum silicate hydroxide, iron magnesium aluminum silicate hydroxide, lithium aluminum silicate hydroxide, aluminum silicate hydroxide, magnesium silicate hydroxide, hydrated calcium silicate hydroxide, potassium iron magnesium aluminum silicate hydroxide fluoride, potassium lithium aluminum silicate hydroxide fluoride, potassium aluminum silicate hydroxide fluoride, potassium magnesium aluminum silicate hydroxide fluoride, calcium aluminum silicate hydroxide, and iron magnesium silicate hydroxide. Suitable examples of tectosilicates include sodium aluminum silicate, sodium calcium aluminum silicate, calcium aluminum silicate, calcium sodium aluminum silicate, sodium calcium aluminum silicate, potassium aluminum silicate, sodium calcium silicate, silicon dioxide, sodium calcium aluminum silicate carbonate, sodium calcium aluminum silicate sulfate sulfide chloride, sodium aluminum silicate chloride, calcium sodium aluminum silicate chloride carbonate sulfate, hydrated sodium aluminum silicate, hydrated calcium aluminum silicate, hydrated barium potassium aluminum silicate, and hydrated sodium calcium aluminum silicate. In a preferred embodiment, the inorganic substrate is silicon dioxide or sodium benetonite. Depending upon the embodiment, the inorganic carrier may be a mixture of compounds, such as a mixture of one or more of any of the aforementioned silicates.

It will be appreciated by those of skill in the art that the particle size of the inorganic carrier as well as the concentration of inorganic carrier can and will vary. In general, the average particle size of inorganic carrier may be from about 50 microns to about 1000 microns. In another embodiment, the average particle size of the inorganic carrier may be from about 100 microns to about 500 microns. In yet another embodiment, the average particle size of the inorganic carrier may be from about 100 microns to about 200 microns. In another embodiment, the concentration of inorganic carrier included in the dry composition may be from about 0.1% to about 0.5% by weight DM of the dry composition. In still another embodiment, the concentration of inorganic carrier included in the dry composition may be from about 1.0% to about 5.0% by weight DM of the dry composition. In yet another embodiment, the concentration of inorganic carrier included in the dry composition may be from about 2.5% to about 15.0% by weight DM of the dry composition.

By way of non limiting example, a dry composition of the antioxidant or antioxidants may comprise from about 30% to about 70% by weight DM of 6-ethoxy-1,2-dihydro-2,2,4-trimethylquinoline, from about 1% to about 10% by weight DM of tertiary butyl hydroquinone, and from about 0.1% to about 15% by weight DM of a carrier. In another embodiment, the dry composition may comprise from about 45% to about 55% by weight DM of 6-ethoxy-1,2-dihydro-2,2,4-trimethylquinoline, from about 3% to about 7% by weight DM of tertiary butyl hydroquinone, and from about 0.1% to about 15% by weight DM of a carrier. In an exemplary embodiment, the dry composition consists of about 50% by weight dm of 6-ethoxy-1,2-dihydro-2,2,4-trimethylquinoline, about 5% by weight DM of tertiary butyl hydroquinone, about 5% by weight DM of citric acid, and about 10% by weight DM of calcium carbonate.

(b) Trace Minerals

In some embodiments, the combinations of the invention may also comprise one or more trace minerals. The trace minerals may include organic trace minerals, inorganic trace minerals, or a combination of organic and inorganic trace minerals. Suitable non-limiting examples of trace minerals are described below.

(i) Organic Trace Minerals

A variety of suitable organic forms of trace minerals may be used in the combinations of the invention. When the organic trace mineral comprises selenium, it is preferably selenium yeast or selenium methionine. Other suitable organic trace minerals are described below.

In one exemplary embodiment, the organic trace mineral may comprise a metal chelate comprising metal ions and an amino acid ligand. Alternatively, the organic trace mineral may be a metal salt comprising metal ions and an amino acid anion. The metal ions may be selected from the group consisting of zinc ions, copper ions, manganese ions, iron ions, chromium ions, cobalt ions, magnesium ions, calcium ions, and combinations thereof. In a preferred embodiment, the metal ions are zinc ions, manganese ions, and copper ions. The amino acids may be selected from the group comprising alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, or their hydroxy analogs. In certain embodiments, the copper and zinc ions are preferably divalent, i.e., each ion carries a charge of $2^+$. The molar ratio of amino acids to metal ions in the chelate molecule may generally vary from 1:1 to 3:1 or higher. Typically, a metal chelate may comprise a mixture of 1:1, 2:1 and 3:1 species. Preferably, the molar ratio of amino acids to metal ion in the chelate molecule may generally vary from 1.5:1 to 2.5:1. In an aqueous medium, the relative proportions of these species are determined by the applicable stability constants.

Where the number of ligands equates to the charge on the metal ion, the charge is typically balanced because the carboxyl moieties of the amino acids are in deprotonated form. For example, in the chelate species wherein the metal cation carries a charge of $2^+$ and the amino acid to metal ratio is 2:1, each of the hydroxy or amino groups is understood to be bound by a coordinate covalent bond to the metal ion. Where the number of ligands exceeds the charge on the metal ion, e.g., in a 3:1 chelate of a divalent metal ion, the amino acids in excess of the charge typically may remain in a protonated state to balance the charge. On the other hand, where the positive charge on the metal ion exceeds the number of amino acids, the charge may be balanced by the presence of another anion such as, for example, chloride, bromide, iodide, bicarbonate, hydrogen sulfate, dihydrogen phosphate and combinations thereof. Divalent anions may also be present.

In an exemplary embodiment, the metal chelate comprises metal ions and ligands, wherein a compound comprising Formula (III) is a source of the ligands. The metal salt comprises metal ions and anions, wherein a compound comprising Formula (III) is a source of the anions. The compound comprising Formula (III) has the structure:

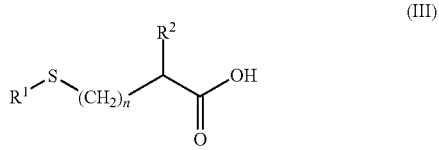

(III)

wherein:
$R^1$ is selected from the group consisting of methyl and ethyl;
$R^2$ is selected from the group consisting of hydroxy and amino; and
n is an integer from 0 to 2.

In various preferred embodiments of the present invention, the compound comprising Formula (III) comprises 2-hydroxy-4-methylthiobutanoic acid, i.e., n is 2, $R^1$ is methyl, and $R^2$ is hydroxy. 2-Hydroxy-4-methylthiobutanoic acid is commonly known as "HMTBA" and sold by Novus International Inc. under the trade name ALIMET®.

Preferably, the metal ions are selected from the group consisting of zinc ions, copper ions, manganese ions, magnesium ions, iron ions, chromium ions, cobalt ions, calcium ions and combinations thereof. Where the metal ion is copper or manganese, it is preferably divalent, i.e., it carries a charge of $2^+$. Zn cations are essentially universally divalent. In other metal chelates useful in the compositions and methods of the invention, the metal ions are also preferably divalent.

The ratio of ligands to metal ion in the chelate molecule may generally vary from 1:1 to 3:1 or higher. Typically, a metal chelate may comprise a mixture of 1:1, 2:1 and 3:1 species. Preferably, the ratio of ligands to metal ion in the chelate molecule may generally vary from 1.5:1 to 2.5:1. In an aqueous medium, the relative proportions of these species are determined by the applicable stability constants. In the case where the compound comprising Formula (III) is methionine, i.e., n is 2, $R^2$ is amino, and $R^1$ is methyl, a number of the stability constants are available from the literature. At least some stability constants may also be available for the chelates in which the compound comprising Formula (III) is HMTBA, i.e., n is 2, $R^2$ is hydroxy, and $R^1$ is methyl.

Where the number of ligands equates to the charge on the metal ion, the charge is typically balanced because the carboxyl moieties of the ligands are in deprotonated form. Thus, in these chelates, each of the ligands comprises Formula (IIIA):

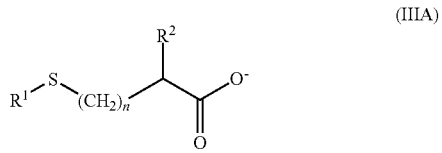

(IIIA)

wherein $R^1$, $R^2$, and n are defined above, i.e., the chelate in this respect is also a dicarboxylate salt. For example, in the chelate species wherein the metal cation carries a charge of $2^+$ and the ligand to metal ratio is 2:1, each of the hydroxy or amino group ($R^2$) groups is understood to be bound by a coordinate covalent bond to the metal ion. Typical examples are the complexes of $Zn^{2+}$, $Cu^{2+}$, $Mn^{2+}$ with two 2-hydroxy-4-methylthiobutanoate ions. Where the number of ligands exceeds the charge on the metal ion, e.g., in a 3:1 chelate of a divalent metal ion, the ligands in excess of the charge typically may remain in a protonated state to balance the charge. On the other hand, where the positive charge on the metal ion exceeds the number of ligands, the charge may be balanced by the presence of another anion such as, for example, chloride, bromide, iodide, bicarbonate, hydrogen sulfate, dihydrogen phosphate and combinations thereof. Divalent anions may also be present.

In an exemplary embodiment, the organic trace mineral comprises a metal chelate or a metal salt comprising zinc, manganese, and/or copper ions and HMTBA.

(ii) Inorganic Trace Minerals

The trace mineral may also be an inorganic trace mineral. Suitable inorganic trace minerals include, for example, metal sulfates, metal oxides, metal carbonates, and metal halides. By way of non-limiting example, the inorganic trace mineral may be copper sulfate, copper oxide, copper chloride, or copper carbonate. Alternatively, the inorganic trace mineral may be manganese sulfate, manganese chloride, or manganous oxide. In another embodiment, the inorganic trace mineral may be zinc sulfate, zinc oxide, zinc chloride, or zinc carbonate. In yet an additional embodiment, the inorganic trace mineral may be sodium selenite or sodium selenate.

(iii) Amount of Trace Mineral

Generally speaking, the amount of trace mineral provided to the animal in the combination can and will vary from species to species and also within a species. Typically, however, the amount provided will range from about 10% to about 1000% of the daily trace mineral requirement for the animal. In another embodiment, the amount provided will range from about 20% to about 500% of the daily trace mineral requirement for the animal. In an additional embodiment, the amount provided will range from about 30% to about 200% of the daily trace mineral requirement for the animal.

Trace mineral requirements for various animals are well known in the art, such as, for example the National Research Council for poultry (1994), dairy (2001), beef (2000), and swine (1998). For example, cattle typically require from about 5 to about 300 mg/kg of ration DM of copper daily, from about 10 to about 600 mg/kg of ration DM of manganese daily, from about 20 to about 900 mg/kg of ration DM of zinc daily, and from about 0.1 to about 2 mg/kg of ration DM of selenium daily. Poultry generally require from about 1 to about 300 mg/kg of ration DM of copper daily, from about 20 to about 100 mg/kg of ration DM of manganese daily, from about 30 to about 1500 mg/kg of ration DM of zinc daily, and from about 0.1 to about 2 mg/kg of ration DM of selenium daily. By way of further example, swine generally require from about 8 to about 500 mg/kg of ration DM of copper daily, from about 2 to about 70 mg/kg of ration DM of manganese daily, from about 10 to about 4000 mg/kg of ration DM of zinc daily, and from about 0.1 to about 2 mg/kg of ration DM of selenium daily.

It is envisioned that the trace mineral may be provided to the animal as a liquid or a solid. In some cases when it is provided as a solid, the particle size of the trace mineral is important. For example, a smaller particle size generally increases the bioavailability of the trace mineral. In various embodiments of the present invention, the mean particle size of the trace mineral is from about 100 microns to about 1400 microns.

(c) Hydroxy Analog of Methionine

In various embodiments, the combinations of the invention may also comprise a hydroxy analog of methionine. In one embodiment, the hydroxy analog of methionine is a compound comprising Formula (IV):

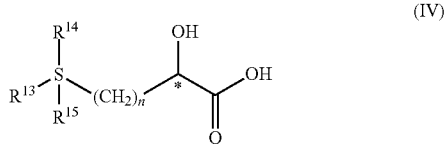

(IV)

wherein:
* is a chiral carbon;
$R^{13}$ is methyl or ethyl;
$R^{14}$ and $R^{15}$ are independently oxygen or hydrogen; and
n is an integer from 0 to 4.

Compounds comprising Formula (IV) may be a methionine sulfoxide hydroxy analog (i.e., when one of $R^{14}$ or $R^{15}$ is hydrogen and one is oxygen) or a methionine sulfone hydroxy analog (i.e., when $R^{14}$ and $R^{15}$ are oxygen). The compound comprising Formula (IV) may be normethionine (i.e., n is 1), methionine (i.e., n is 2) or homomethionine (i.e., n is 3). In an exemplary embodiment, the compound comprising Formula (IV) is methionine. The compound comprising Formula (IV) may also be an ester derivative. Examples of suitable ester derivatives include methyl, ethyl, propyl, isopropyl, and butyl esters. For each embodiment with compounds comprising Formula (IV), both the $_D$- and $_L$-isomers are included within the scope of the invention. The invention also encompasses pharmaceutically acceptable salts of compounds comprising Formula (IV). Suitable examples of salts include ammonium salt, alkaline earth metal salts (e.g., magnesium and calcium), alkali metal salts (e.g., lithium, sodium, and potassium), copper salts, zinc salts, cobalt salts, chromium salts, selenium salts, manganese salts, and iron salts.

In a further exemplary embodiment, the hydroxy analog of methionine comprises Formula (V):

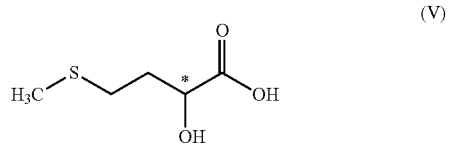

(V)

The compound comprising Formula (V) is 2-hydroxy-4 (methylthio)butanoic acid or HMTBA. A variety of HMTBA salts, chelates, esters, amides, and oligomers are also suitable for use in the invention. Representative salts of HMTBA, in addition to the ones described below, include the ammonium salt, the stoichiometric and hyperstoichiometric alkaline earth metal salts (e.g., magnesium and calcium), the stoichiometric and hyperstoichiometric alkali metal salts (e.g., lithium, sodium, and potassium), and the stoichiometric and hyperstoichiometric zinc salt. Representative esters of HMTBA include the methyl, ethyl, 2-propyl, butyl, and 3-methylbutyl esters of HMTBA. Representative amides of HMTBA include methylamide, dimethylamide, ethylmethylamide, butylamide, dibutylamide, and butylmethylamide. Representative oligomers of HMTBA include its dimers, trimers, tetramers and oligomers that include a greater number of repeating units.

In one exemplary embodiment, the hydroxy analog of methionine is a calcium salt of the compound comprising Formula (V). This compound is also known as MHA or MFP® (which is available from Novus International Inc.). Methods for preparing MHA or MFP® are well known and set forth in U.S. Pat. No. 2,745,745, which is incorporated herein by reference in its entirety. Generally speaking, poultry and swine generally require from 0.01 to about 0.4% of HMTBA or MHA/MFP® daily; and dairy and beef cattle generally require from 1 to 40 grams of HMTBA or MHA/MFP® per day.

(d) Organic Acids

In still other embodiments of the invention, the combinations may also comprise at least one organic acid. The organic acid may be a hydroxy analog of methionine as described in section (I)(c). Alternatively, the organic acid may be other than a hydroxy analog of methionine. A variety of suitable organic acids may be utilized in the compositions of the invention. Typically, the organic acid will be a carboxylic acid or a substituted carboxylic acid having acidic properties. In an exemplary embodiment, the organic acid may also provide antimicrobial activity. The organic acid may be a monocarboxylic acid, a dicarboxylic acid, or a tricarboxylic acid; it may be have a straight chain, be branched, or be cyclic; and it may be saturated or unsaturated.

A variety of organic acids comprised of carboxylic acids are suitable. In one embodiment, the organic acid may contain from about one to about twenty-five carbon atoms. In another embodiment, the organic acid may have from about three to about twenty-two carbon atoms. In a further embodiment, the organic acid may contain from about three to about twelve carbon atoms. In yet another embodiment, the organic acid may contain from about eight to about twelve carbon atoms. In still another embodiment, the organic acid may contain from about two to about six carbon atoms. Suitable organic acids, by way of non-limiting example, include formic acid, acetic acid, propionic acid, butanoic acid, benzoic acid, lactic acid, malic acid, tartaric acid, mandelic acid, citric acid, fumaric acid, sorbic acid, boric acid, succinic acid, adipic acid, glycolic acid, cinnamaldehyde, and glutaric acid.

Salts of organic acids comprising carboxylic acids are also suitable for certain embodiments. Representative suitable salts include the ammonium, magnesium, calcium, lithium, sodium, potassium, selenium, iron, copper, and zinc salts of organic acids. In one embodiment, the organic acid is an ammonium, magnesium, calcium, lithium, sodium, potassium, selenium, iron, copper, or zinc salt of formic acid. In another embodiment, the organic acid is an ammonium, magnesium, calcium, lithium, sodium, potassium, selenium, iron, copper, or zinc salt of acetic acid. In yet another embodiment, the organic acid is an ammonium, magnesium, calcium, lithium, sodium, potassium, selenium, iron, copper, or zinc salt of propionic acid. In an additional embodiment, the organic acid is an ammonium, magnesium, calcium, lithium, sodium, potassium, selenium, iron, copper, or zinc salt of butanoic acid. In a further embodiment, the organic acid is an ammonium, magnesium, calcium, lithium, sodium, potassium, selenium, iron, copper, or zinc salt of benzoic acid. In still another embodiment, the organic acid is an ammonium, magnesium, calcium, lithium, sodium, potassium, selenium, iron, copper, or zinc salt of lactic acid. In yet another embodiment, the organic acid is an ammonium, magnesium, calcium, lithium, sodium, potassium, selenium, iron, copper, or zinc salt of malic acid. In still another embodiment, the organic acid is an ammonium, magnesium, calcium, lithium, sodium, potassium, selenium, iron, copper, or zinc salt of tartaric acid. In a further embodiment, the organic acid is an ammonium, magnesium, calcium, lithium, sodium, potassium, selenium, iron, copper, or zinc salt of mandelic acid. In yet another embodiment, the organic acid is an ammonium, magnesium, calcium, lithium, sodium, potassium, selenium, iron, copper, or zinc salt of citric acid. In an additional embodiment, the organic acid is an ammonium, magnesium, calcium, lithium, sodium, potassium, selenium, iron, copper, or zinc salt of fumaric acid. In an additional embodiment, the organic acid is an ammonium, magnesium, calcium, lithium, sodium, potassium, selenium, iron, copper, or zinc salt of sorbic acid. In another embodiment, the organic acid is an ammonium, magnesium, calcium, lithium, sodium, potassium, selenium, iron, copper, or zinc salt of boric acid. In yet another embodiment, the organic acid is an ammonium, magnesium, calcium, lithium, sodium, potassium, selenium, iron, copper, or zinc salt of succinic acid. In another embodiment, the organic acid is an ammonium, magnesium, calcium, lithium, sodium, potassium, selenium, iron, copper, or zinc salt of adipic acid. In yet another embodiment, the organic acid is an ammonium, magnesium, calcium, lithium, sodium, potassium, selenium, iron, copper, or zinc salt of glycolic acid. In an additional embodiment, the organic acid is an ammonium, magnesium, calcium, lithium, sodium, potassium, selenium, iron, copper, or zinc salt of glutaric acid.

Alternatively, the organic acid may be comprised of a substituted carboxylic acid. A substituted carboxylic acid generally has the same features as those detailed above for carboxylic acids, but the hydrocarbyl chain has been modified such that it is branched, is part of a ring structure, or contains some other substitution. In one embodiment, the substituted carboxylic acid may contain one or more additional carboxyl groups. Saturated dicarboxylic acids include malonic acid, succinic acid, glutaric acid, and adipic acid, and unsaturated dicarboxylic acids include maleic acid and fumaric acid. In another embodiment, the substituted carboxylic acid may contain one or more hydroxy groups. A substituted carboxylic acid with a hydroxy group on the alpha carbon, i.e., the carbon adjacent to the carboxyl carbon, is generally called a α-hydroxy carboxylic acid. Examples of suitable α-hydroxy carboxylic acids include glycolic acid, lactic acid, malic acid, and tartaric acid. In an alternate embodiment, the substituted carboxylic acid may contain one or more carbonyl groups. In yet another embodiment, the substituted carboxylic acid may contain an amino group on the alpha carbon, i.e., is an α-amino acid. In one embodiment, the α-amino acid may be one of the twenty standard amino acids or derivatives thereof. In another embodiment, the α-amino acid may be an essential α-amino acid selected from the group consisting of arginine, histidine, isoleucine, leucine, lysine, methionine, phenylalanine, threonine, tryptophan, and valine. Salts of organic acids comprising substituted carboxylic acids are also suitable for certain embodiments. Representative suitable salts include the ammonium, magnesium, calcium, lithium, sodium, potassium, selenium, iron, copper, and zinc salts of organic acids comprising substituted carboxylic acids. Generally speaking, poultry and swine generally required from about 0.1% to about 2.0% of organic acids in their diets and dairy and beef cattle required from about 0.15% to about 2.0% of organic acids in their diets.

In preferred embodiments, the organic acid may be formic acid, acetic acid, propionic acid, butanoic acid, benzoic acid, lactic acid, malic acid, tartaric acid, mandelic acid, citric acid, fumaric acid, sorbic acid, boric acid, succinic acid, adipic acid, glycolic acid, glutaric acid, 2-hydroxy-4-methylthiobutanoic acid, or a mixture thereof. In an exemplary embodiment, the organic acid comprises a mixture of benzoic acid, fumaric acid, and HMTBA.

(e) Mycotoxin Binders

Optionally, in certain embodiments, the combination may include at least one mycotoxin binder. In the context of the present invention a "mycotoxin binder" is an agent that diminishes the negative affects of mycotoxins by binding them into inactive or unavailable forms.

In one embodiment, the mycotoxin binder is mineral clay. Suitable mineral clays include bentonite, sepiolite, palygorskite, hydrated sodium calcium aluminosilicate, hydrated sodium calcium aluminophosphate, phyllosilicate, zeolite, montmorillonite (acid-activated calcium bentonite), calcined atapulgite, smectite, vermiculite, illite, and atapulgite. In a preferred embodiment, the mineral clay is hydrated sodium calcium aluminosilicate.

Alternatively, the mycotoxin binder may include whole yeast cells or yeast cell extracts. The yeast organism may be any of a number of edible yeasts including, but not limited to, *Saccharomyces, Candida, Kluyveromnyces,* or *Torulaspora* species. In an exemplary embodiment, the yeast used is *Saccharomyces cerevisiae*. In one exemplary embodiment, the yeast extract is a cell wall extract that comprises the mannan oligosaccharide (MOS) portion of the cell wall. Suitable MOS products are known in the art (e.g., FERMOS®, by Micron Bio-Systems, Inc.).

In another embodiment, the mycotoxin binder may comprise a mixture of one or more mineral clays and yeast (e.g., whole yeast or yeast cell extract). For example, suitable mycotoxin binders that include these agents are sold under the trade names SOLIS® PRO, SOLIS® MOS, MYCOTEX®, ULTRASORB® (by Novus International, Inc.), and under the trade name MTB100® (by Alltech, Inc). The general range of mycotoxin binders included in swine, poultry and ruminants is from about 0.05 to 0.5% in the diet.

(f) Immune Stimulating Agent

In additional embodiments, the combinations of the invention may also comprise at least one immune stimulating agent. As used herein, an "immune stimulating agent" is an agent that can stimulate immune function of the animal by a variety of mechanisms, such as by improving the animal's physiological defenses.

Suitable immune stimulating agents include minerals, vitamins, probiotics, and prebiotics. Exemplary vitamins and minerals include those that enhance immune function such as Vitamin E, Vitamin D, zinc, copper, and selenium.

Probiotics and prebiotics include yeast and bacteria that help establish an immune protective rumen or gut microflora as well as small oligosaccharides. By way of non-limiting example, yeast-derived probiotics and prebiotics include yeast cell wall derived components such as β-glucans, arabinoxylan isomaltose, agarooligosaccharides, lactosucrose, cyclodextrins, lactose, fructooligosaccharides, laminariheptaose, lactulose, β-galactooligosaccharides, mannanoligosaccharides, raffinose, stachyose, oligofructose, glucosyl sucrose, sucrose thermal oligosaccharide, isomalturose, caramel, inulin, and xylooligosaccharides. In an exemplary embodiment, the yeast-derived agent may be β-glucans and/or mannanoligosaccharides. Sources for yeast cell wall derived components include *Saccharomyces bisporus, Saccharomyces boulardii, Saccharomyces cerevisiae, Saccharomyces capsularis, Saccharomyces delbrueckii, Saccharomyces fermentati, Saccharomyces lugwigii, Saccharomyces microellipsoides, Saccharomyces pastorianus, Saccharomyces rosei, Candida albicans, Candida cloaceae, Candida tropicalis, Candida utilis, Geotrichum candidum, Hansenula americana, Hansenula anomala, Hansenula wingei,* and *Aspergillus oryzae.*

Probiotics and prebiotics also include bacteria cell wall derived agents such as peptidoglycan and other components derived from gram-positive bacteria with a high content of peptidoglycan. Exemplary gram-positive bacteria include *Lactobacillus acidophilus, Bifedobact thermophilum, Bifedobat longhum, Streptococcus faecium, Bacillus pumilus, Bacillus subtilis, Bacillus licheniformis, Lactobacillus acidophilus, Lactobacillus casei, Enterococcus faecium, Bifidobacterium bifidium, Propionibacterium acidipropionici, Propionibacteriium freudenreichii,* and *Bifidobacterium pscudolongum.*

(g) Tissue Regenerating Agent

In certain other embodiments, a combination of the invention may further comprise at least one tissue regenerating agent. Exemplary tissue regeneration agents generally include esters of polyols. Suitable polyols typically have at least one accessible hydroxyl group. In this context, the term "accessible" means the hydroxyl group of the polyol is capable of forming an ester bond with a compound containing a carboxyl group. More typically, the polyol may have three or more hydroxyl groups. A suitable polyol having three hydroxyl groups is glycerol. In other embodiments, the polyol may be a sugar alcohol having four to six hydroxyl groups. Examples of suitable sugar alcohols include erythritol, xylitol, sorbitol, maltitol and mannitol. In an alternative embodiment, the polyol may be an oligosaccharide or polysaccharide having at least one accessible hydroxyl group. Inulin is an example of a suitable oligosaccharide.

In an exemplary embodiment, the tissue regenerating agent is a polyol ester compound comprising Formula (VI):

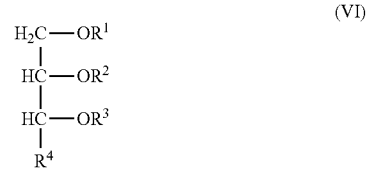

wherein:
$R^1$, $R^2$, and $R^3$ are independently selected from the group consisting of hydrogen, an amino acid, and a carboxylic acid or a substituted carboxylic acid having from two to twenty-two carbon atoms;
$R^4$ is hydrogen or $(CH_2OR^5)_m$;
m is an integer from 1 to 3; and
$R^5$ is independently selected from the group consisting of hydrogen, an amino acid, and a carboxylic acid or a substituted carboxylic acid having from two to twenty-two carbon atoms.

For each of the foregoing embodiments for polyol esters comprising Formula (VI), $R^4$ may be hydrogen. Alternatively, $R^4$ may be $(CH_2OR^5)_m$. In certain embodiments, m is one. In other embodiments, m is two. In additional embodiments, m is three.

In yet another alternative exemplary embodiment, the polyol ester is a glycerol ester comprising Formula (VII):

wherein:
$R^1$, $R^2$, and $R^3$ are independently selected from the group consisting of hydrogen, a carboxylic acid or substituted carboxylic acid having from two to twenty-two carbon atoms, and an amino acid For any of the above-embodiments, the carboxylic acid compound may be a monocarboxylic acid having a straight chain or it may be branched; it may be saturated or unsaturated. In one embodiment, the carboxylic acid may contain from about two to about twenty-five carbon atoms. In another embodiment, the carboxylic acid may have from about three to about twenty-two carbon atoms. In a further embodiment, the carboxylic acid may contain from about three to about twelve carbon atoms. In yet another embodiment, the carboxylic acid may contain from about eight to about twelve carbon atoms. In still another embodiment, the carboxylic acid may contain from about two to about six carbon atoms. By way of non limiting example, the carboxylic acid may be a saturated aliphatic compound selected from the group consisting of propionic acid, butanoic acid, pentanoic acid, caproic or hexanoic acid, heptanoic acid, caprylic or octanoic acid, nonanoic acid, capric or decanoic acid, undecanoic acid, lauric or dodecanoic acid, tridecanoic acid, myristic or tetradecanoic acid, pentadecanoic acid, palmitic or hexadecanoic acid, margaric or heptadecanoic acid, stearic or octadecanoic acid, nonadecanoic acid, arachidic or eicosanoic acid, and behenic or docosanoic acid. Alternatively, the carboxylic acid may be an unsaturated aliphatic compound selected from the group consisting of sorbic acid, a hexanoic acid with two double bonds (6:2), myristoleic acid (i.e., a $C_{14}$ acid with one double bond (14:1)), palmitoleic acid (16:1), oleic acid (18:1), linoleic acid (18:2), linolenic (18:3), gadoleic acid (20:1), and arachidonic acid (20:4).

Alternatively, the carboxylic acid compound may be a substituted carboxylic acid. A substituted carboxylic acid generally has the same features as those detailed above for carboxylic acids, but the hydrocarbyl chain has been modified such that it is branched, is part of a ring structure, or contains some other substitution. In one embodiment, the substituted carboxylic acid may contain one or more additional carboxyl groups. Saturated dicarboxylic acids include malonic acid, succinic acid, glutaric acid, and adipic acid, and unsaturated dicarboxylic acids include maleic acid and fumaric acid. In another embodiment, the substituted carboxylic acid may contain one or more hydroxyl groups. A substituted carboxylic acid with a hydroxyl group on the alpha carbon, i.e., the carbon adjacent to the carboxyl carbon, is generally called a α-hydroxy carboxylic acid. Examples of suitable α-hydroxy carboxylic acids include glycolic acid, lactic acid, malic acid, and tartaric acid. In an alternate embodiment, the substituted carboxylic acid may contain one or more carbonyl groups. In yet another embodiment, the substituted carboxylic acid may contain an amino group on the alpha carbon, i.e., is an α-amino acid. In one embodiment, the α-amino acid may be one of the twenty standard amino acids or derivatives thereof. In another embodiment, the α-amino acid may be an essential α-amino acid selected from the group consisting of arginine, histidine, isoleucine, leucine, lysine, methionine, phenylalanine, threonine, tryptophan, and valine.

In yet another embodiment, the substituted carboxylic acid may be a compound having Formula (VIII):

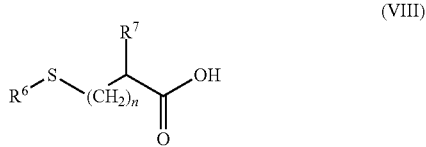

(VIII)

wherein:
n is an integer from 0 to 2;
$R^6$ is an alkyl group having from one to four carbon atoms;
$R^7$ is selected from the group consisting of hydroxyl, amino, and —$OCOR^8$ or —$NHCOR^8$; and
$R^8$ is an organic acid derivative.

In preferred embodiments for compounds having Formula (VIII), $R^6$ is methyl or ethyl; $R^7$ is hydroxyl or amino; and n is 0 to 2.

In an exemplary embodiment, the tissue regeneration agent is a mono, di, or tri-ester of glycerol. Exemplary esters of glycerol include those having propanoic acid, butanoic acid, pentanoic acid, caproic or hexanoic acid, heptanoic acid, caprylic or octanoic acid, nonanoic acid, capric or decanoic acid, and 2-hydroxy-4-methylthiobutanoic acid.

(h) Additional Ingredients

The combinations may be provided to the animal in the form of a feed premix or feed supplement. The premix will generally be added to various formulations of grain concentrates and forages to formulate a total animal feed ration. As will be appreciated by the skilled artisan, the particular premix formulation can and will vary depending upon the feed ration and animal that the feed ration will be fed to. In addition to combinations of the invention, the premix may further optionally include one or more of a mixture of natural amino acids, analogs of natural amino acids, vitamins and derivatives thereof, enzymes, animal drugs, hormones, effective microorganisms, preservatives, and flavors.

In one embodiment, the feed premix may include one or more amino acids. Suitable examples of amino acids, depending upon the formulation, include alanine, arginine, asparagines, aspartate, cysteine, glutamate, glutamine, glycine, histidine, isoleucine, leucine, lysine, methionine, phenylalanine, proline, serine, threonine, tryptophan, tyrosine, and valine. Other amino acids usable as feed additives include, by way of non-limiting example, N-acylamino acids, hydroxy homologue compounds, and physiologically acceptable salts thereof, such as hydrochlorides, hydrosulfates, ammonium salts, potassium salts, calcium salts, magnesium salts and sodium salts of amino acids.

In still another embodiment, the feed premix will include vitamins or derivatives of vitamins. Examples of suitable vitamins and derivatives thereof include vitamin A, vitamin A palmitate, vitamin A acetate, β-carotene, vitamin D (e.g., $D_2$, $D_3$, and $D_4$), vitamin E, menadione sodium bisulfite, vitamin B (e.g., thiamin, thiamin hydrochloride, riboflavin, nicotinic acid, nicotinic amide, calcium pantothenate, pantothenate choline, pyridoxine hydrochloride, cyanocobalamin, biotin, folic acid, p-aminobenzoic acid), vitamin K, vitamin Q, vitamin F, and vitamin C.

In yet another embodiment, the feed premix will include one or more enzymes. Suitable examples of enzymes include protease, amylase, lipase, cellulase, xylanase, pectinase, phytase, hemicellulase and other physiologically effective enzymes.

In still another embodiment, the feed premix will include a drug approved for use in animals. Non-limiting examples of suitable animal drugs include antibiotics such as tetracycline type (e.g., chlortetracycline and oxytetracycline), amino sugar type, ionophores (e.g., rumensin, virginiamycin, and bambermycin) and macrolide type antibiotics.

In an additional embodiment, the feed premix will include a hormone. Suitable hormones include estrogen, stilbestrol, hexestrol, tyroprotein, glucocorticoids, insulin, glucagon, gastrin, calcitonin, somatotropin, and goitradien.

In an additional embodiment, the feed premix will include a substance to increase the palatability of the feed ration. Suitable examples of such substances include natural sweeteners, such as molasses, and artificial sweeteners such as saccharin and aspartame.

As will be appreciated by the skilled artisan, any of the substances that may be included in the premix of the invention can be used alone or in combination with one another. The concentration of these additives will depend upon the application but, in general, will be between about 0.0001% and about 10% by weight of the dry matter, more preferably between about 0.001% and about 7.5%, most preferably between about 0.01% and about 5%.

(i) Exemplary Combinations

In a preferred embodiment, a combination of the invention comprises 1) at least one antioxidant selected from the group consisting of 6-ethoxy-1,2-dihydro-2,2,4-trimethylquinoline, tertiary butyl hydroquinone, butylated hydroxyanisole, and butylated hydroxytoluene; 2) a hydroxy analog of methionine; and 3) at least one organic trace mineral. The organic trace comprises a metal chelate or a metal salt comprising at least one metal ion and at least one ligand, wherein the ligand is a compound comprising Formula (III):

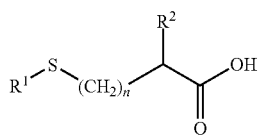

(III)

wherein:
R¹ is selected from the group consisting of methyl and ethyl;
R² is selected from the group consisting of hydroxy and amino; and
n is an integer from 0 to 2.

Preferably, the compound comprising Formula (III) is 2-hydroxy-4-methylthiobutanoic acid, i.e., n is 2, R¹ is methyl, and R² is hydroxy.

In an exemplary iteration of this embodiment, the antioxidant comprises 1) a mixture of 1,2-dihydro-2,2,4-trimethylquinoline and tertiary butyl hydroquinone; 2) a calcium salt of 2-hydroxy-4-methylthiobutanoic acid; and 3) zinc, manganese, and copper ions chelated to 2-hydroxy-4-methylthiobutanoic acid. In another exemplary iteration, the antioxidant consists of 1) a mixture of 1,2-dihydro-2,2,4-trimethylquinoline and tertiary butyl hydroquinone; 2) a calcium salt of 2-hydroxy-4-methylthiobutanoic acid; and 3) zinc, manganese, and copper ions chelated to 2-hydroxy-4-methylthiobutanoic acid.

In another preferred embodiment, a combination of the invention comprises 1) at least one antioxidant selected from the group consisting of 6-ethoxy-1,2-dihydro-2,2,4-trimethylquinoline, tertiary butyl hydroquinone, butylated hydroxyanisole, and butylated hydroxytoluene; 2) at least one organic acid; and 3) at least one organic trace mineral. The organic trace comprises a metal chelate or a metal salt comprising at least one metal ion and at least one ligand, wherein the ligand comprises a compound having Formula (III), as defined above. Preferably, the compound comprising Formula (III) is 2-hydroxy-4-methylthiobutanoic acid.

In an exemplary iteration of this embodiment, the antioxidant comprises 1) a mixture of 1,2-dihydro-2,2,4-trimethylquinoline and tertiary butyl hydroquinone; 2) a mixture of benzoic acid, fumaric acid, and 2-hydroxy-4-methylthiobutanoic acid; and 3) zinc, manganese, and copper ions chelated to 2-hydroxy-4-methylthiobutanoic acid. In another exemplary iteration, the antioxidant consists of 1) a mixture of 1,2-dihydro-2,2,4-trimethylquinoline and tertiary butyl hydroquinone; 2) a mixture of benzoic acid, fumaric acid, and 2-hydroxy-4-methylthiobutanoic acid; and 3) zinc, manganese, and copper ions chelated to 2-hydroxy-4-methylthiobutanoic acid.

(j) Feed Rations

The combinations of the invention may also be provided to the animal as a part of a total feed ration. The exact formulation of the animal feed composition is not critical to the present invention. Feed ingredients are selected according to the nutrient requirements of the particular animal for which the feed is intended; these requirements depend, interalia, upon the age and stage of development of the animal, the sex of the animal, and other factors. Feed ingredients may be grouped into eight classes on the basis of their composition and their use in formulating diets: dry forages and roughages; pasture, range plants and forages fed fresh; silages; energy feeds; protein supplements; mineral supplements; vitamin supplements; and additives. See National Research Council (U.S.) Subcommittee on Feed Composition, United States-Canadian Tables of Feed Composition, 3d rev., National Academy Press, pp. 2,145 (1982). These classes are, to a certain extent, arbitrary, as some feed ingredients could be classified in more than one class. Typically, a feed formulation will also depend upon the costs associated with each ingredient, with the leastexpensive composition of ingredients that gives the needed nutrients being the preferred formulation.

By way of non-limiting example, in one embodiment, the animal feed ration is formulated for swine. The feed formulation will vary for piglets, grower and finisher pigs, gilt development, gestating sows, and lactating sows. Swine feed formulations typically comprise grains (e.g., corn, barley, grain sorghum, oats, soybeans, wheat, etc.), crude proteins (e.g., fish meal, gluten meal, meat meal, soybean meal, tankage, which is the residue that remains after rendering fat in a slaughterhouse, etc.), crude fat (e.g., fish oils, vegetable oils, animal fats, yellow grease, etc.), supplemental amino acids (e.g., lysine, methionine or methionine analogs, etc), vitamins, minerals, and other supplemental agents.

In another embodiment, the animal ration is formulated for aquatic animals. As appreciated by a skilled aquaculturist, the feed formulation depends upon the organism being cultured and the developmental stage of the organism. Typical aquaculture preparations contain energy sources, e.g., protein from animal blood meal, meat and bone meal, poultry meal, crab meal, fish meal, shrimp meal, squid meal, and krill; protein/carbohydrates from plants (e.g., alginates, canola, corn, corn gluten, cottonseed meal, kelp meal, molasses, legumes, peanut meal, rice, soybeans, soy protein concentrate, soybean meal, wheat, and wheat gluten); and oils (e.g., fish oil, vegetable oil). The feed preparation may be further supplemented with amino acids (e.g., arginine, histidine, isoleucine, lysine, methionine, phenylalanine, threonine, tryptophan, and valine); vitamins, minerals, and other supplemental agents.

In another embodiment, the animal feed ration is formulated for poultry. As noted above, feed formulations depend in part upon the age and stage of development of the animal to be fed. Leeson and Summers (Nutrition of the Chicken, 4th ed., pp. 502-510, University Books, 2001) describe several representative poultry diets for pullets, layers, broilers and broiler breeders. For example, most chicken diets contain energy concentrates such as corn, oats, wheat, barley, or sorghum; protein sources such as soybean meal, other oilseed meals (e.g., peanut, sesame, safflower, sunflower, etc.), cottonseed meal, animal protein sources (meat and bone meal, dried whey, fish meal, etc.), grain legumes (e.g., dry beans, field peas, etc.), and alfalfa; and vitamin and mineral supplements, if necessary (for instance, meat and bone meal is high in calcium and phosphorous, and thus these minerals do not need to be supplemented in a feed ration containing meat and bone meal).

In another embodiment, the animal ration is formulated for a ruminant animal. The nutrient and energy content of many common ruminant feed ingredients have been measured and are available to the public. The National Research Council has published books that contain tables of common ruminant feed ingredients and their respective measured nutrient and energy content. Additionally, estimates of nutrient and maintenance energy requirements are provided for growing and finishing cattle according to the weight of the cattle. National Academy of Sciences, Nutrient Requirements of Beef Cattle, Appendix Tables 1-19, 192-214, National Academy Press, (2000); Nutrient Requirements of Dairy Cattle (2001), each incorporated herein in its entirety. This information can be utilized by one skilled in the art to estimate the nutritional and maintenance energy requirements of cattle with non-functional rumens, such as calves under about 500 lbs in weight, or cattle with functional rumens, such as growing cattle or dairy cattle.

The combination of the invention may be provided to the animal either separately or at the same time as a part of a composition. The combination may be formulated as liquids, emulsions, or dry or powdered supplements to be added to other foods, such as grains, protein products, and mixtures thereof. The dry feed supplement may be uniformly dispersed throughout a dry or liquid food. Feed compositions may also be provided as aqueous formulations. An aqueous formulation may be a solution or an emulsion. The aqueous formulation may be added directly to the drinking water of an animal or it may be mixed into or applied to a dry or liquid food.

(II) Methods for Improving Animal Health and Performance

Another aspect of the invention provides methods for improving animal health and performance by providing a combination of the invention to the animal of interest. Those of skill in the art will appreciate that the specific combination provided to a particular animal can and will vary depending upon the species, sex, and age of the animal. Furthermore, a variety of health and performance parameters may be affected by administration of the combinations of the invention.

In some embodiments, combinations of the invention may be provided to dairy ruminants, such as dairy cattle, dairy sheep, and dairy goats. In a preferred embodiment, the dairy ruminant is a dairy cow. Non-limiting examples of suitable health parameters to be assessed include body weight, body condition score, body temperature, food intake, antioxidant status, markers of oxidative stress, serum protein levels, serum mineral levels, immune system function, health and diversity of rumen microflora, fecal bacteria, and so forth. Suitable performance parameters include, but are not limited to, milk yield, milk efficiency, milk fat, milk protein, somatic cell counts, FCM, ECM weight gain, feed:gain ratio, nutrient digestibility, feed conversion ratio, pregnancy rate, number of offspring, weight of offspring, and so forth.

In other embodiments, combinations of the invention may be fed to non-dairy ruminants, such as beef cattle, veal, and lambs. Examples of suitable health parameters include but are not limited to body weight, body condition score, body temperature, food intake, antioxidant status, markers of oxidative stress, serum protein levels, serum mineral levels, immune system function, health and diversity of rumen microflora, fecal bacteria, bone and joint health, and so forth. Non-limiting examples of suitable performance parameters include weight gain, feed:gain ratio, nutrient digestibility, feed conversion ratio, carcass quality, carcass yield, meat grade, meat yield, meat protein to fat ratio, and the like.

In still other embodiments, combinations of the invention may be provided to swine; that is, sows, starter piglets, grower pigs, finisher pigs, and boars. Non-limiting examples of health parameters include body weight, body condition score, body temperature, food intake, antioxidant status, markers of oxidative stress, serum protein levels, serum mineral levels, immune system function, health and diversity of gut microflora, fecal bacteria, bone and joint health, and the like. Examples of suitable performance parameters include but are not limited to weight gain, feed:gain ratio, nutrient digestibility, feed conversion ratio, wean to estrus interval, fertility rate, number of offspring, weight of offspring, farrowing rate, days to weaning, carcass quality, carcass yield meat grade, meat yield, meat protein to fat ratio, and the like.

In further embodiments, combinations of the invention may be provided to poultry, such as laying chickens, broiler chickens, turkeys, and ducks. Examples of suitable health parameters include but are not limited to body weight, body condition score, body temperature, food intake, antioxidant status, markers of oxidative stress, serum protein levels, serum mineral levels, immune system function, health and diversity of gut microflora, fecal bacteria, bone and joint health, and so forth. Non-limiting examples of suitable performance parameters include weight gain, feed:gain ratio, nutrient digestibility, feed conversion ratio, egg yield, egg quality, eggshell quality, carcass quality, carcass yield, meat grade, meat yield, meat protein to fat ratio, and the like.

In additional embodiments, combinations of the invention may be provided to horses. Non-limiting examples of health parameters include body weight, body condition score, body temperature, food intake, antioxidant status, markers of oxidative stress, serum protein levels, serum mineral levels, immune system function, health and diversity of gut microflora, fecal bacteria, bone and joint health, and the like. Non-limiting examples of suitable performance parameters include weight gain, feed:gain ratio, nutrient digestibility, feed conversion ratio, stride length, jump distance, speed, and the like.

In additional embodiments, combinations of the invention may be provided to aquaculture animals, such as fish, shrimp, oysters, mussels, and the like. Examples of suitable health parameters include but are not limited to body weight, body condition score, food intake, antioxidant status, markers of oxidative stress, serum protein levels, serum mineral levels, immune system function, health and diversity of gut microflora, fecal bacteria, and so forth. Non-limiting examples of suitable performance parameters include weight gain, feed:gain ratio, nutrient digestibility, feed conversion ratio, shell quality, carcass quality, carcass yield, meat grade, meat yield, meat protein to fat ratio, and the like.

In still further embodiments, combinations of the invention may be fed to companion animals such as cats, dogs, and the like. Examples of suitable health parameters include but are not limited to body weight, body condition score, food intake, antioxidant status, markers of oxidative stress, serum protein levels, serum mineral levels, immune system function, body temperature, health and diversity of gut microflora, fecal bacteria, bone and joint health, and so forth. Non-limiting examples of suitable performance parameters include weight gain, feed:gain ratio, nutrient digestibility, feed conversion ratio, mobility, agility, quality of life, and the like.

In an exemplary embodiment, a method for reducing oxidative stress in an animal comprises feeding a combination of the invention to the animal. The combination comprises at least one antioxidant selected from the group consisting of 1) at least one antioxidant selected from the group consisting of 6-ethoxy-1,2-dihydro-2,2,4-trimethylquinoline, tertiary butyl hydroquinone, butylated hydroxyanisole, and butylated hydroxytoluene; 2) a hydroxy analog of methionine; and 3) at least one organic trace mineral. The organic trace comprises a metal chelate or a metal salt comprising at least one metal ion and at least one ligand, wherein the ligand is a compound comprising Formula (III):

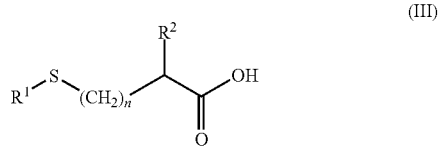

wherein:
R¹ is selected from the group consisting of methyl and ethyl;
R² is selected from the group consisting of hydroxy and amino; and
n is an integer from 0 to 2.

Preferably, the compound comprising Formula (III) is 2-hydroxy-4-methylthiobutanoic acid, i.e., n is 2, R¹ is methyl, and R² is hydroxy.

In an exemplary iteration of this embodiment, the combination comprises: 1) 1,2-dihydro-2,2,4-trimethylquinoline and tertiary butyl hydroquinone; 2) a calcium salt of 2-hydroxy-4-methylthiobutanoic acid; and 3) zinc, manganese, and copper ions chelated to 2-hydroxy-4-methylthiobutanoic acid; and the animal is a dairy cow.

In another exemplary embodiment, a method for reducing oxidative stress in an animal comprises feeding a combination of the invention to the animal. The combination comprises at least one antioxidant selected from the group consisting of 1) at least one antioxidant selected from the group consisting of 6-ethoxy-1,2-dihydro-2,2,4-trimethylquinoline, tertiary butyl hydroquinone, butylated hydroxyanisole, and butylated hydroxytoluene; 2) a hydroxy analog of methionine; and 3) at least one organic trace mineral. The organic trace comprises a metal chelate or a metal salt comprising at least one metal ion and at least one ligand, wherein the ligand is a compound comprising Formula (III), as detailed above.

In an exemplary iteration of this embodiment, the combination comprises: 1) 1,2-dihydro-2,2,4-trimethylquinoline and tertiary butyl hydroquinone; 2) as mixture of benzoic acid, fumaric acid, and 2-hydroxy-4-methylthiobutanoic acid; and 3) zinc, manganese, and copper ions chelated to 2-hydroxy-4-methylthiobutanoic acid; and the animal is a chicken.

DEFINITIONS

To facilitate understanding of the invention, several terms are defined below.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkoxy" as used herein refers to an alkyl group (R) linked to an oxygen (—OR).

The term "DM" stands for dry matter.

The term "improved antioxidant status" as used herein, refers to an improved antioxidant capacity of the animal to remove free radicals from its system.

As various changes could be made in the above compounds, products and methods without departing from the scope of the invention, it is intended that all matter contained in the above description and in the examples given below, shall be interpreted as illustrative and not in a limiting sense.

EXAMPLES

The following examples illustrate various embodiments of the invention.

Example 1

Combination of Organic Acids and Antioxidants Improves Sow Health and Performance Lactating sows often do not consume sufficient nutrients to meet the nutrient demands of lactation. First-parity sows and sows lactating during hot periods are particularly susceptible to insufficient dietary intake, and as a consequence, may mobilize body reserves to support lactation needs. Excessive losses of body reserves may affect subsequent reproductive performance as manifested by a delayed wean to estrus interval, failure to conceive, reduced litter size, and, ultimately, culling. Furthermore, loss of body condition and the rapid onset of lactation, especially in the first week post-farrowing, may increase the level of oxidative stress, which may also contribute to reduced performance.

During gestation, sows are typically limit fed (i.e., ~4-5 lbs/day) to maintain body condition. After farrowing, however, the nutrient needs for lactation increase rapidly and substantially to a level of feed intake 3 to 4 times the gestation feed intake (i.e., ~15 lbs/day). This rapid rise in feed intake and changes in the nutrient density of the diet require considerable adaptations on the gastrointestinal tract to process the higher nutrient intake. Such adaptations may be manifested by greater digestion capabilities, tract size, enzyme production, nutrient transporters, and changes in the microflora populations. Frequently, this transition to higher feed intake is not achieved smoothly and lower feed intake during lactation occurs with body reserve losses and/or poor lactation performance. Also, during this transitional period, sow metabolism undergoes dramatic shifts to support lactation performance. These changes in metabolism may also increase oxidative stress, which is an energy cost to the lactating sow.

Increasing feed intake during early lactation would be especially beneficial because as much as 40% of sow body weight losses occur in the first week of lactation. However, many producers limit sow feed intake during the first week of lactation to transition the sows to the higher level of feed intake to prevent poor feed intake later in lactation. Therefore, opportunities to improve lactation feed intake, especially in early lactation would be beneficial. Some recent studies have suggested that the dietary addition of organic acids improved feed intake during early lactation, as well as improved litter performance. Studies that showed marked improvements were conducted during hot weather conditions, which will depress feed intake and increase oxidative stresses. Whereas, other studies that showed only minimal improvements in sow feed intake due to dietary organic acids were not conducted during hot weather conditions, which suggests that the improved response may depend upon adverse conditions such as hot weather.

The objective of the trial presented below was to improve feed intake during lactation and increase litter weights by alleviating oxidative stress associated with lactation and enhancing the ability of the gastrointestinal tract to achieve a rapid rise in nutrient intake via the dietary addition of organic acids and/or antioxidants. The present trial was conducted in August, which is a hot weather period in the US Midwest. Specific objectives of the study were to 1) improve lactating sow health and feed intake by reducing the bacterial counts of pathogenic organisms and reducing the energy costs of oxidative stress, and 2) increasing litter weaning weights and reducing the number of low value pigs via improved milk production by improving the energy balance of lactating sows.

a. Animals, Treatment Groups, and Measurements

A total of 112 mixed parity sows (C22 and C29 PIC lines; Pig International Company, Franklin, Ky.) were randomly assigned to one of the following four treatments:

1) Control
2) Organic acids (i.e., a blend of benzoic acid, fumaric acid, and 2-hydroxy-4(methylthio)butanoic acid (HMTBA) sold under the trademark ACTIVATE STARTER DA® by Novus Intl.) at 0.4%
3) Antioxidants (i.e., a blend of 6-ethoxy-1,2-dihydro-2,2,4-trimethylquinoline (ethoxyquin) and tertiary butyl hydroquinone (TBHQ) sold under the trademark AGRADO® Plus by Novus Intl.) at 125 ppm
4) Combination of organic acids (as defined above in treatment 2) and antioxidants (as defined above in treatment 3)

The sows were given their respective treatments upon entry into the farrowing house and continued until weaning. Previous PigChamp records were available to adjust randomization of animals to treatment. Animals were cared for according to standard site practices that included daily observations (including mortalities and culls—by crate, identification, date, and cause of death), room temperature monitoring, and feeder and waterer observations. All cross-fostering was conducted within each treatment only and no further cross-fostering was done after initial litter weights (i.e., 2 days post-farrowing) were collected. If small pig litters were formed by cross-fostering, these litters were balanced across treatments. Baby pigs were observed daily and incidences of health problems, fall-behinds, mortalities, cause of death, and health records were recorded by litter.

The experiment was designed as a randomized block design within 2 farrowing rooms. Each farrowing room (of 56 crates) was considered a block. Sows were blocked by parity and previous performance based on PigChamp records. Within a block, sows were randomly assigned to one of the four treatments to provide n=28 sows per treatment. Each sow was housed in a standard sized crate (5×7½ feet) equipped with supplemental heat lamps and nipple waterers. The two farrowing rooms were equipped with thermo-controlled heating and ventilation systems, as well as the HOWEMA feeding system to deliver the respective dietary treatments on a daily basis. All animals were farrowed in the designated rooms and returned to the production system at weaning. Subsequent reproductive performance measurements (including sows culled) were in accordance with standard farm procedures.

Diets.

Sows were fed a standard corn-soybean meal diet with modest inclusion rates of synthetic amino acids (i.e., 4 lbs/ton synthetic Lysine) (see Table 1). Diets were balanced to meet NRC requirement for nutrient and energy (see Table 2), as well as nutritional requirements for lactating sows with the TID (true ileal digested) lysine levels of 1.05%. Methionine activity was supplied by either the organic acid blend (i.e., ACTIVATE STARTER DA®) or DL-Met and mixed according to the diet formulations. The 125 ppm level of the antioxidant mix allowed for 25 ppm of ethoxyquin to be supplied via the fat source.

TABLE 1

Diet Formulations.

| Ingredient | 1 Control lbs/ton (%) | 2 Organic Acids lbs/ton (%) | 3 Antioxidants lbs/ton (%) | 4 Organic Acids and Antioxidants lbs/ton (%) |
|---|---|---|---|---|
| Corn | 1288.20 (64.41) | 1282.63 (64.13) | 1287.70 (64.39) | 1282.13 (64.11) |
| SBM-48.5 | 545.40 (27.27) | 545.40 (27.27) | 545.40 (27.27) | 545.40 (27.27) |
| CWG | 80.00 (4.00) | 80.00 (4.00) | 80.00 (4.00) | 80.00 (4.00) |
| Monocal | 38.55 (1.93) | 38.56 (1.93) | 38.55 (1.93) | 38.56 (1.93) |
| Limestone | 23.31 (1.17) | 23.31 (1.17) | 23.31 (1.17) | 23.31 (1.17) |
| Salt | 10.00 (0.50) | 10.00 (0.50) | 10.00 (0.50) | 10.00 (0.50) |
| Lysine | 4.00 (0.20) | 4.00 (0.20) | 4.00 (0.20) | 4.00 (0.20) |
| Met-DL | 2.47 (0.12) | 0.00 | 2.47 (0.12) | 0.00 |
| Thr | 1.04 (0.05) | 1.05 (0.05) | 1.04 (0.05) | 1.05 (0.05) |
| Choline | 2.00 (0.10) | 2.00 (0.10) | 2.00 (0.10) | 2.00 (0.10) |
| EC-Vitamin | 1.00 (0.05) | 1.00 (0.05) | 1.00 (0.05) | 1.00 (0.05) |
| EC-Mineral | 2.00 (0.10) | 2.00 (0.10) | 2.00 (0.10) | 2.00 (0.10) |
| EC-Sow pak | 2.00 (0.10) | 2.00 (0.10) | 2.00 (0.10) | 2.00 (0.10) |
| ACTIVATE DA ® | 0.00 | 8.00 (0.40) | 0.00 | 8.00 (0.40) |
| AGRADO ®Plus | 0.00 | 0.00 | 0.50 (0.025) | 0.50 (0.025) |
|  | 2000.0 (100.0) | 2000.0 (100.0) | 2000.0 (100.0) | 2000.0 (100.0) |

TABLE 2

Calculated Analyses

| Nutrient | Amount |
|---|---|
| ME, kcal/kg | 3445 |
| CP, % | 18.85 |
| Lys, tot % | 1.17 |
| TID Lys, % | 1.05 |
| TID TSAA, % | 0.63 |
| Ca, % | 0.86 |
| P, tot % | 0.76 |
| P avail, % | 0.43 |
| Thr/Lys | 65 |
| TSAA/Lys | 63 |

Measurements.

The study period spanned from the time the sows entered the farrowing room (day 0), when treatment was initiated, until they left the farrowing room after weaning (~day 20), when the treatment was terminated. Animals were observed twice daily including weekends and holidays, and any abnormal observations or mortalities were recorded. Ambient temperatures were recorded daily and heat lamps were adjusted according to standard farm procedures.

After farrowing, sows were limit fed 1.8, 2.7, and 3.6 kg from day 1 (day of farrowing) to day 3, respectively, and then ad libitum until weaned. Daily net feed intake was measured by the difference between the amount of feed offered and feed not consumed.

Litter and sow weights (based on equation from pre-farrowing weight) were collected in kilograms at 2 days post-farrowing and again at weaning. Sow backfat was measured in mm at 2 days post-farrowing and at weaning by real-time ultrasound. Sow body temperatures were collected at 5 days post-farrowing using either remove sensor or rectal thermometers. Blood samples were collected from 10 sows/treatment group at 2-4 days post-farrowing and at weaning. The sample collected at 2-4 days post-farrowing was collected only if the sample could be collected without sow restraint. Briefly, a lidocaine cream was spread on the inside of the front leg. After approximately 5 minutes, a butterfly catheter was inserted into a subcutaneous vein for the collection of the blood sample. However, if this procedure disrupted the sow extensively, it was not collected. Blood was measured for indicators of barrier function (examples may include: protein, cytokines D-lactate, endotoxin), oxidative stress (SOD, glutathione peroxidase activity), NEFA (indication of fat mobilization), and PUN (utilization of amino acids). Fecal samples were collected from a portion of the sows at 5 days post-farrowing and at weaning, and it was cultured for *E. coli*, *Clostridium*, and *Lactobacilli*.

Subsequent (i.e., after ~day 20) reproductive performance measurements were collected via PigChamp (parameters included wean to estrus interval, number of animals bred by 7 days post-weaning, number of services/conception, conception rate, farrowing rate, etc.).

Data were analyzed by analysis of variance procedures appropriate for a randomized design using the General Linear Models procedure of SAS®. Main effects of the model were the blocks (room, parity, previous performance) and treatment. Differences of least square means (LSD test) from treatments and control were determined using a least square comparison.

b. Results

Figure 2:
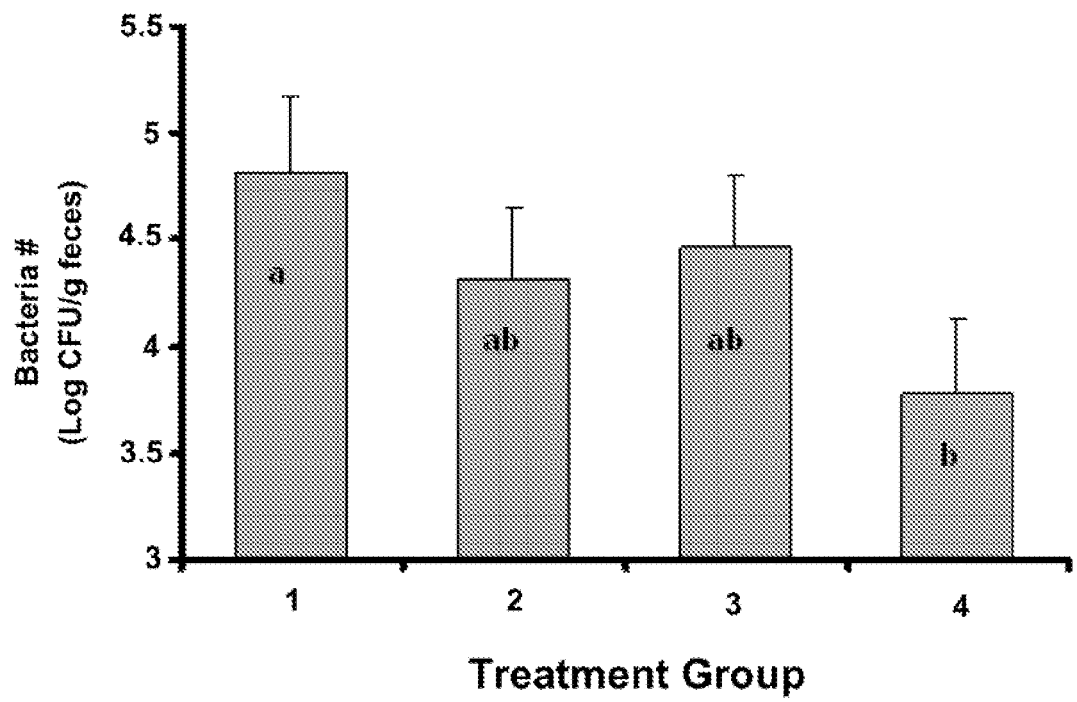
FIG. 2 presents the effects of dietary organic acids and/or antioxidants on sow fecal Clostridium levels at approximately five days post-farrowing. Plotted is the log CFU of bacteria per g of feces as a function of treatment group (n=10). Treatment groups are as defined in the legend of FIG. 1. Treatments with the same superscripts (letters) are not significantly different.

Sow body temperatures were reduced significantly at 5 days post-farrowing in the organic acid and antioxidant treatment groups (see FIG. 1). The greatest reduction was observed in the combination treatment group. Additionally, sow fecal *Clostridrium* levels were reduced significantly in the organic acid and antioxidant treatment groups, with the greatest reduction in the combination treatment group (see FIG. 2). These data indicate that the health of lactating sows is improved by the addition of organic acids and antioxidants to their diet rations.

Example 2

Combination of Antioxidant and Organic Trace Minerals Improves Antioxidant Status of Broiler Chickens Feeding adequate levels of trace minerals has been shown to benefit the antioxidant status of high producing reproductive and growing animals, potentially leading to better animal performance. Certain organic trace minerals have been shown to have higher bioavailability than inorganic forms. The specific objective of this trial was to assess the effects of dietary supplements containing inorganic trace minerals and various sources of organic trace minerals in combination with a single antioxidant on the antioxidant status of broiler chickens.

a. Animals, Treatment Groups, and Measurements

Broiler chickens were placed on one of four diet treatments. The diets comprised standard feed ingredients and contained ethoxyquin on a silica carrier (i.e., 0.01% SANTOQUIN® Mix6, Novus International). There were 12 pen replicates per treatment, and the duration of the trial was 29 days. On day 29 of the study, plasma from 12 birds from each treatment (one per pen) was collected. The plasma was assayed for lipid hydroperoxide levels as a measure of antioxidant status of the birds, using a commercially available kit (No. 705002; Cayman Chemical, Ann Arbor, Mich.).

The four treatments were as follows:
1) Control diet (contained basal levels of trace minerals)
2) Diet contained an additional 30 ppm Zn, 20 ppm Mn, and 5 ppm Cu from inorganic trace mineral salts (ITM)
3) Diet contained an additional 30 ppm Zn, 20 ppm Mn, and 5 ppm Cu from organic trace minerals (OTM) as an amino acid complex
4) Diet contained an additional 30 ppm Zn, 20 ppm Mn, and 5 ppm Cu from organic trace minerals chelated to HMTBA (i.e., MINTREX®, Novus Intl.)

b. Results

Figure 3:
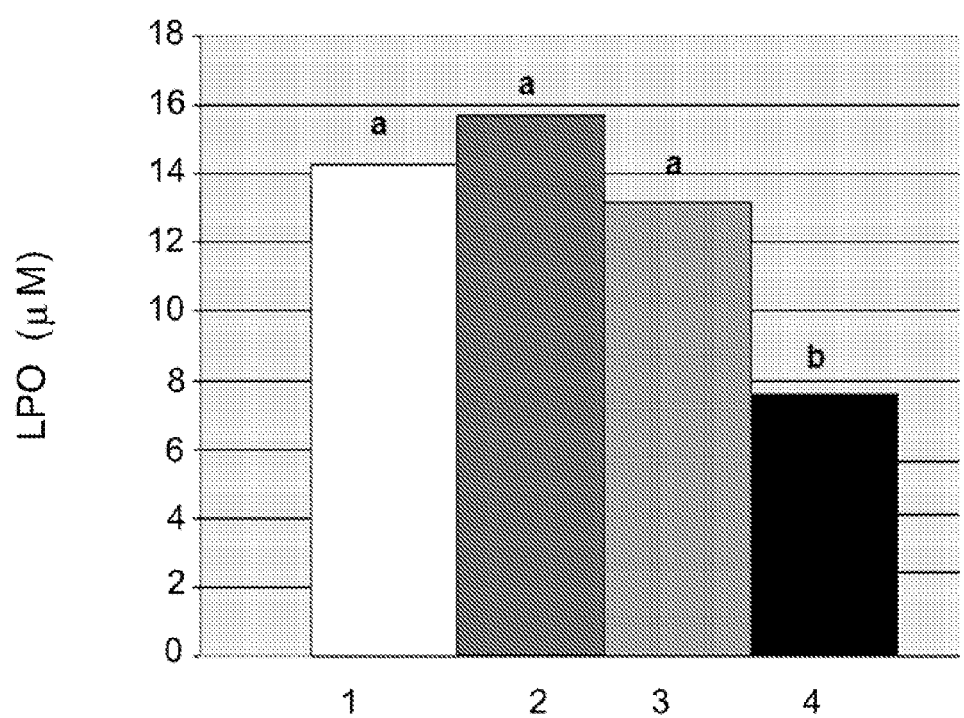
FIG. 3 illustrates the effects of inorganic trace minerals and various sources of organic trace minerals on lipid hydroperoxide levels in broiler chickens. Plotted are the lipid hydroperoxide levels (LPO) in μM at the completion of the study (29 days) versus treatment group. All diets contained ethoxyquin. Treatment 1 received a control diet containing a basal level of trace minerals. Treatment 2 received a diet formulated to contain additional Zn, Mn, and Cu from inorganic trace mineral salts. Treatment 3 received a diet formulated to contain additional Zn, Mn, and Cu as amino acid complexes (i.e., organic trace minerals). Treatment 4 received a diet formulated to contain additional Zn, Mn, and Cu chelated to 2-hydroxy-4-methylthiobutanoic acid (HMTBA). Values are the means of 12 replicate birds per treatment. Treatments with the same superscripts (letters) are not significantly different.

As shown in FIG. 3, the inclusion of organic trace minerals chelated to HMTBA significantly reduced lipid peroxidation relative to the control treatment, whereas inclusion of inorganic trace minerals or trace minerals to with HMTBA, in combination with a single antioxidant, are more effective at reducing oxidative stress than either inorganic trace minerals or amino acid-complexed organic trace minerals in combination with the same single antioxidant.

Example 3

Combination of Organic Trace Minerals, Organic Acids, and Antioxidants Improves Broiler Performance Fast growing birds are under intense metabolic, environmental, health and dietary stresses that adversely affect yields. To alleviate these stresses and improve yields, birds are generally administered drugs and/or dietary supplements. For example, organic trace minerals improve bone structure and immune system function, organic acids improve gut health and function, and antioxidants protect feed ingredients and help maintain animal health at physiological and cellular levels.

Most previous studies focused on the benefits of single products on animal health and meat yield. The objective of the trial presented below, was to compare broiler performance and meat yield when various dietary supplements were administered either individually or in combination. Specific objectives were 1) to compare the effects of organic trace minerals, organic acids, and antioxidants when administered either individually or in combination, and 2) to compare the effects of organic trace minerals, organic acids, and antioxidants when administered either individually or in combination when broilers were challenged with coccidiosis and LPS.

a. Animals, Treatment Groups, and Measurements

The trial was a randomized complete block design consisting of 2208 male broilers (Ross 708) allotted randomly into 12 treatment groups, 8 replicate pens, with 23 birds per pen. The study was conducted at French Village Resources floor pen facility where the birds were cared for according to standard site practices with regard to temperature and light controls. Each pen was equipped with one tube feeder and a nipple watering system with three nipples. The space available in each pen, when corrected for feeder space, was 18 square feet. At the end of the study, the bird density has 0.75 square feet per bird.

Diets.

All diets were designed to meet or exceed all dietary recommendations for broilers (Ross nutrition guide, 2007). Corn, soybean meal, and dried distillers grain solubles (DDGS) were used as the main diet ingredients. Methionine (Met) was balanced across all treatments and was provided by HMTBA (from either ALIMET® or MINTREX®). Samples of each diet were taken from the feed bags, mixed, and then sub-sampled so that a 1 kg sample was obtained for analysis. The following analyses were conducted on feed from each feeding phase (Starter, Grower, and Finisher): 1) levels of Zn, Cu, Mn, Fe, Ca, and P; 2) proximate analysis of feed components to measure moisture, ash, crude protein, crude lipid, crude fiber and digestible carbohydrates; and 3) levels of methionine or methionine precursors such as beta-hydroxy, beta-methylbutyrate (HMB), and HMTBA.

Treatments.

Six of the 12 treatment groups were fed one of six diets (Table 3, treatments 1-6) during the Starter (day 0 to day 10), Grower (day 11 to day 24), and Finisher (day 25 to day 43) periods. The other six treatment groups were fed the same six diets during the same growing periods, but were also challenged with lipopolysaccharides (LPS) from *E. coli* (trichloroacetic acid extraction) and cocci from a live coccidiosis vaccine (i.e., ADVENT®, Novus Intl.) (Table 3, treatments 7-12).

TABLE 3

Description of Treatments.

| Treatment | Description |
| --- | --- |
| 1 | Control diet with inorganic trace minerals (ITM) at NRC (1994) |
| 2 | Replacement of 50% of ITM in control diet with organic trace minerals (OTM) |
| 3 | Control diet + organic acids |
| 4 | Control diet + antioxidant |
| 5 | Treatments 2 & 3 (OTM + organic acids) |
| 6 | Treatments 2, 3, & 4 (OTM + organic acids + antioxidant) |
| 7 | Treatment 1 with cocci and LPS challenge |
| 8 | Treatment 2 with cocci and LPS challenge |
| 9 | Treatment 3 with cocci and LPS challenge |
| 10 | Treatment 4 with cocci and LPS challenge |
| 11 | Treatment 5 with cocci and LPS challenge |
| 12 | Treatment 6 with cocci and LPS challenge |

The organic trace mineral supplement comprised a mixture of Zn, Mn, and Cu chelated to HMTBA (i.e., MINTREX®) used at 40 ppm, 60 ppm, and 8 ppm, respectively, and selenium (Zorien SeY, Novus Intl.) used at 0.3 ppm. The organic acid supplement comprised a mixture of benzoic acid, fumaric acid, and HMTBA (i.e., ACTIVATE® WD for Starter diets or ACIDOMATRIX™ US PRO for Grower and Finisher diets). The antioxidant supplement was ethoxyquin at 133.4 ppm (i.e., SANTOQUIN® at 200 ppm).

Challenge Schedule.

On day 0, all birds were vaccinated against cocci by spraying with live coccidiosis vaccine (ADVENT®, Novus, Intl.). On day 18, all birds in treatment groups 7-12 were challenged with live coccidiosis vaccine by administering a double dose of live cocci vaccine by oral gavage. On day 31, all birds in treatment groups 7-12 were challenged with LPS by subcutaneous injection of 1 mg/kg body weight.

Measurements.

Chicks were observed at least twice daily. All abnormalities and bird mortalities were recorded. Body weights were determined by measuring weight on days 0, 11, 24, 35, and 43. Pen weights for chicks were determined following floor pen standard operating procedures. Individual weights were taken for those birds that had tissues removed. Feed consumption was calculated by determining the weight of each diet provided during each period and dividing that value by the bird weight, as determined above. Antioxidant status was determined by measuring liver glutathione peroxidase enzyme activity. For this, one bird per pen was weighed at day 35, sacrificed at day 36, wherein liver samples were collected. All data were analyzed by analysis of variance procedure appropriate for a randomized block design using the General Linear Models procedure of SAS®.

b. Results

Overall, the 43 day trial data revealed that birds fed a combination of organic trace minerals, organic acids, and an antioxidant outperformed all other treatment groups under both challenge and non-challenge conditions.

Figure 4:
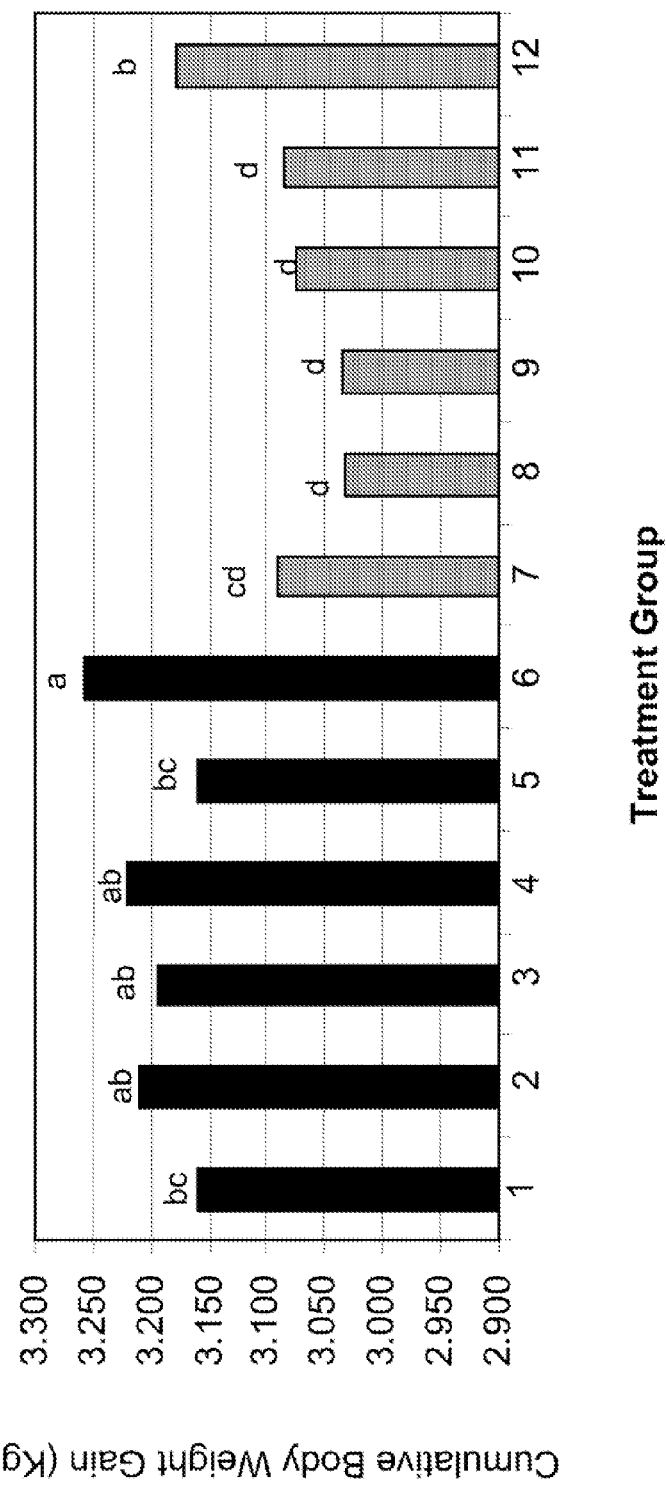
FIG. 4 presents the effects of organic trace minerals, organic acids, and/or an antioxidant on body weight gain in broilers with and without coccidiosis and LPS challenge. Plotted is the cumulative body weight gain in Kg at the completion of the study (43 days) as a function of treatment group. Treatment 1 comprised no supplement treatment; Treatment 2 comprises organic trace minerals; Treatment 3 comprises organic acids; Treatment 4 comprised antioxidant; Treatment 5 comprised a combination of organic trace minerals and organic acids; and Treatment 6 comprised a combination of organic trace minerals, organic acids, and an antioxidant; Treatments 7-12 were the same as Treatments 1-6, respectively, but the broilers were also challenged with E. coli lipopolysaccharides and cocci from a live coccidiosis vaccine. Values are the means of 8 replicate pens per treatment. Treatments with the same superscripts (letters) are not significantly different.

FIG. 4 presents the cumulative body weight gain for each treatment group. Within the challenged and non-challenged groups, broilers fed diets containing a combination of all three additives (i.e., treatments 12 and 6) improved body weight gain by 2.9% (89 g) and 3.1% (98 g), respectively, compared to broilers fed control diets. Administering the treatments individually showed a similar but non-significant ($P>0.05$) improvement compared to control (see FIG. 4).

Figure 5:
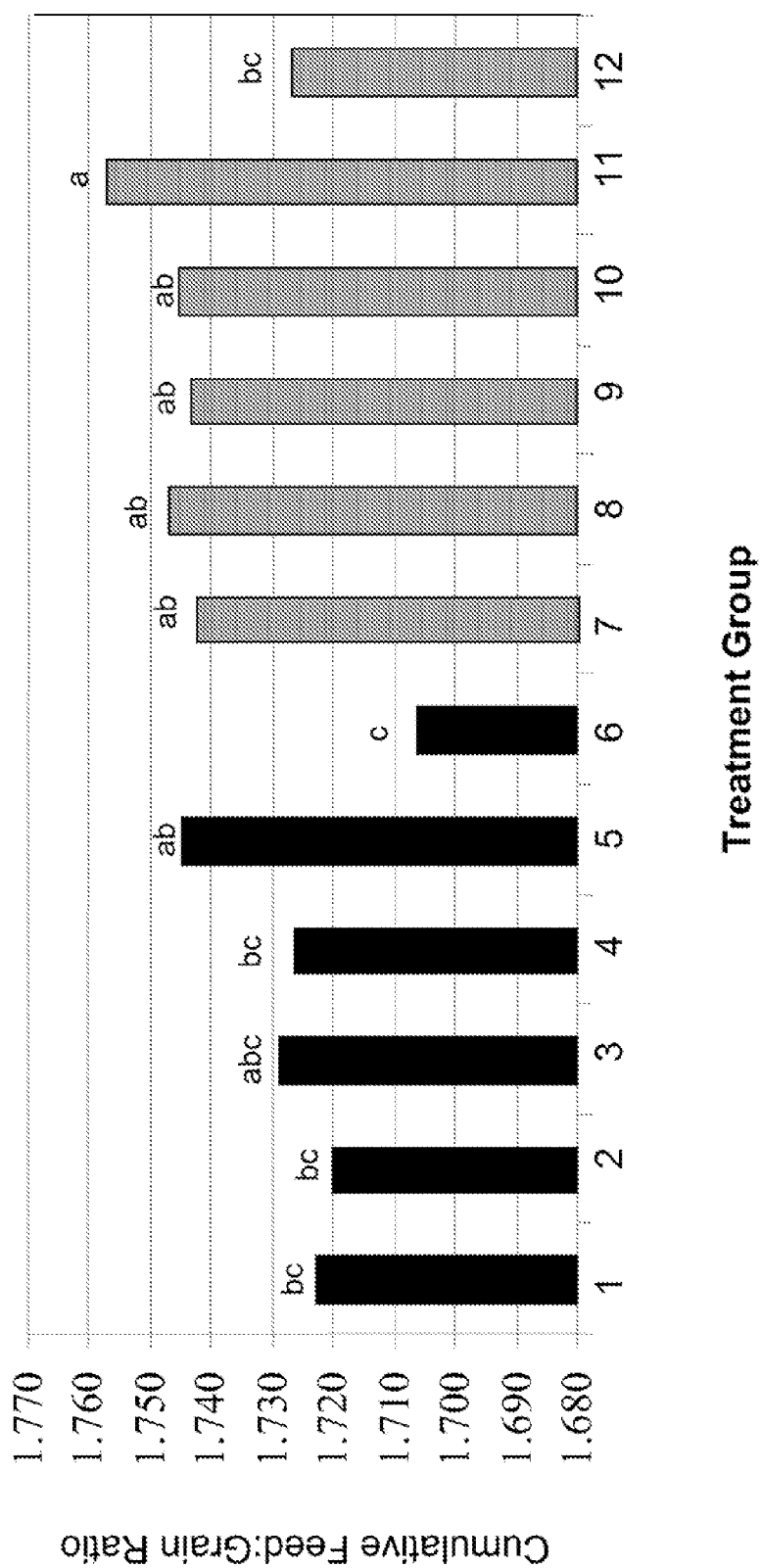
FIG. 5 illustrates the effects of organic trace minerals, organic acids, and/or an antioxidant on the feed to gain ratio in broilers, with and without coccidiosis and LPS challenge. Plotted is the cumulative feed to gain ratio (F:G) at the completion of the study (43 days) as a function of treatment group. Treatment groups are as defined in the legend of FIG. 4. Values are the means of 8 replicate pens per treatment. Treatments with the same superscripts (letters) are not significantly different.

FIG. 5 presents the cumulative ratio of feed to weight gain (F:G) for each treatment group. The feed:gain ratio was corrected for dead birds and was =(feed consumed)/(incremental pen weight+incremental dead bird weight). Feeding the combination of all three supplements improved the adjusted F:G by about 2 points ($P>0.05$) irrespective of challenge conditions.

Figure 6:
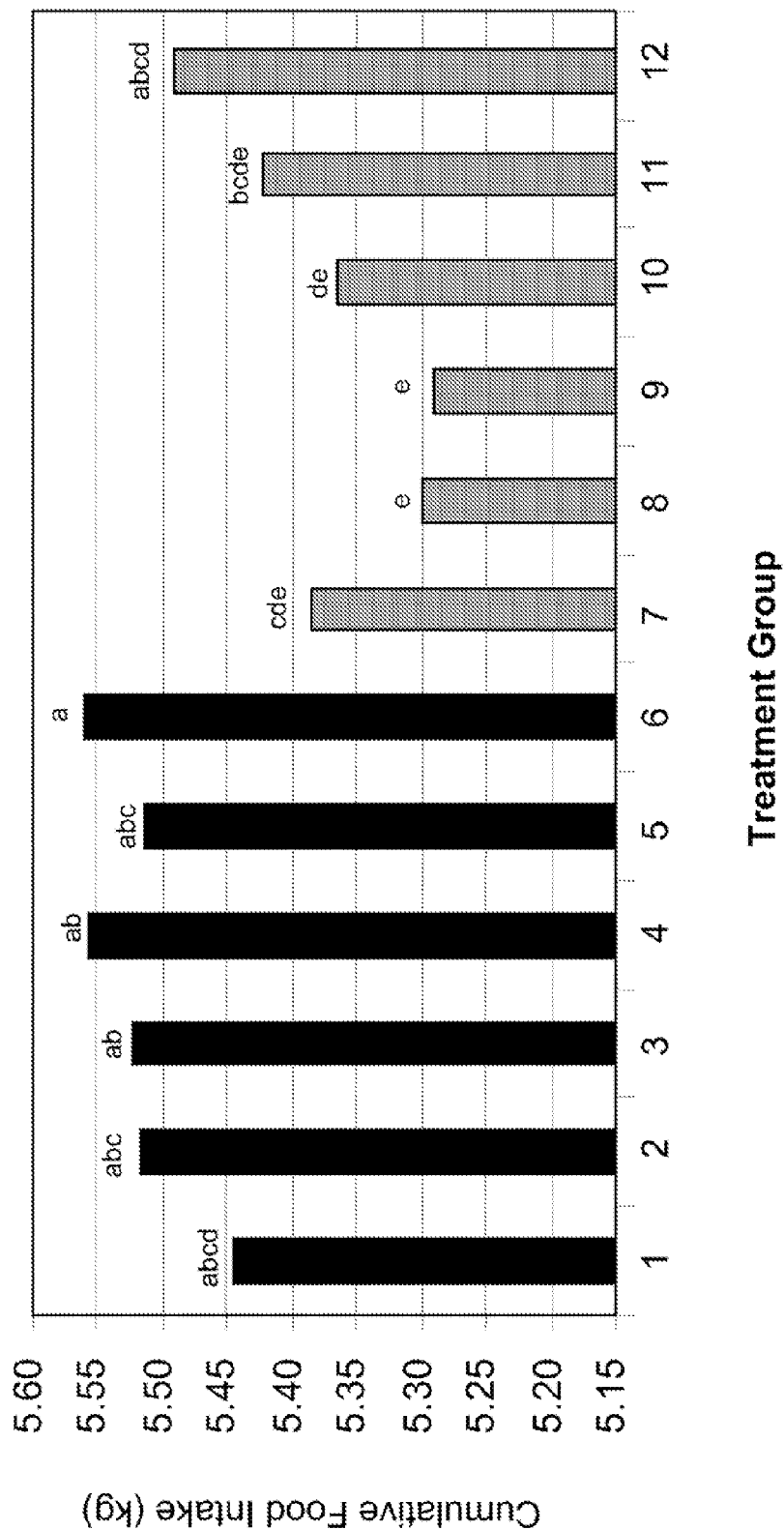
FIG. 6 presents the effects of organic trace minerals, organic acids, and/or an antioxidant on feed intake in broilers, with and without coccidiosis and LPS challenge. Plotted is the cumulative feed intake in Kg at the completion of the study (43 days) versus treatment group. Treatment groups are as defined in the legend of FIG. 4. Values are the means of 8 replicate pens per treatment. Treatments with the same superscripts (letters) are not significantly different.

The cumulative weight gain per treatment group is presented in FIG. 6. In both challenged and non-challenged groups, the improvement in body weight gain was facilitated by improved feed intake.

Figure 7:
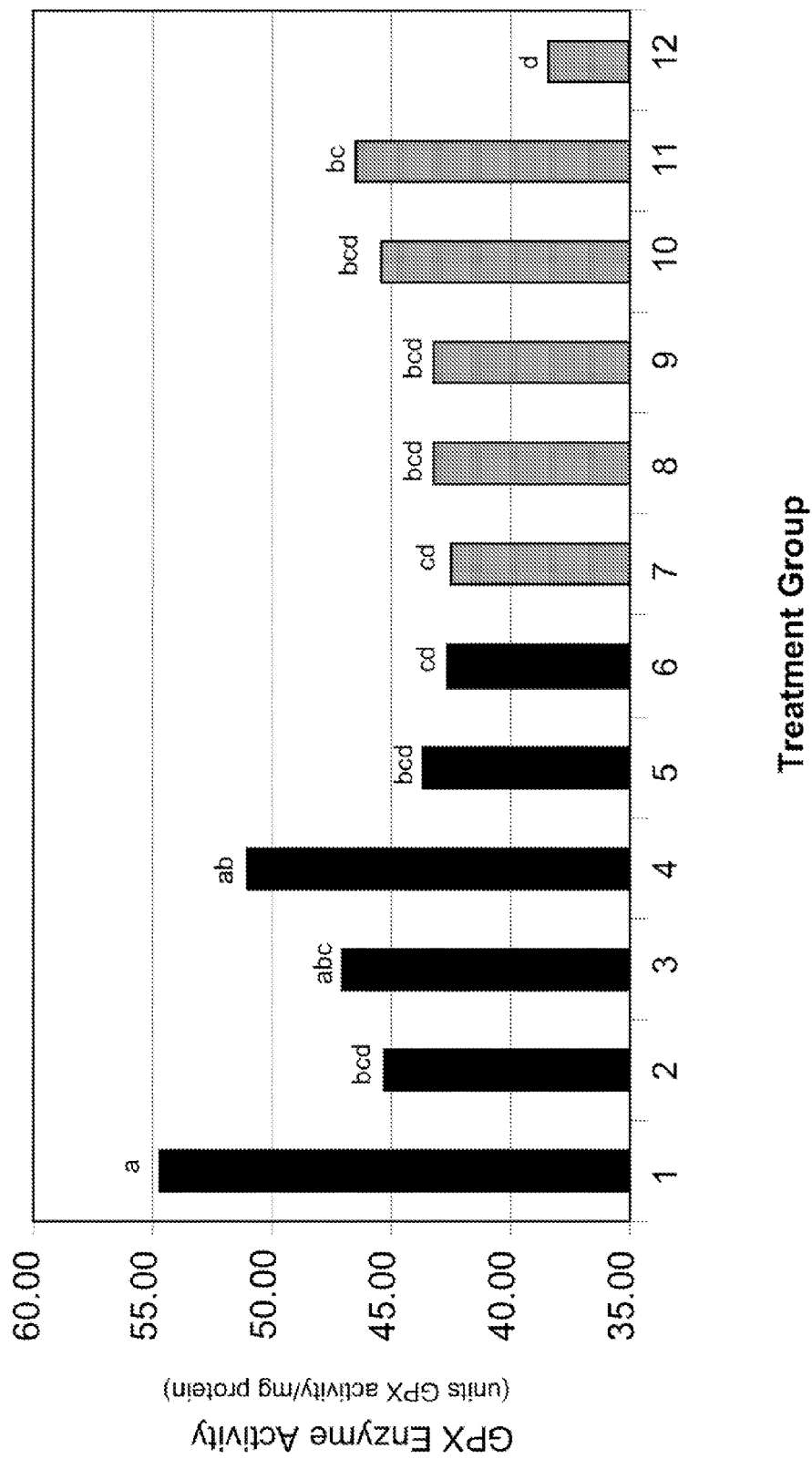
FIG. 7 illustrates the effects of organic trace minerals, organic acids, and/or an antioxidant on liver glutathione peroxidase enzyme activity in broilers, with and without coccidiosis and LPS challenge. Plotted is the glutathione peroxidase (GPx) enzyme activity as a function of treatment group. Treatment groups are as defined in the legend of FIG. 4. Values are the means of 8 replicate pens per treatment. Treatments with the same superscripts (letters) are not significantly different.

FIG. 7 presents glutathione peroxidase (GPX) enzyme activity in each treatment group. The glutathione peroxidase enzyme activity was significantly reduced in the non-challenged group fed the combination of all supplements (treatment 6) compared to the control group suggesting an improved antioxidant capacity. A similar non-significant ($P>0.05$) reduction in glutathione peroxidase enzyme activity was observed in the challenged broilers fed a combination of all three additives (treatment 12) compared to the control group.

Example 4

Combination of Organic Trace Minerals, Methionine Source, and Antioxidants Improves Lactational Performance of Dairy Cows High-producing dairy cows are prone to oxidative stress, and the situation can be exacerbated under certain environmental, physiological, and dietary conditions. Free radicals can damage the cells by oxidizing the essential fatty acids of the lipid membranes, as well as damaging proteins and nucleic acids. Consequently, the health status of the animal may be compromised. Dietary lipids such as supplemental fat, oil seeds, and distiller grains, if not stabilized, can be significant contributors to the load of free radicals in the animal. Dietary antioxidants protect dietary lipids from being oxidized in the final feed and can reduce the damage of free radicals to rumen microorganisms and the animal. Dietary deficiencies in Se, Cu, Zn, Mn, and vitamin also contribute to oxidative stress by compromising the endogenous antioxidant enzymes and the immune response of the animal. Feeding adequate levels of trace minerals has been shown to benefit the health status of cattle by improving the immune response and antioxidant status. But not all sources of trace minerals are equally bioavailable.

The objective of the trial presented below was to evaluate the effects of feeding a combination of organic trace minerals, dietary antioxidants, and a source of methionine on lactation performance in dairy cows.

a. Animals, Treatment Groups, and Measurements

The trial was conducted at Spruce Haven Farm and Research Center in Auburn, N.Y. It was a completely randomized design with three treatments. Fifteen early lactating multiparous cows were used per treatment group. The treatments were as follows:
1) unsupplemented control
2) organic trace minerals supplied as Zn, Mn, and Cu chelated to HMTBA (i.e., MINTREX®) and the antioxidants ethoxyquin and TBHQ (i.e., AGRADO® Plus)
3) organic trace minerals supplied as Zn, Mn, and Cu chelated to HMTBA (i.e., MINTREX®), the antioxidants ethoxyquin and TBHQ (i.e., AGRADO® Plus), and a methionine source provided as a calcium salt of HMTBA (i.e., MFP®, Novus, Intl.).

All cows received the control diet during the first two weeks postpartum. Milk yield measurements during week one (7 days) were used to balance cows during week two. Milk and milk components (fat, protein, SCC, MUN) were also measured during week two post partum, which served as the covariate period. Cows were randomly assigned to one of the three treatments in a completely randomized block design starting the third week post parturition and continued for 14 wks.

Diets.

During weeks one and two, cows were fed the control diet. Cows were started experimental diets on week three and remained on these diets through week 16 postpartum. Cows were fed for ad libitum intake. Diets were formulated using CPM dairy following NRC 2001 recommendations and current industry practices (see Table 4). The nutrient composition of the experimental diet is presented in Table 5. The source of forage was maintained constant during the entire study. Blending of the treatments took place at the dairy facility to ensure product stability. Since the inclusion rates were small, the organic acids and methionine source was provided as a premix with corn meal as the carrier to ensure accuracy.

TABLE 4

Formulation of Experimental TMR.

| Ingredient | % DM basis |
| --- | --- |
| Corn silage | 44.53 |
| Hay crop silage | 10.90 |
| Corn meal | 11.70 |
| Soybean meal (49%) | 1.61 |
| Roasted Soybeans | 4.24 |
| Canola meal | 4.04 |
| Citrus Pulp | 8.74 |
| Corn gluten meal | 0.57 |
| Blood meal | 1.82 |
| Soy-plus | 0.80 |
| Corn distillers | 5.97 |
| Fishmeal | 0.40 |
| Celmanax | 0.25 |
| Calcium carbonate | 0.67 |
| Magnesium oxide | 0.24 |
| Mono Cal 21 | 0.43 |
| Geobond | 0.50 |
| Sodium bicarbonate | 0.90 |
| Selenium 270 | 0.04 |
| Vitamin E 2000 | 0.03 |
| Daily premix | 0.04 |
| Urea | 0.20 |
| Salt | 0.43 |
| Antioxidants/corn oil[1] | 0.83 |
| Organic minerals/methionine source premix[2] | 0.12 |

[1]Antioxidants or corn oil were added to the treatment group TMR daily (0.186 kg/cow/d).
[2]The premix contained corn meal to equal to a total of 0.23 kg/cow/d; the corn meal in the premix was subtracted from the corn in the total ration. The relative proportion of corn and test article were according to a premixing schedule.

TABLE 5

Nutrient Composition of Lactation Diet.

| Nutrient | % DM basis |
| --- | --- |
| Dry matter, % | 49.21 |
| Crude protein, % | 17.4 |
| DIP (% CP) | (54.0) |
| UIP (% CP) | (46.0) |
| Soluble protein (% CP) | (37.3) |
| $NE_L$ (Mcal/lb) | 1.79 |
| NDF (%) | 28.6 |
| NSC (%) | 44.1 |
| Fat (%) | 6.4 |
| Calcium (%) | 0.82 |
| Phosphorus (%) | 0.35 |
| Magnesium (%) | 0.43 |
| Potassium (%) | 1.16 |
| Sulfur (%) | 0.22 |
| Sodium (%) | 0.45 |
| Chloride (%) | 0.40 |
| Iron (ppm) | 160 |
| Selenium (ppm) | 0.30 |
| Cobalt (ppm) | 0.38 |
| Iodine (ppm) | 0.46 |
| Zinc (ppm) | 56 |
| Copper (ppm) | 17 |
| Manganese (ppm) | 61 |

Animal Care.

Animals were cared for according to standard site practices that included daily observations, temperature/health monitoring, and feeder and waterer observations. Cows were housed in individual tie stalls. Dividers for each stall manger were used to minimize cross treatment feed contamination between cows and contain feed to facilitate daily feed delivery and refusal collection. Waterers were shared between two cows.

Measurements.

The following information was collected during the course of the experiment: individual cow dry matter intake (CMI) and individual milk weights were recorded daily at each milking (2× times milking). Individual cow milk samples were collected weekly during one 24-h period, composited based upon the amount of milk produced at each milking and analyzed for milk protein, fat, lactose, total solids, somatic cell count and urea at the Dairy One Lab in Ithaca, N.Y. Body weights and BCS were measured at the start and at the end of the trial. Daily health status of the cows was monitored during the entire study. Dry matter content of the forages was determined weekly. Concentrate and forage samples were collected biweekly and monthly. Composites were analyzed for chemical composition.

Data were analyzed as a Completely Randomized Design with repeated measurements using the MIXED procedure of SAS®. Week or day was used in the repeated measurement statement with cow within treatment as the error term. Pretreatment measurements were used during analysis of covariate.

b. Results

Figure 8:
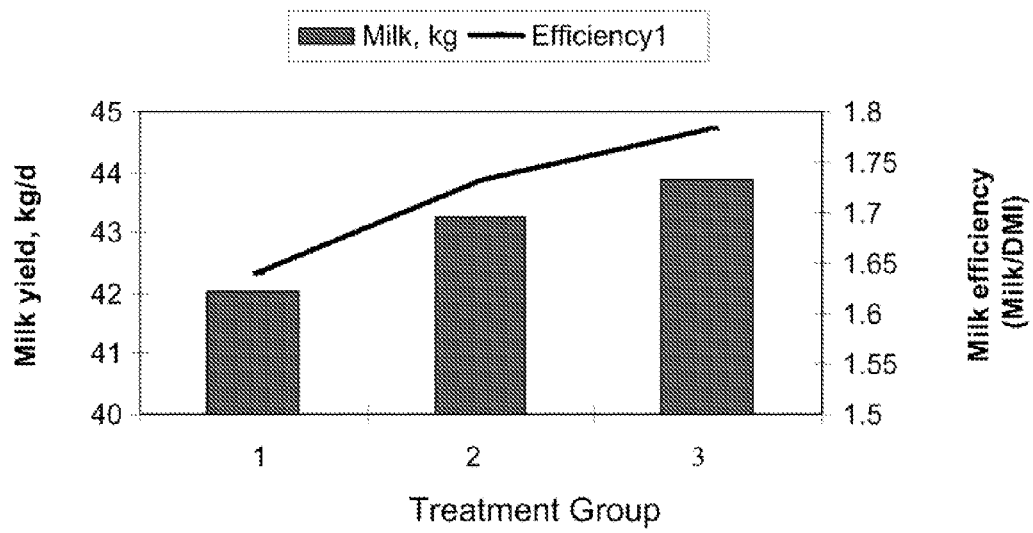
FIG. 8 presents the effects of organic trace minerals, antioxidants, and methionine source on milk yield and milk efficiency in dairy cows. Plotted is milk yield and milk efficiency for each treatment group. Treatment 1 comprised no supplements; Treatment 2 comprised supplemental organic trace minerals and antioxidants; and Treatment 3 comprised supplemental organic trace minerals, antioxidants, and hydroxy analog of methionine.

Dry matter intake was gradually reduced and milk production was gradually increased as the supplements were added to the diets (see Table 6). Cows receiving Treatment 3 or Treatment 2 produced 1.9 kg or 1.3 kg more milk, respectively, than control cows during week 3 through 14. Due to the increase in milk yield and reduction in dry matter intake, milk production efficiency was gradually improved (see FIG. 8) as the supplements were added to the diets. Therefore, feeding the organic trace minerals, antioxidants, and methionine source in combination provided the most improved milk yield and efficiency. Typically, increases in milk production are associated with increases in dry matter intake, making very difficult improvements in efficiencies. In this trial, the benefits of combining antioxidants, trace minerals, and methionine at improving milk production and efficiency were demonstrated at the same time, however.

TABLE 6

Effect of Supplements on Production Responses.[1]

| Variable | Treatment 1 | Treatment 2 | Treatment 3 | SEM |
|---|---|---|---|---|
| Milk, kg | 42.0177x | 43.2772xy | 43.8895y | 0.7834 |
| DMI, kg | 25.9637x | 25.0438xy | 24.9064y | 0.4293 |
| FCM, kg[2] | 39.7543 | 40.4657 | 41.4411 | 0.8728 |
| ECM, kg | 39.4077 | 40.3401 | 40.9967 | 0.8064 |
| Fat, % | 3.156 | 3.0668 | 3.2025 | 0.08036 |
| Fat, kg | 1.3335 | 1.333 | 1.3954 | 0.04136 |
| Protein, % | 2.7636x | 2.8407y | 2.7733xy | 0.02829 |
| Protein, kg | 1.16x | 1.2217y | 1.2143y | 0.02185 |
| Lactose, % | 4.8285 | 4.8858 | 4.8762 | 0.02983 |
| Efficiency (milk/DMI) | 1.6401ax | 1.7318aby | 1.7832by | 0.03287 |

[1] a, b and x, y means in rows with different letters differ P < 0.05 and P < 0.1, respectively.
[2] 3.5% FCM = 0.4324 (kg milk) + 16.218(kg milk fat). Energy-corrected milk was calculated by the following equation: ECM = (kg milk × .327) + (kg milk fat × 12.95) + (kg protein × 7.2).

Figure 9:
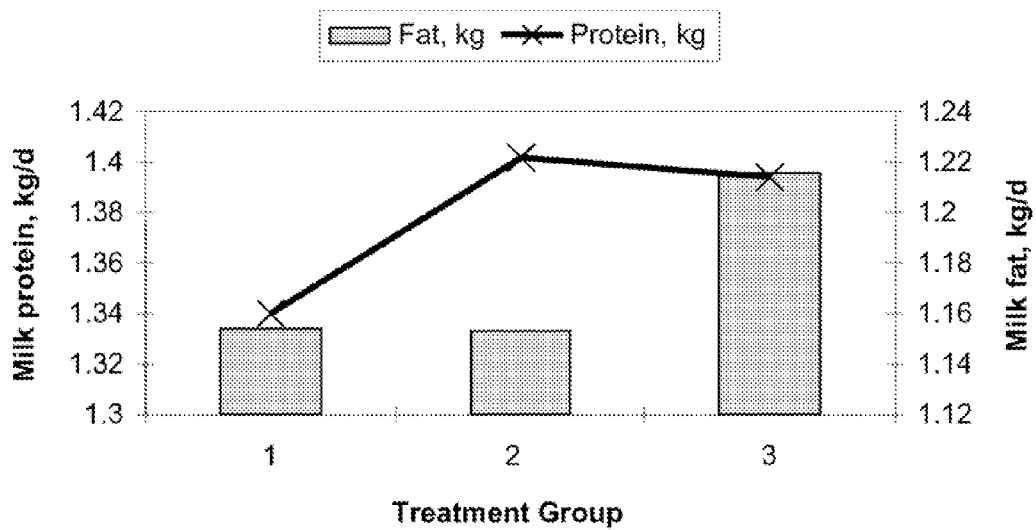
FIG. 9 presents the effects of organic trace minerals, antioxidants, and methionine source on milk protein and milk fat in dairy cows. Plotted is the amount of milk protein and milk fat in the milk of each treatment group. Treatment 1 comprised no supplements; Treatment 2 comprised supplemental organic trace minerals and antioxidants; and Treatment 3 comprised supplemental organic trace

Milk protein and fat composition was also improved with the treatments. Typically, when milk yield is increased it becomes more difficult to improve milk fat and protein composition simultaneously. In this trial, the combination of trace minerals and antioxidants improved milk protein yield and percentage but no improvements in milk fat were observed. If anything, there was a numerical reduction in milk fat percentage over the control. When a methionine source was added to the combination, the benefits of milk protein response from trace minerals and antioxidants were maintained and milk fat was improved over the control (see FIG. 9). From this trial it appears that the combination of trace minerals, dietary antioxidants and methionine was able to improve milk fat and protein simultaneously, which is not possible when each is provided individually.

In summary, when trace minerals in the form of chelates of HMTBA, dietary antioxidants (i.e., ethoxyquin and TBHQ), and methionine in the form of the calcium salt of HMTBA were combined in one treatment, cows were able to produce more milk more efficiently and with higher content of milk fat and protein.

Example 5

Combination of Antioxidants and Organic Trace Minerals Reduces the Negative Effects of Oxidized Corn Oil Fed to Pigs Dried distillers grain solubles (DDGS) are typically added in growing/finishing pig diets, and DDGS fat is highly susceptible to oxidation due to the presence of polyunsaturated fatty acids (NRC, 1998). Thus, growing/finishing diets could contain oxidized lipids, particularly if the feedstuffs are stored for extended periods of time under oxidative conditions. Furthermore, oxidized corn oil fed to pigs during the finishing period may accelerate lipid oxidation in the lipid fraction of meat due to the highly unsaturated fatty acid profile of corn oil and the presence of free radicals originating from the oxidized diet. Thus, accelerated lipid oxidation may be detrimental to meat quality. The objective of the following trial was to evaluate 1) the effect of oxidized corn oil on animal performance and 2) the benefits of combinations of antioxidants and organic trace minerals on preventing the negative effects of oxidized oil on the health and performance of pigs.

a. Materials and Methods

A total of 160 barrows (80.2±2.36 kg) were housed at Spruce Haven Farm and Research Center in Auburn, N.Y. They were fed corn-soybean meal diets mixed with corn oil (Fresh or Oxidized) at 5% inclusion for 56 days before market weight. All diets included Zn, Mn, and Cu ions chelated to HMTBA (i.e., Mintrex®) and either no antioxidants (AOX) or a combination of AOX (i.e., ethoxyquin and TBHQ). The treatment groups were as follows:

1) fresh oil & organic trace minerals
2) fresh oil & organic trace minerals & antioxidants
3) oxidized oil & organic trace minerals
4) oxidized oil & organic trace minerals & antioxidants The experiment was carried-out as a Complete Randomized Block Design in a 2×2 factorial arrangement, with 2 types of corn oil (Fresh vs. Oxidized) and 2 levels of AOX (with or without AOX), with 8 pens per treatment and 5 pigs per pen. Oxidized oil was produced by bubbling oxygen in a heated container up to 48 hrs to reach a target peroxide value (PV) of 150 mEq/kg and 7.5 mEq/kg for the final diet. Ractopamine was added at 5 ppm for the last 28 d of the finishing period. Barrows were weighed at the beginning of the trial and on a weekly basis. Average daily gain (ADG), average daily food intake (ADFI), and gain to feed (GF) ratio were calculated for each group.

b. Results

Pigs fed oxidized oil were 3.9 kg lighter on day 56 than those fed fresh oil (136.0 vs. 139.9 kg, P<0.05). Oxidized oil reduced ADFI in week 1 (9%) and week 2 (7%), while AOX increased ADFI in week 3 (9%) and week 4 (11%, P<0.10). Overall, ADFI was reduced by 5% in pigs fed oxidized oil; that is, ADFI was 2.85 kg and 3.00 kg for oxidized and fresh oil, respectively (P<0.05). Cumulative ADG was reduced on days 14, 49, and 56 in pigs fed oxidized oil (P<0.05). The most profound benefits of AOX were observed in week 3, when AOX improved ADG (0.77 kg vs. 0.97 kg, P<0.01), ADFI (2.63 kg vs. 2.86 kg, P<0.10), and GF (0.291 vs. 0.342, P<0.01) compared to the control. Two-way interaction of oxidized oil and AOX was observed on cumulative GF on day 21 (P<0.10). Barrows fed oxidized oil with AOX had greater GF than those fed oxidized oil without AOX (0.325 vs. 0.292 on 21 d), whereas animals fed diets containing fresh oil with or without AOX were not different (0.319 vs. 0.318 on 21 d). In summary, oxidized oil impaired growth performance and dietary antioxidants (and organic trace minerals) ameliorate the negative effect of oxidized oil in finishing pigs.

Additionally, one of the objectives of the trial was to determine if feeding oxidized fat induces oxidative stress in pigs and if feeding a combination of dietary antioxidants would alleviate these effects. Oxidative stress was assessed by measuring the levels of free carbonyl in plasma proteins. As shown in Table 7, pigs fed oxidized fat higher levels of free carbonyl in plasma protein, indicating increased oxidative damage. Addition of a combination of dietary antioxidants reduced oxidative damage in plasma proteins in both pigs fed oxidized and fresh oil (Table 7a and b). Thus, feeding a blend of AOX improved the antioxidant capacity of the animal and reduced oxidative damage.

Table 7a.
Antioxidant Status

| | Treatment Group | | | |
|---|---|---|---|---|
| | 1 Fresh oil | 2 Fresh Oil + AOX | 3 Oxidized Oil | 4 Oxidized Oil + AOX |
| Free Carbonyl, nmol/mg protein | 26416ab | 14585b | 31449a | 22903ab |

Table 7b.

| SEM | P-value | Oil | AOX | Interaction |
|---|---|---|---|---|
| 4818 | 0.12 | 0.18 | 0.04 | 0.74 |

Example 6

Combination of Antioxidants and Mycotoxin Binder Ameliorate Aflatoxicosis in Growing Pigs Aflatoxicosis in swine is mainly due to the fact that corn is a large part of their diet. Exposure to aflatoxins may have negative effects on health and growth rate, with piglets are more susceptible than adults. The principal target organ for aflatoxins is the liver, and large doses of aflatoxins have been shown to produce hepatic necrosis. The effects of aflatoxicosis can be compounded with the addition of stress.

The following trial was designed to determine whether a combination of antioxidants (i.e., ethoxyquin and tertiary butyl hydroquinone) and a mycotoxin binder (i.e., the mineral clay, hydrated sodium calcium aluminosilicates as provided by SOLIS®, Novus Intl.) could control aflatoxicosis in young growing pigs better than either additive alone.

(a) Materials and Methods

Eighteen litters of crossbred pigs (Yorkshire×Landrace) farrowed at the Virginia Tech Tidewater Agricultural Research and Extension Center swine unit were managed according to standard practice. This included administration of vaccination against Rhinitis, *Pasteurella* Types A and D and Erysipelas (Rhinogen BPE®, Intervet/Schering-Plough, Millsboro, Del.) at day 7 post-farrowing and again at weaning. They were also administered 200 mg of iron dextran, as well as castration of male piglets at day 7 of age. All pigs were weaned as a group at 22+2 days of age and penned as intact litters in an environmentally controlled nursery unit. Pigs were allowed ad libitum access to feed and water via a stainless steel feeder and nipple drinker in each pen. The pre-test post-weaning diet was a complex formulation designed to meet all nutritional requirements and promote rapid adaptation to solid feed (Table 8). Pigs were fed the pre-test diet for 9 days at which time all pigs were individually weighed and the weights recorded for use in allotting pigs to the study.

From the original 18 litters weaned, ninety pigs were blocked by weight, litter of origin and sex, and allotted to balance these factors across experimental dietary treatments. Treatments included:

1) Control: corn-soy diet, uncontaminated, no dietary additive
2) Negative control: corn-soy diet, aflatoxin B1 at 500 ppb, no dietary additive
3) Mycotoxin binder: corn-soy diet, aflatoxin B1 at 500 ppb, mycotoxin binder (i.e., mineral clay)
4) Antioxidant: corn-soy diet, aflatoxin B1 at 500 ppb, antioxidants
5) Combination: corn-soy diet, aflatoxin B1 at 500 ppb, mycotoxin binder and antioxidants The experimental diets (Table 8) were prepared by first preparing a basal diet containing most of the corn and all of the common ingredients for each diet except soy oil, test ingredients, and aflatoxin preparation. Then the appropriate quantities of ground corn, soy oil, mineral clay, antioxidants in oil, and/or aflatoxin preparation were added to and mixed with the basal diet to make each experimental diet. An 80-kg horizontal ribbon mixer was used to premix lesser ingredients with the basal diet before transferring to a larger vertical screw mixer for final mixing of each experimental diet.

TABLE 8

Composition of Diets.[1]

| Item, % | Pre-test diet | Treatments | | | | |
|---|---|---|---|---|---|---|
| | | 1 | 2 | 3 | 4 | 5 |
| Ground corn | 42.69 | 65.84 | 65.4227 | 64.9227 | 65.2827 | 64.7827 |
| Dried whey | 21.00 | — | — | — | — | — |
| Lactose | 4.00 | — | — | — | — | — |
| Plasma protein[2] | 5.00 | — | — | — | — | — |
| Fishmeal | 4.00 | — | — | — | — | — |
| Soybean meal (dehulled) | 15.00 | 22.50 | 22.50 | 22.50 | 22.50 | 22.50 |
| Soy protein concentrate | 4.00 | 6.60 | 6.60 | 6.60 | 6.60 | 6.60 |
| Dicalcium phosphate | 0.49 | 1.26 | 1.26 | 1.26 | 1.26 | 1.26 |
| Limestone | 0.76 | 0.94 | 0.94 | 0.94 | 0.94 | 0.94 |
| Salt | 0.25 | 0.35 | 0.35 | 0.35 | 0.35 | 0.35 |
| Lysine | 0.03 | 0.20 | 0.20 | 0.20 | 0.20 | 0.20 |
| D-L Methionine | 0.03 | 0.02 | 0.02 | 0.02 | 0.02 | 0.02 |
| Vitamin premix | 0.35 | 0.30 | 0.30 | 0.30 | 0.30 | 0.30 |
| Trace mineral premix | 0.15 | 0.15 | 0.15 | 0.15 | 0.15 | 0.15 |
| Carbadox premix[3] | 0.25 | 0.25 | 0.25 | 0.25 | 0.25 | 0.25 |
| Fat (prilled blend) | 2.00 | — | — | — | — | — |

TABLE 8-continued

Composition of Diets.[1]

| Item, % | Pre-test diet | Treatments | | | | |
| --- | --- | --- | --- | --- | --- | --- |
| | | 1 | 2 | 3 | 4 | 5 |
| Soybean oil | — | 1.59 | 1.59 | 1.59 | — | — |
| Antioxidant in oil[4] | — | — | — | — | 1.73 | 1.73 |
| Solis ® | — | — | — | 0.50 | — | 0.50 |
| Aflatoxin preparation | — | — | 0.4173 | 0.4173 | 0.4173 | 0.4173 |
| Total: | 100.00 | 100.00 | 100.00 | 100.00 | 100.00 | 100.00 |
| Calculated analysis: | | | | | | |
| Crude protein, % | 22.15 | 20.38 | 20.34 | 20.30 | 20.34 | 20.29 |
| Lysine, % | 1.48 | 1.28 | 1.28 | 1.28 | 1.28 | 1.28 |
| Calcium, % | 0.85 | 0.76 | 0.76 | 0.76 | 0.76 | 0.76 |
| Phosphorus, % | 0.70 | 0.63 | 0.62 | 0.62 | 0.62 | 0.62 |
| Met. energy, kcal/kg | 3411 | 3376 | 3362 | 3345 | 3369 | 3352 |

[1]Except for the pre-test diet, diets were prepared by first preparing a basal diet consisting of the major portion of the ground corn and all other common ingredients for the diets; then mixing the appropriate test ingredients with the appropriate quantity of basal diet for each experimental diet.
[2]APPETEIN ®, American Protein Corporation, Amu, IA.
[3]MECADOX ®-10, Phibro Animal Health, Ridgefield Park, NJ 07660; provided 55 ppm carbadox in the final diet.
[4]Provided 125 ppm of ethoxyquin and 10 ppm tertiary butylhdroquinone (TBHQ).

Corn used to prepare the diets was assayed by TLC/HPLC and determined to be free of aflatoxins, deoxynivalenol, zearalenone, and T-2 toxin. Excluding the control, aflatoxin contamination of the test diets was achieved by adding the appropriate quantity of a corn-based preparation containing 120 ppm aflatoxin B1 (supplied by Dr. George Rottinghaus, College of Veterinary Medicine, University of Missouri, Columbia). This preparation was added at a level of 0.4173% to provide an aflatoxin B1 contamination level of 500 ppb in the test diets. The mycotoxin binder (i.e., the mineral clay, hydrated sodium calcium aluminosilicate) was provided by SOLIS® at 0.5% (Diets 3 and 5). The antioxidants (Diets 4 and 5) were supplied in a soy oil preparation that provided final diet concentrations of 125 ppm of ethoxyquin and 10 ppm of tertiary butyl hydroquinone (TBHQ). Pigs had ad libitum access to the diets throughout the 3-week experiment via a stainless steel feeder with 4 feeding spaces.

There were six replicate pens (0.91 by 1.22 m) with three pigs each per dietary treatment. On day 4 of the trial all test pigs were vaccinated with *Mycoplasma Hyopneumoniae* Bacterin (RESPISURE®, Pfizer Animal Health, Exton, Pa.) and Porcine Circovirus Vaccine Type 1-type 2 Chimera (SU-VAXYN®, PCV2 One Dose, Fort Dodge Animal Health, Fort Dodge, Iowa). Pen feed consumption (based on disappearance) and individual pig weights were determined at an intermediate point on day 11 and again at the conclusion of the growth assay on day 21. Also on day 21, blood samples were collected into plain vacuum tubes by vena puncture. Serum was harvested by centrifugation and stored frozen until subsequent analysis. Samples were analyzed for serum chemistry, indicators of oxidative stress (i.e., thiobarbituric acid reactive substances (TBARS), malondialdehye (MDA), and Vitamins A and E), and *Mycoplasma hyopneumoniae* titers.

Data were analyzed using the General Linear Models (GLM) procedure of the Statistical Analysis System (SAS Institute, Inc., Cary, N.C.). The pen mean was the experimental unit and the model included the effects of replication and dietary treatment. When a significant ($P<0.05$) F-statistic for dietary treatment was observed, the P-DIFF option of the GLM procedure of SAS was employed for comparison of individual treatment means.

(b) Results
Growth.

Growth performance results for intermediate periods and for the overall 21-day experiment are summarized in Table 9. When performance was assessed at the intermediate point (day 11), pigs fed the diet contaminated with 500 ppb aflatoxin B1 and provided no dietary additive grew at a slower rate ($P<0.05$) than control diet pigs fed an uncontaminated diet. This pattern continued through the end of the growth assay at day 21. The reduced growth rate for the pigs fed the contaminated diet with no feed additive was associated with pronounced reduction in daily feed consumption ($P<0.05$) with no impact on feed efficiency. For the entire 3-week growth period, pigs fed the diet contaminated with aflatoxin and no diet additives grew 27% slower and consumed 29% less feed than the positive control pigs. This observation provides confirmation that the experimental model to test aflatoxin stress was effective.

During the initial 11 days, addition of the mycotoxin binder to the aflatoxin contaminated diet (treatments 3 and 5) resulted in growth rates that were intermediate to and significantly different from ($P<0.05$) the negative control contaminated diet and the uncontaminated control (Table 9). During the period from day 11 to 21 and for the entire trial, the growth rate of pigs fed the contaminated diet and supplemented with the mycotoxin binder was similar to pigs fed the uncontaminated control diet. Furthermore, throughout the trial, pigs fed the contaminated diet supplemented with the mycotoxin binder had feed consumption levels that were similar to the uncontaminated controls. Therefore, supplementation with a mycotoxin binder was effective in ameliorating the negative growth effects associated with feed contamination with 500 ppb aflatoxin B1.

There appeared to be modest numerical growth rate and feed consumption advantages when the aflatoxin contaminated diet was supplemented with the antioxidant preparation. However, improvements above the negative control were not statistically significant (Table 9). Indeed throughout the growth assay, pigs fed the aflatoxin contaminated diet with supplemental antioxidants but without the mycotoxin binder (treatment 4) had growth rate and feed consumption that was significantly poorer ($P<0.05$) than the uncontaminated controls.

TABLE 9

Performance Responses.

| Item | Treatment 1 | 2 | 3 | 4 | 5 | SEM |
|---|---|---|---|---|---|---|
| Pens[1] | 6 | 6 | 6 | 6 | 6 | |
| BW, kg | | | | | | |
| Initial | 9.45 | 9.40 | 9.39 | 9.36 | 9.48 | 0.05 |
| Day 11 | 15.56$^x$ | 13.76$^y$ | 14.99$^z$ | 14.05$^y$ | 14.62$^z$ | 0.19 |
| Day 21 | 22.58$^x$ | 18.91$^y$ | 22.35$^x$ | 19.66$^y$ | 21.77$^x$ | 0.32 |
| ADG, g | | | | | | |
| d 0-11 | 555$^x$ | 397$^y$ | 509$^z$ | 426$^y$ | 467$^z$ | 15 |
| d 11-21 | 702$^x$ | 515$^y$ | 736$^x$ | 560$^y$ | 715$^x$ | 24 |
| Overall | 625$^x$ | 453$^y$ | 617$^x$ | 490$^y$ | 585$^x$ | 15 |
| ADFI, g | | | | | | |
| d 0-11 | 871$^x$ | 650$^y$ | 823$^x$ | 660$^y$ | 784$^x$ | 37 |
| d 11-21 | 1186$^x$ | 803$^y$ | 1207$^x$ | 893$^y$ | 1140$^x$ | 35 |
| Overall | 1021$^x$ | 723$^y$ | 1006$^x$ | 771$^y$ | 953$^x$ | 31 |
| Feed/gain | | | | | | |
| d 0-11 | 1.56 | 1.64 | 1.64 | 1.55 | 1.67 | 0.06 |
| d 11-21 | 1.69 | 1.56 | 1.66 | 1.60 | 1.60 | 0.05 |
| Overall | 1.63 | 1.60 | 1.64 | 1.57 | 1.63 | 0.04 |

[1]Six pens of 3 pigs each per treatment; pen mean was the experimental unit.
$^{x,y,z}$Means in the same row with no common superscript differ (P < 0.05).

Serum Chemistry.

Table 10 presents the most relevant serum minerals and metabolic indicators that were measured. Specific indicators of hepatic function assessed include Aspartate aminotransferase (AST), gamma-Glutamyltransferase (GGT) and direct, indirect and total bilirubin. There were no effects of aflatoxin contamination or of diet supplements on serum concentration of AST. However for GGT, dietary aflatoxin contamination caused a pronounced elevation (P<0.05) of this liver enzyme in serum. Adding the mycotoxin binder to the contaminated diets (treatments 3 and 5) resulted in a complete return of serum GGT levels to a normal level equivalent to the pigs fed uncontaminated diets. Serum GGT concentration in pigs supplemented with the antioxidants (treatment 4) was reduced to a level significantly lower than pigs fed the diet without supplements (50.78 vs. 64.50+0.02 U/L; P<0.05). However, serum GGT levels for pigs supplemented with antioxidants only were still elevated above GGT levels for the control pigs fed uncontaminated diets (50.78 vs. 38.61+0.02 U/L; P<0.05). There were no significant effects of diet treatment on indirect or total bilirubin concentrations. However, direct or conjugated bilirubin was slightly elevated for pigs fed the unsupplemented diet contaminated with aflatoxin as compared to all diet treatments (P<0.05).

TABLE 10

Serum Chemistry Responses.

| Item | Treatment 1 | 2 | 3 | 4 | 5 | SEM |
|---|---|---|---|---|---|---|
| Pens[1] | 6 | 6 | 6 | 6 | 6 | |
| Glucose, mg/dL | 116.61 | 106.39 | 112.50 | 114.22 | 118.61 | 3.09 |
| Urea N, mg/dL | 13.06$^x$ | 10.06$^y$ | 11.58$^{xy}$ | 10.72$^y$ | 12.94$^x$ | 0.65 |
| Creatinine, mg/dL | 0.84 | 0.82 | 0.85 | 0.83 | 0.82 | 0.02 |
| Phosphorus, mg/dL | 10.22 | 10.25 | 10.25 | 9.71 | 9.86 | 0.21 |
| Calcium, mg/dL | 10.87 | 11.06 | 10.96 | 10.87 | 10.94 | 0.10 |
| Magnesium, mg/dL | 2.61 | 2.81 | 2.65 | 2.61 | 2.64 | 0.08 |
| Total protein, g/dL | 5.44$^{xz}$ | 5.11$^y$ | 5.61$^x$ | 5.32$^{yz}$ | 5.53$^{xz}$ | 0.09 |
| Albumin, g/dL | 3.72$^x$ | 3.11$^y$ | 3.71$^x$ | 3.25$^y$ | 3.67$^x$ | 0.06 |
| Globulin, g/dL | 1.73$^x$ | 2.00$^y$ | 1.90$^x$ | 2.07$^y$ | 1.87$^{xy}$ | 0.07 |
| AST, U/L | 38.00 | 39.61 | 39.08 | 37.11 | 36.82 | 2.97 |
| GGT, U/L | 38.61$^x$ | 64.50$^y$ | 37.92$^x$ | 50.78$^z$ | 39.78$^{xz}$ | 3.75 |
| Bilirubin-total, mg/dL | 0.20 | 0.28 | 0.18 | 0.24 | 0.19 | 0.04 |
| Bilirubin-direct, mg/dL | 0.02$^x$ | 0.09$^y$ | 0.00$^x$ | 0.02$^x$ | 0.00$^x$ | 0.02 |
| Bilirubin-indirect, mg/dL | 0.18 | 0.19 | 0.18 | 0.23 | 0.19 | 0.02 |
| Creatine kinase, U/L | 861 | 628 | 1150 | 664 | 1163 | 183 |
| Sodium, mEq/L | 143.44 | 143.17 | 143.19 | 142.50 | 143.00 | 0.53 |
| Potassium, mEq/L | 5.77 | 5.89 | 5.61 | 5.64 | 5.60 | 0.15 |
| Chloride, mEq/L | 102.61$^x$ | 103.72$^y$ | 101.92$^x$ | 102.67$^{xy}$ | 102.56$^x$ | 0.36 |
| $CO_2$, mEq/L | 28.44 | 26.83 | 28.31 | 28.11 | 28.11 | 0.94 |
| Anion gap, mEq/L | 18.14 | 18.51 | 18.58 | 17.37 | 17.94 | 0.99 |

[1]Six pens of 3 pigs each per treatment; pen mean was the experimental unit.
$^{x,y,z}$Means in the same row with no common superscript differ (P < 0.05).

Certain measures of nitrogen and protein metabolism were also impacted by dietary treatments. Serum urea N, total protein and albumin were each depressed in pigs fed the aflatoxin contaminated diets containing no additives as compared to pigs fed the uncontaminated control diet (Table 10; P<0.05). Supplementation with the mycotoxin binder and antioxidants (treatment 5) returned serum urea N to a level not different from the uncontaminated controls. Furthermore, the diet supplemented with mycotoxin binder alone (treatment 3) or mycotoxin binder and antioxidants (treatment 5) restored serum total protein and albumin to levels not different from the uncontaminated controls. Conversely, serum globulin, a class of proteins that includes transport proteins and immunoglobulins, was elevated in the aflatoxin contaminated diet compared to the uncontaminated control (P<0.05). Addition of mycotoxin binder to contaminated diets returned serum globulin concentration to a level not different from the uncontaminated controls.

Serum chloride concentration was slightly but significantly elevated for pigs fed the aflatoxin contaminated diet compared to the uncontaminated control and the contaminated diets supplemented with mycotoxin binder (Table 10; P<0.05). Analysis of variance indicated a trend for an effect of diet on serum glucose concentration (F test P-value=0.095) that appeared to be predominantly related to reduced serum glucose in pigs fed the aflatoxin contaminated diet with no additives. Other serum metabolites and minerals were not significantly affected by diet (P>0.05).

Figure 10:
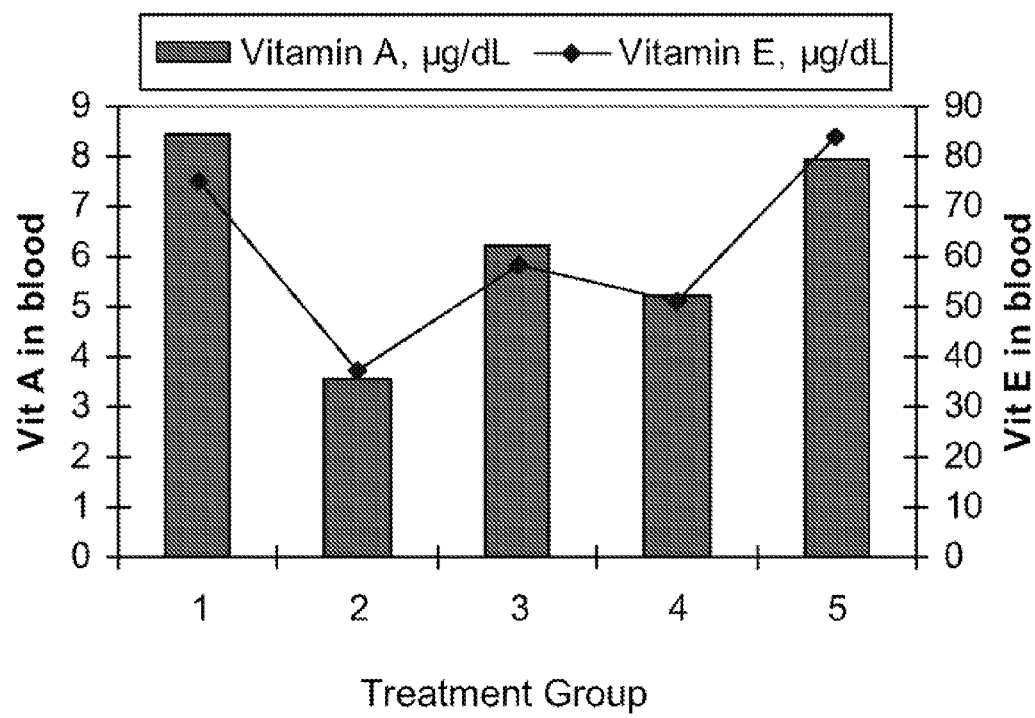
FIG. 10 illustrates that a combination of antioxidants and a mycotoxin binder improves Vitamins A and E status in aflatoxin challenged pigs. Plotted are the serum levels of Vitamins A and E as a function of treatment group. Treatment group 1 was not challenged and received no dietary supplements. Treatment group 2 was challenged with aflatoxin. Treatment group 3 was challenged with aflatoxin and received a dietary mycotoxin binder. Treatment group 4 was challenged with aflatoxin and received dietary antioxidants. Treatment group 5 was challenged with aflatoxin and received dietary antioxidants and a mycotoxin binder.

Serum vitamin A and E concentrations were reduced 58 and 50%, respectively, by the aflatoxin challenge (see FIG. 10). Treatment with mycotoxin binder alone (treatment 3) significantly spared vitamin A and E levels compared to the aflatoxin challenged pigs (treatment 2). Antioxidants alone (treatment 4) did not significantly increase Vitamin A or E levels above the challenged pigs. The combination of mycotoxin binder and antioxidant (treatment 5) resulted in vitamin E and vitamin A levels similar to positive control pigs (treatment 1), whereas either treatment alone had levels significantly lower than positive controls (FIG. 10). Plasma malondialdehye (MDA) levels were not affected by treatment. Antioxidant alone (treatment 4) resulted in a significant reduction in *Mycoplasma hyopneumoniae* titers compared to control (treatment 1), aflatoxin challenged pigs (treatment 2), and mycotoxin binder alone (treatment 3) fed pigs.

Summary.

Feeding young growing pigs a diet contaminated with 500 ppb aflatoxin B1 had profound negative effects on growth rate that was associated with a pronounced reduction in feed consumption. The serum chemistry profile of pigs fed the aflatoxin contaminated diet was characteristic of moderate aflatoxicosis with elevated GGT level, slightly elevated direct (conjugated) bilirubin, reduced serum urea N, and reduced total protein and albumin levels. The results clearly demonstrated that supplementing a diet of this aflatoxin contamination level with the mycotoxin binder prevented the negative effects on growth performance and restored the serum chemistry profile to that of pigs not experiencing toxicity. Supplementing the antioxidants ethoxyquin (125 ppm) and TBHQ (10 ppm) to the contaminated diet did not produce the same positive response as the mycotoxin binder. However, some data suggested a positive influence of the antioxidants. Compared to the unsupplemented contaminated diet, growth rate numerically favored pigs fed the contaminated diet with antioxidants and conjugated bilirubin was not elevated. In addition, serum GGT for these pigs was significantly reduced (P<0.05) compared to the unsupplemented pigs, although not to the same degree as for pigs fed the diet with the mycotoxin binder or the those fed the uncontaminated diet. In the case of the antioxidants treatment, a limited positive metabolic influence may be occurring in pigs once aflatoxin has been absorbed from the G.I. tract. When the combination of antioxidant and mycotoxin binder was fed, higher blood vitamin A and vitamin E levels were observed indicating an improvement in oxidative balance in pigs fed the two products over when the products were fed alone.

What is claimed is:

1. A method for increasing milk yield and milk efficiency in an animal, the method comprising feeding to the animal as a part of its feed ration a combination comprising at least one antioxidant chosen from 6-ethoxy-1,2-dihydro-2,2,4-trimethylquinoline, tertiary butyl hydroquinone, butylated hydroxyanisole, and butylated hydroxytoluene; a hydroxy analog of methionine; and at least one organic trace mineral, the organic trace mineral comprising a metal chelate or a metal salt, the metal chelate or metal salt comprising at least one metal ion and at least one ligand, the ligand comprising a compound comprising Formula (III):

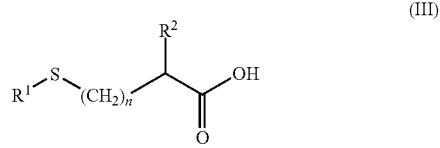

wherein:
  $R^1$ is selected from the group consisting of methyl and ethyl;
  $R^2$ is selected from the group consisting of hydroxy and amino; and
  n is an integer from 0 to 2;
wherein feeding the combination to the animal increases milk yield and milk efficiency without an increase in the animal's dry matter intake compared to feeding the animal a feed ration not containing the combination.

2. The method of claim 1, further comprising the step of determining the milk yield or milk efficiency of the animal.

3. The method of claim 1, wherein the hydroxy analog of methionine is chosen from 2-hydroxy-4-methylthiobutanoic acid and a calcium salt of 2-hydroxy-4-methylthiobutanoic acid.

4. The method of claim 1, wherein the metal ion is chosen from manganese ions, zinc ions, magnesium ions, copper ions, selenium ions, iron ions, and combinations thereof; and the ligand is 2-hydroxy-4-methylthiobutanoic acid.

5. The method of claim 1, wherein the antioxidant is a mixture of 6-ethoxy-1,2-dihydro-2,2,4-trimethylquinoline and tertiary butyl hydroquinone.

6. The method of claim 1, wherein the hydroxy analog of methionine is a calcium salt of 2-hydroxy-4-methylthiobutanoic acid; the antioxidant is a mixture of 6-ethoxy-1,2-dihydro-2,2,4-trimethylquinoline and tertiary butyl hydroquinone and the metal ion is a mixture of zinc ions, manganese ions, and copper ions; and the ligand is 2-hydroxy-4-methylthiobutanoic acid.

7. The method of claim 6, wherein the animal is a dairy cow.

8. The method of claim 7, further comprising the step of determining the milk yield or milk efficiency of the animal.

9. The method of claim 1, further comprising adding at least one organic acid to the combination chosen from formic acid, acetic acid, propionic acid, butanoic acid, benzoic acid, lactic acid, malic acid, tartaric acid, mandelic acid, citric acid, fumaric acid, sorbic acid, boric acid, succinic acid, adipic acid, glycolic acid, glutaric acid, 2-hydroxy-4-methylthiobutanoic acid, and mixtures thereof.

10. A method for increasing the amount of milk fat and milk protein in milk produced by an animal, the method comprising feeding to the animal as a part of its feed ration a combination comprising at least one antioxidant chosen from 6-ethoxy-1,2-dihydro-2,2,4-trimethylquinoline, tertiary butyl hydroquinone, butylated hydroxyanisole, and butylated hydroxytoluene; a hydroxy analog of methionine; and at least one organic trace mineral, the organic trace mineral comprising a metal chelate or a metal salt, the metal chelate or metal salt comprising at least one metal ion and at least one ligand, the ligand comprising a compound comprising Formula (III):

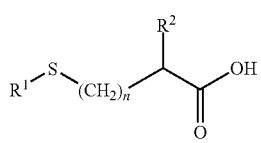

(III)

wherein:
i. $R^1$ is selected from the group consisting of methyl and ethyl;
ii. $R^2$ is selected from the group consisting of hydroxy and amino; and
iii. n is an integer from 0 to 2;
wherein feeding the combination to the animal increases the amount of milk fat and milk protein in milk produced by the animal compared to the amount of milk fat and milk protein in milk from the animal feeding the animal a feed ration not containing the combination.

11. The method of claim 10, further comprising the step of determining the amount of milk fat and milk protein.

12. The method of claim 10, wherein the hydroxy analog of methionine is chosen from 2-hydroxy-4-methylthiobutanoic acid and a calcium salt of 2-hydroxy-4-methylthiobutanoic acid.

13. The method of claim 10, wherein the metal ion is chosen from manganese ions, zinc ions, magnesium ions, copper ions, selenium ions, iron ions, and combinations thereof; and the ligand is 2-hydroxy-4-methylthiobutanoic acid.

14. The method of claim 10, wherein the antioxidant is a mixture of 6-ethoxy-1,2-dihydro-2,2,4-trimethylquinoline and tertiary butyl hydroquinone.

15. The method of claim 10, wherein the hydroxy analog of methionine is a calcium salt of 2-hydroxy-4-methylthiobutanoic acid; the antioxidant is a mixture of 6-ethoxy-1,2-dihydro-2,2,4-trimethylquinoline and tertiary butyl hydroquinone and the metal ion is a mixture of zinc ions, manganese ions, and copper ions; and the ligand is 2-hydroxy-4-methylthiobutanoic acid.

16. The method of claim 15, wherein the animal is a dairy cow.

17. The method of claim 16, further comprising the step of determining the amount of milk fat and milk protein.

18. The method of claim 10, further comprising adding at least one organic acid to the combination chosen from formic acid, acetic acid, propionic acid, butanoic acid, benzoic acid, lactic acid, malic acid, tartaric acid, mandelic acid, citric acid, fumaric acid, sorbic acid, boric acid, succinic acid, adipic acid, glycolic acid, glutaric acid, 2-hydroxy-4-methylthiobutanoic acid, and mixtures thereof.

19. The method of claim 10, further comprising the step of increasing milk yield and milk efficiency without an increase in the animal's dry matter intake compared to feeding the animal a feed ration not containing the combination.

20. The method of claim 1, further comprising the step of increasing the amount of milk fat and milk protein in milk produced by the animal compared to the amount of milk fat and milk protein in milk from the animal feeding the animal a feed ration not containing the combination.

* * * * *